(12) United States Patent
Zhang et al.

(10) Patent No.: US 11,332,765 B2
(45) Date of Patent: May 17, 2022

(54) VIRIDIFLOROL PRODUCTION IN AUXOTROPHIC ESCHERICHIA COLI

(71) Applicant: AGENCY FOR SCIENCE, TECHNOLOGY AND RESEARCH, Singapore (SG)

(72) Inventors: Congqiang Zhang, Singapore (SG); Xixian Chen, Singapore (SG); Sudha Shukal, Singapore (SG)

(73) Assignee: AGENCY FOR SCIENCE, TECHNOLOGY AND RESEARCH, Singapore (SG)

(\*) Notice: Subject to any disclaimer, the term of this patent is extended or adjusted under 35 U.S.C. 154(b) by 0 days.

(21) Appl. No.: 16/931,711

(22) Filed: Jul. 17, 2020

(65) Prior Publication Data

US 2021/0040520 A1 Feb. 11, 2021

(30) Foreign Application Priority Data

Aug. 8, 2019 (SG) .......................... 10201907354Y

(51) Int. Cl.
*C12P 15/00* (2006.01)
*C12N 9/88* (2006.01)
*C12N 15/70* (2006.01)

(52) U.S. Cl.
CPC .............. *C12P 15/00* (2013.01); *C12N 9/88* (2013.01); *C12N 15/70* (2013.01)

(58) Field of Classification Search
CPC .......... C12N 9/88; C12N 15/70; C12N 15/67; C12P 7/00; C12P 15/00; C12P 5/007
See application file for complete search history.

(56) References Cited

PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Shukal et al., Systematic engineering for high-yield production of viridiflorol and amorphadiene in auxotrophic *Escherichia coli*. Metabol. Eng., 2019, vol. 55: 170-178. (Year: 2019).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Takahashi et al., "Metabolic Engineering of Sesquiterpene Metabolism in Yeast", Biotechnol Bioeng., vol. 97, No. 1, May 1, 2007, pp. 170-181.
Wong et al., "Microbial Production of Isoprenoids", Springer International Publishing AG 2017, S.Y. Lee (ed)., Consequences of Microbial Interactions with Hydrocarbons, Oils, and Lipids: Production of Fuels and Chemicals, Handbook of Hydrocarbon and Lipid Microbiology, 24 pages.
Zhang et al., "Combining Genotype Improvement and Statistical Media Optimization for Isoprenoid Production in *E. coli*", PLOS ONE, vol. 8, Issue 10, Oct. 2013, 11 pages.
Ajikumar et al., "Terpenoids: Opportunities for Biosynthesis of Natural Product Drugs Using Engineered Microorganisms", Molecular Pharmaceutics, vol. 5, No. 2, 2008, pp. 167-190.
Schempp et al., "Microbial Cell Factories for the Production of Terpenoid Flavor and Fragrance Compounds", Journal of Agricultural and Food Chemistry, vol. 66, 2018, pp. 2247-2258.
Vickers et al., "Metabolic Engineering of Volatile Isoprenoids in Plants and Microbes", Plant, Cell and Environment, vol. 37, 2014, pp. 1753-1775.
Trevizan et al., "Anti-inflammatory, Antioxidant and Anti-*Mycobacterium tuberculosis* Activity of Viridiflorol: The Major Constituent of Allophylus Edulis", Journal of Ethnopharmacology, Septenber 2016, 25 pages.
Hulley et al., "Antimicrobial Activity of *Elytropappus rhinocerotis* (Asteraceae) Against Microorganisms Associated with Foot Odour and Skin Ailments", Journal of Ethnopharmacology, vol. 228, 2019, pp. 92-98.
Padovan et al., "The Molecular Basis of Host Plant Selection of *Melaleuca quinquenervia* by a Successful Biological Control Agent", Phytochemistry vol. 71, 2010, pp. 1237-1244.
Gilabert et al., "Sesqui- and Triterpenoids From the Liverwort *Lepidozia chordulifera* Inhibitors of Bacterial Biofilm and Elastase Activity of Human Pathogenic Bacteria", Phytomedicine, vol. 22, 2015, pp. 77-85.
Rosano et al., "Recombinant Protein Expression in *Escherichia coli*: Advances and Challenges", Frontiers in Microbiology, vol. 5, Article 172, Apr. 2014, 17 pages.

(Continued)

*Primary Examiner* — Ganapathirama Raghu
(74) *Attorney, Agent, or Firm* — Marshall, Gerstein & Borun LLP

(57) ABSTRACT

A method of increasing terpenoid production in a host cell that produces one or more terpenoids, comprising: a) providing a host cell that produces one or more terpenoids, said host cell comprising a vector comprising a polynucleotide sequence encoding a terpene synthase enzyme; b) modifying the vector to:
i. introduce an inducible promoter operably linked to the polynucleotide sequence encoding the terpene synthase enzyme; and ii. introduce a polynucleotide sequence encoding a ribosomal binding site (RBS) that increases translation initiation rate of the terpenoid compared to a wild type ribosomal binding site; c) determining the dosage of an inducer capable of inducing the inducible promoter; d) culturing the host cell in a culture medium in the presence of the inducer at the dosage determined from step c); and e) isolating the terpenoid from the culture medium.

16 Claims, 36 Drawing Sheets
(22 of 36 Drawing Sheet(s) Filed in Color)
Specification includes a Sequence Listing.

(56) References Cited

PUBLICATIONS

Schalk et al., "Toward a Biosynthetic Route to Sclareol and Amber Odorants", Journal of the American Chemical Society, J. Am. Chem. Soc., vol. 134, 2012, pp. 18900-18903.

Chen et al., "Statistical Experimental Design Guided Optimization of a One-pot Biphasic Multienzyme Total Synthesis of Amorpha-4,11-diene", PLOS One, vol. 8, Issue 11, Nov. 2013, 10 pages.

Li et al., "Reprogramming the Chemodiversity of Terpenoid Cyclization by Remolding the Active Site Contour of epi-Isozizaene Synthase", Biochemistry, vol. 53, 2014, pp. 1155-1168.

Leonard et al., "Combining Metabolic and Protein Engineering of a Terpenoid Biosynthetic Pathway to Overproduction and Selectivity Control", PNAS, vol. 107, No. 31, Aug. 3, 2010, 6 pages.

Pfleger et al., "Biological Synthesis Unbounded?", Nature Biotechnology, vol. 33, No. 11, Nov. 2015, pp. 1148-1149.

Du et al., "Customized Optimization of Metabolic Pathways by Combinatorial Transcriptional Engineering", Nucleic Acids Research, vol. 40, No. 18, Jun. 19, 2012, 10 pages.

Xu et al., "Modular Optimization of Multi-gene Pathways for Fatty Acids Production in *E. coli*", Nature Communications, Jan. 29, 2013, 8 pages.

Ajikumar et al., "Isoprenoid Pathway Optimization for Taxol Precursor Overproduction in *Escherichia coli*", Science, vol. 330, Oct. 1, 2010, pp. 70-74.

Datsenko et al., "One-step Inactivation of Chromosomal Genes in *Escherichia coli* K-12 Using PCR Products", PNAS, vol. 97, No. 12, Jun. 6, 2020, pp. 6640-6645.

Farasat et al., "Efficient Search, Mapping, and Optimization of Multi-protein Genetic Systems in Diverse Bacteria", Molecular Systems Biology, 10:731, 2014, 18 pages.

Cane et al., "Exploration and Mining of the Bacterial Terpenome", Accounts of Chemical Research, vol. 45, No. 3, 2012, pp. 463-472.

F. Studier, "Protein Production by Auto-induction in High-density Shaking Cultures", Protein Expression and Purification, vol. 41, 2005, pp. 207-234.

Falara et al., "The Tomato Terpene Synthase Gene Family", Plant Physiology, vol. 157, Oct. 2011, pp. 770-789.

Zhang et al., Experimental Design-aided Systematic Pathway Optimization of Glucose Uptake and Deoxyxylulose Phosphate Pathway for Improved Amorphadiene Production, Appl Microbiol Biotechnol, vol. 99, 2015, pp. 3825-3837.

Perez et a., "Production of Jet Fuel Precursor Monoterpenoids From Engineered *Escherichia coli*", Biotechnology and Bioengineering, 114(8), Jan. 8, 2017, 29 pages.

Zhang et al., "Multidimensional Heuristic Process for High-yield Production of Astaxanthin and Fragrance Molecules in *Escherichia coli*", Nature Communications, 9:1858, 2018, 12 pages.

Zhang et al., "A "plug-n-play" Modular Metabolic System for the Production of Apocarotenoids", Biotechnology and Bioengineering, vol. 115, 2018, pp. 174-183.

* cited by examiner $$Viridiflorol = a * M1 + b * M2 + c * M3 + d * M1^2 + e * M2^2 + g * M3^2 + h * M1 * M2 + i * M2 * M3 + j * M3 * M1$$

FIG. 3C

| | Strain ID | RBS Sequence | TIR (a.u.) | TIR % |
|---|---|---|---|---|
| SEQ ID NO: 1 | #12* | AAGAAGAGGCCTAAA | 11608 | 6% |
| SEQ ID NO: 2 | #31 | AGGAAGAGGCCTAAA | 15207 | 8% |
| SEQ ID NO: 3 | #32 | ATGAAGAGGCCTAAA | 8742 | 5% |
| SEQ ID NO: 4 | #33 | TAGAAGAGGCCTAAA | 17801 | 10% |
| SEQ ID NO: 5 | #34 | TGGAAGAGGCCTAAA | 4411 | 2% |
| SEQ ID NO: 6 | #35 | TTGAAGAGGCCTAAA | 13650 | 7% |
| SEQ ID NO: 7 | #36 | AAGAAGAGGCCTAAA | 65013 | 35% |
| SEQ ID NO: 60 | Design 1 | WDGAAGAGGCCTAAA | / | / |

FIG. 3D

| | Strain ID | RBS Sequence | TIR (a.u.) | TIR % |
|---|---|---|---|---|
| SEQ ID NO: 8 | #37 | ATAAGGAGGTATAAA | 186206 | 100% |
| SEQ ID NO: 9 | #38 | CTAAGGAGGTATAAA | 186206 | 100% |
| SEQ ID NO: 10 | #39 | TTAAGGAGGTATAAA | 140236 | 75% |
| SEQ ID NO: 11 | #40 | GTAAGGAGGTATAAA | 128165 | 69% |
| SEQ ID NO: 12 | #41 | CGAAGGAGGTATAAA | 123633 | 66% |
| SEQ ID NO: 13 | #42 | TGAAGGAGGTATAAA | 123633 | 66% |
| SEQ ID NO: 14 | #43 | GGAAGGAGGTATAAA | 103730 | 56% |
| SEQ ID NO: 15 | #44 | CTAAAGAGGTATAAA | 75021 | 40% |
| SEQ ID NO: 16 | #45 | ATAAAGAGGTATAAA | 73351 | 39% |
| SEQ ID NO: 17 | #46 | AGAAGGAGGTATAAA | 62661 | 34% |
| SEQ ID NO: 18 | #47 | TTAAAGAGGTATAAA | 49810 | 27% |
| SEQ ID NO: 19 | #48 | GTAAAGAGGTATAAA | 43716 | 23% |
| SEQ ID NO: 20 | #49 | CGAAAGAGGTATAAA | 32923 | 18% |
| SEQ ID NO: 21 | #50 | TGAAAGAGGTATAAA | 23598 | 13% |
| SEQ ID NO: 22 | #51 | GGAAAGAGGTATAAA | 17066 | 9% |
| SEQ ID NO: 23 | #52 | AGAAAGAGGTATAAA | 10309 | 6% |
| SEQ ID NO: 61 | Design 2 | NKAARGAGGTATAAA | / | / |

Ppi - pyrophosphate

Mg - magnesium

| "TRY" data | Viridiflorol |
|---|---|
| titre (g/L) | 25.7 |
| productivity (g/L/h) | 0.42 |
| yield (g/g glucose) | 0.22 |
| specific yield (g/g DCW) | 0.64 |

| "TRY" data | Amorpha-4,11-diene |
|---|---|
| titre (g/L) | 30 |
| productivity (g/L/h) | 0.38 |
| yield (g/g glucose) | 0.19 |
| specific yield (g/g DCW) | 0.44 |

Measure Position Value Cutoff signal peptide?
 max. C  26    0.244
 max. Y  26    0.450
 max. S   5    0.911
 mean S  1-25  0.834
     D   1-25  0.657  0.450  YES
Name=VS   SP='YES' Cleavage site between pos. 25 and 26: SLS-RK D=0.657 D-cutoff=0.450 Networks=SignalP-noTM

SEQUENCE LISTING

<160> NUMBER OF SEQ ID NOS: 63

<210> SEQ ID NO 1
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 1
aagaagaggc ctaaa                                                        15

<210> SEQ ID NO 2
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 2
aggaagaggc ctaaa                                                        15

<210> SEQ ID NO 3
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 3
atgaagaggc ctaaa                                                        15

<210> SEQ ID NO 4
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 4
tagaagaggc ctaaa                                                        15

<210> SEQ ID NO 5
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 5
tggaagaggc ctaaa                                                        15

<210> SEQ ID NO 6
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 6
ttgaagaggc ctaaa                                                        15

<210> SEQ ID NO 7
<211> LENGTH: 15
<212> TYPE: DNA
<213> ORGANISM: Artificial Sequence

```
<220> FEATURE:
<223> OTHER INFORMATION: Encoding ribosomal binding site

<400> SEQUENCE: 7
aagaagaggc ctaaa                                                    15

<210> SEQ ID NO 8
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 8
ataaggaggt ataaa                                                    15

<210> SEQ ID NO 9
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 9
ctaaggaggt ataaa                                                    15

<210> SEQ ID NO 10
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 10
ttaaggaggt ataaa                                                    15

<210> SEQ ID NO 11
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 11
gtaaggaggt ataaa                                                    15

<210> SEQ ID NO 12
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 12
cgaaggaggt ataaa                                                    15

<210> SEQ ID NO 13
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 13
tgaaggaggt ataaa                                                    15
```

```
<210> SEQ ID NO 14
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 14
ggaaggaggt ataaa                                                    15

<210> SEQ ID NO 15
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 15
ctaaagaggt ataaa                                                    15

<210> SEQ ID NO 16
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 16
ataaagaggt ataaa                                                    15

<210> SEQ ID NO 17
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 17
agaaggaggt ataaa                                                    15

<210> SEQ ID NO 18
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 18
ttaaagaggt ataaa                                                    15

<210> SEQ ID NO 19
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 19
gtaaagaggt ataaa                                                    15

<210> SEQ ID NO 20
<211> LENGTH: 15
<212> TYPE: DNA
<213> ORGANISM: Artificial Sequence
<220> FEATURE:
<223> OTHER INFORMATION: Encoding ribosomal binding site
```

<400> SEQUENCE: 20
cgaaagaggt ataaa                                                                                    15

<210> SEQ ID NO 21
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 21
tgaaagaggt ataaa                                                                                    15

<210> SEQ ID NO 22
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 22
ggaaagaggt ataaa                                                                                    15

<210> SEQ ID NO 23
<211> LENGTH: 15
<212> TYPE: DNA
<213> ORGANISM: Artificial Sequence
<220> FEATURE:
<223> OTHER INFORMATION: Encoding ribosomal binding site

<400> SEQUENCE: 23
agaaagaggt ataaa                                                                                    15

<210> SEQ ID NO 24
<211> LENGTH: 430
<212> TYPE: PRT
<213> ORGANISM: Melaleuca quinquenervia

<400> SEQUENCE: 24

Met Ala Ser Ser Leu Leu Glu Pro Ser Leu Ala Ile Ala Leu Val
1               5                   10                  15

Ile Leu Leu Ala Ser Val Ser Leu Ser Arg Lys Lys Arg Pro Ala Ala
                20                  25                  30

Pro Glu Pro Gln Gly Leu Ser Val Leu Gly Asn Leu Phe Asp Ile Pro
        35                  40                  45

Lys Arg Ala Ser Ser Ile Ile Tyr Leu Ala Leu Gly Lys Pro Tyr Asn
    50                  55                  60

Thr Leu Thr Lys Arg Ala Val Ser Gln Leu Gln Gly Tyr Thr Pro Gly
65                  70                  75                  80

Ser His Ile Asp Ala Thr Ser His Ser Pro Arg Val Phe Arg Leu Pro
                85                  90                  95

Asn Leu Glu Glu Thr Phe Ser Val Phe Pro Asp His Gly Leu Asn Pro
            100                 105                 110

Asn Tyr Thr Ser Ala Arg Thr Asp Ser Arg Ala Trp Ile Asn Gln Tyr
        115                 120                 125

Thr Lys Val Val Cys Gly Pro Lys Met Val Ala Phe Met Asn Asn Cys
    130                 135                 140

Glu Phe Glu Leu Ser Asn Ser His Cys Tyr Pro Tyr Ala Gly Tyr Lys
145                 150                 155                 160

-continued

```
Gly Leu Lys Ala Thr Met Asp Leu Thr Asn Ile Leu Trp Leu Tyr Asp
                165                 170                 175

Glu Tyr Thr Asp Thr Gly Ser Gly Ala Glu Ala Val Lys Ala Ala Gly
            180                 185                 190

Ile Val Ala Arg Ala Leu Arg Glu Pro Asp Tyr Asp Asp Gly Thr Trp
        195                 200                 205

Val Cys Arg Met Met Lys Ser Phe Lys Gln Asn His Ile Asp Lys Ala
    210                 215                 220

Gly Pro Gly Val Ala Arg Arg Phe Ile Asp Asn Phe Cys Asn Tyr Val
225                 230                 235                 240

Glu Val Val Gly Arg Glu Ala Glu Leu Arg Glu Lys Asn Glu Val Leu
                245                 250                 255

Asp Ile Pro Asn Tyr Val Thr Phe Arg Arg Glu Thr Ser Ala Val Arg
            260                 265                 270

Thr Cys Phe Asp Leu Val Glu Tyr Cys Leu Asp Leu Asp Leu Pro Gln
        275                 280                 285

Tyr Val His Asp Asp Pro Val Phe Ile Ser Gly Tyr Asn Ala Gly Met
    290                 295                 300

Asp Leu Val Phe Trp Ala Asn Asp Leu Val Ser Tyr Asn Met Glu Gln
305                 310                 315                 320

Ser Lys Gly His Ser Gly Ala Asn Val Val Thr Val Ile Met Lys Ser
                325                 330                 335

Lys Gly Val Asp Leu Gln Thr Ala Val Asp Phe Leu Gly Gly Tyr Cys
            340                 345                 350

Glu Ala Leu Thr Ala Gln Leu Leu Glu Ala Lys Arg Ile Leu Gln Ala
        355                 360                 365

Arg Ser Asp Ala Ala Tyr Ser Arg Asp Val Val Arg Leu Met Asp Ala
    370                 375                 380

Phe Gly Asp Trp Val Arg Gly Asn Val Ala Trp Ser Phe Glu Thr Glu
385                 390                 395                 400

Arg Tyr Phe Gly Lys Glu Asn Lys Arg Val Lys Glu Thr Leu Leu Val
                405                 410                 415

Glu Leu Lys Glu Pro Phe Val Gly Ala Leu Ala Leu Lys Glu
            420                 425                 430

<210> SEQ ID NO 25
<211> LENGTH: 1054
<212> TYPE: PRT
<213> ORGANISM: Escherichia coli

<400> SEQUENCE: 25

Met Pro Pro Leu Phe Lys Gly Leu Lys Gln Met Ala Lys Pro Ile Ala
1               5                   10                  15

Tyr Val Ser Arg Phe Ser Ala Lys Arg Pro Ile His Ile Ile Leu Phe
                20                  25                  30

Ser Leu Ile Ile Ser Ala Phe Ala Tyr Leu Ser Val Ile Gln Tyr Tyr
            35                  40                  45

Phe Asn Gly Trp Gln Leu Asp Ser Asn Ser Val Phe Glu Thr Ala Pro
        50                  55                  60

Asn Lys Asp Ser Asn Thr Leu Phe Gln Glu Cys Ser His Tyr Tyr Arg
65                  70                  75                  80

Asp Ser Ser Leu Asp Gly Trp Val Ser Ile Thr Ala His Glu Ala Ser
                85                  90                  95

Glu Leu Pro Ala Pro His His Tyr Tyr Leu Leu Asn Leu Asn Phe Asn
            100                 105                 110
```

```
Ser Pro Asn Glu Thr Asp Ser Ile Pro Glu Leu Ala Asn Thr Val Phe
            115                 120                 125

Glu Lys Asp Asn Thr Lys Tyr Ile Leu Gln Glu Asp Leu Ser Val Ser
130                 135                 140

Lys Glu Ile Ser Ser Thr Asp Gly Thr Lys Trp Arg Leu Arg Ser Asp
145                 150                 155                 160

Arg Lys Ser Leu Phe Asp Val Lys Thr Leu Ala Tyr Ser Leu Tyr Asp
                165                 170                 175

Val Phe Ser Glu Asn Val Thr Gln Ala Asp Pro Phe Asp Val Leu Ile
            180                 185                 190

Met Val Thr Ala Tyr Leu Met Met Phe Tyr Thr Ile Phe Gly Leu Phe
            195                 200                 205

Asn Asp Met Arg Lys Thr Gly Ser Asn Phe Trp Leu Ser Ala Ser Thr
210                 215                 220

Val Val Asn Ser Ala Ser Ser Leu Phe Leu Ala Leu Tyr Val Thr Gln
225                 230                 235                 240

Cys Ile Leu Gly Lys Glu Val Ser Ala Leu Thr Leu Phe Glu Gly Leu
                245                 250                 255

Pro Phe Ile Val Val Val Gly Phe Lys His Lys Ile Lys Ile Ala
            260                 265                 270

Gln Tyr Ala Leu Glu Lys Phe Glu Arg Val Gly Leu Ser Lys Arg Ile
            275                 280                 285

Thr Thr Asp Glu Ile Val Phe Glu Ser Val Glu Glu Gly Gly Arg
            290                 295                 300

Leu Ile Gln Asp His Leu Leu Cys Ile Phe Ala Phe Ile Gly Cys Ser
305                 310                 315                 320

Met Tyr Ala His Gln Leu Lys Thr Leu Thr Asn Phe Cys Ile Leu Ser
                325                 330                 335

Ala Phe Ile Leu Ile Phe Glu Leu Ile Leu Thr Pro Thr Phe Tyr Ser
            340                 345                 350

Ala Ile Leu Ala Leu Arg Leu Glu Met Asn Val Ile His Arg Ser Thr
            355                 360                 365

Ile Ile Lys Gln Thr Leu Glu Glu Asp Gly Val Val Pro Ser Thr Ala
370                 375                 380

Arg Ile Ile Ser Lys Ala Glu Lys Lys Ser Val Ser Ser Phe Leu Asn
385                 390                 395                 400

Leu Ser Val Val Ile Ile Met Lys Leu Ser Val Ile Leu Leu Phe
                405                 410                 415

Val Phe Ile Asn Phe Tyr Asn Phe Gly Ala Asn Trp Val Asn Asp Ala
            420                 425                 430

Phe Asn Ser Leu Tyr Phe Asp Lys Glu Arg Val Ser Leu Pro Asp Phe
            435                 440                 445

Ile Thr Ser Asn Ala Ser Glu Asn Phe Lys Glu Gln Ala Ile Val Ser
450                 455                 460

Val Thr Pro Leu Leu Tyr Tyr Lys Pro Ile Lys Ser Tyr Gln Arg Ile
465                 470                 475                 480

Glu Asp Met Val Leu Leu Leu Arg Asn Val Ser Val Ala Ile Arg
                485                 490                 495

Asp Arg Phe Val Ser Lys Leu Val Leu Ser Ala Leu Val Cys Ser Ala
            500                 505                 510

Val Ile Asn Val Tyr Leu Leu Asn Ala Ala Arg Ile His Thr Ser Tyr
            515                 520                 525
```

```
Thr Ala Asp Gln Leu Val Lys Thr Glu Val Thr Lys Lys Ser Phe Thr
530                 535                 540

Ala Pro Val Gln Lys Ala Ser Thr Pro Val Leu Thr Asn Lys Thr Val
545                 550                 555                 560

Ile Ser Gly Ser Lys Val Lys Ser Leu Ser Ser Ala Gln Ser Ser Ser
            565                 570                 575

Ser Gly Pro Ser Ser Ser Ser Glu Glu Asp Asp Ser Arg Asp Ile Glu
            580                 585                 590

Ser Leu Asp Lys Lys Ile Arg Pro Leu Glu Glu Leu Glu Ala Leu Leu
        595                 600                 605

Ser Ser Gly Asn Thr Lys Gln Leu Lys Asn Lys Glu Val Ala Ala Leu
        610                 615                 620

Val Ile His Gly Lys Leu Pro Leu Tyr Ala Leu Glu Lys Lys Leu Gly
625                 630                 635                 640

Asp Thr Thr Arg Ala Val Ala Val Arg Arg Lys Ala Leu Ser Ile Leu
                645                 650                 655

Ala Glu Ala Pro Val Leu Ala Ser Asp Arg Leu Pro Tyr Lys Asn Tyr
                660                 665                 670

Asp Tyr Asp Arg Val Phe Gly Ala Cys Cys Glu Asn Val Ile Gly Tyr
            675                 680                 685

Met Pro Leu Pro Val Gly Val Ile Gly Pro Leu Val Ile Asp Gly Thr
690                 695                 700

Ser Tyr His Ile Pro Met Ala Thr Thr Glu Gly Cys Leu Val Ala Ser
705                 710                 715                 720

Ala Met Arg Gly Cys Lys Ala Ile Asn Ala Gly Gly Gly Ala Thr Thr
                725                 730                 735

Val Leu Thr Lys Asp Gly Met Thr Arg Gly Pro Val Val Arg Phe Pro
            740                 745                 750

Thr Leu Lys Arg Ser Gly Ala Cys Lys Ile Trp Leu Asp Ser Glu Glu
        755                 760                 765

Gly Gln Asn Ala Ile Lys Lys Ala Phe Asn Ser Thr Ser Arg Phe Ala
        770                 775                 780

Arg Leu Gln His Ile Gln Thr Cys Leu Ala Gly Asp Leu Leu Phe Met
785                 790                 795                 800

Arg Phe Arg Thr Thr Thr Gly Asp Ala Met Gly Met Asn Met Ile Ser
                805                 810                 815

Lys Gly Val Glu Tyr Ser Leu Lys Gln Met Val Glu Glu Tyr Gly Trp
                820                 825                 830

Glu Asp Met Glu Val Val Ser Val Ser Gly Asn Tyr Cys Thr Asp Lys
            835                 840                 845

Lys Pro Ala Ala Ile Asn Trp Ile Glu Gly Arg Gly Lys Ser Val Val
        850                 855                 860

Ala Glu Ala Thr Ile Pro Gly Asp Val Val Arg Lys Val Leu Lys Ser
865                 870                 875                 880

Asp Val Ser Ala Leu Val Glu Leu Asn Ile Ala Lys Asn Leu Val Gly
                885                 890                 895

Ser Ala Met Ala Gly Ser Val Gly Gly Phe Asn Ala His Ala Ala Asn
                900                 905                 910

Leu Val Thr Ala Val Phe Leu Ala Leu Gly Gln Asp Pro Ala Gln Asn
            915                 920                 925

Val Glu Ser Ser Asn Cys Ile Thr Leu Met Lys Glu Val Asp Gly Asp
        930                 935                 940

Leu Arg Ile Ser Val Ser Met Pro Ser Ile Glu Val Gly Thr Ile Gly
```

```
                945                 950                 955                 960
Gly Gly Thr Val Leu Glu Pro Gln Gly Ala Met Leu Asp Leu Leu Gly
                    965                 970                 975

Val Arg Gly Pro His Ala Thr Ala Pro Gly Thr Asn Ala Arg Gln Leu
                980                 985                 990

Ala Arg Ile Val Ala Cys Ala Val Leu Ala Gly Glu Leu Ser Leu Cys
                995                 1000                1005

Ala Ala Leu Ala Ala Gly His Leu Val Gln Ser His Met Thr His
    1010                1015                1020

Asn Arg Lys Pro Ala Glu Pro Thr Lys Pro Asn Asn Leu Asp Ala
    1025                1030                1035

Thr Asp Ile Asn Arg Leu Lys Asp Gly Ser Val Thr Cys Ile Lys
    1040                1045                1050

Ser

<210> SEQ ID NO 26
<211> LENGTH: 502
<212> TYPE: PRT
<213> ORGANISM: Escherichia coli

<400> SEQUENCE: 26

Met Val Leu Thr Asn Lys Thr Val Ile Ser Gly Ser Lys Val Lys Ser
1               5                   10                  15

Leu Ser Ser Ala Gln Ser Ser Ser Gly Pro Ser Ser Ser Ser Ser Glu
            20                  25                  30

Glu Asp Asp Ser Arg Asp Ile Glu Ser Leu Asp Lys Lys Ile Arg Pro
        35                  40                  45

Leu Glu Glu Leu Glu Ala Leu Leu Ser Ser Gly Asn Thr Lys Gln Leu
    50                  55                  60

Lys Asn Lys Glu Val Ala Ala Leu Val Ile His Gly Lys Leu Pro Leu
65                  70                  75                  80

Tyr Ala Leu Glu Lys Lys Leu Gly Asp Thr Thr Arg Ala Val Ala Val
                85                  90                  95

Arg Arg Lys Ala Leu Ser Ile Leu Ala Glu Ala Pro Val Leu Ala Ser
            100                 105                 110

Asp Arg Leu Pro Tyr Lys Asn Tyr Asp Tyr Asp Arg Val Phe Gly Ala
        115                 120                 125

Cys Cys Glu Asn Val Ile Gly Tyr Met Pro Leu Pro Val Gly Val Ile
    130                 135                 140

Gly Pro Leu Val Ile Asp Gly Thr Ser Tyr His Ile Pro Met Ala Thr
145                 150                 155                 160

Thr Glu Gly Cys Leu Val Ala Ser Ala Met Arg Gly Cys Lys Ala Ile
                165                 170                 175

Asn Ala Gly Gly Gly Ala Thr Thr Val Leu Thr Lys Asp Gly Met Thr
            180                 185                 190

Arg Gly Pro Val Val Arg Phe Pro Thr Leu Lys Arg Ser Gly Ala Cys
        195                 200                 205

Lys Ile Trp Leu Asp Ser Glu Glu Gly Gln Asn Ala Ile Lys Lys Ala
    210                 215                 220

Phe Asn Ser Thr Ser Arg Phe Ala Arg Leu Gln His Ile Gln Thr Cys
225                 230                 235                 240

Leu Ala Gly Asp Leu Leu Phe Met Arg Phe Arg Thr Thr Thr Gly Asp
                245                 250                 255

Ala Met Gly Met Asn Met Ile Ser Lys Gly Val Glu Tyr Ser Leu Lys
```

```
            260                 265                 270
Gln Met Val Glu Glu Tyr Gly Trp Glu Asp Met Glu Val Val Ser Val
        275                 280                 285

Ser Gly Asn Tyr Cys Thr Asp Lys Lys Pro Ala Ala Ile Asn Trp Ile
        290                 295                 300

Glu Gly Arg Gly Lys Ser Val Val Ala Glu Ala Thr Ile Pro Gly Asp
305                 310                 315                 320

Val Val Arg Lys Val Leu Lys Ser Asp Val Ser Ala Leu Val Glu Leu
                325                 330                 335

Asn Ile Ala Lys Asn Leu Val Gly Ser Ala Met Ala Gly Ser Val Gly
                340                 345                 350

Gly Phe Asn Ala His Ala Ala Asn Leu Val Thr Ala Val Phe Leu Ala
            355                 360                 365

Leu Gly Gln Asp Pro Ala Gln Asn Val Glu Ser Ser Asn Cys Ile Thr
        370                 375                 380

Leu Met Lys Glu Val Asp Gly Asp Leu Arg Ile Ser Val Ser Met Pro
385                 390                 395                 400

Ser Ile Glu Val Gly Thr Ile Gly Gly Gly Thr Val Leu Glu Pro Gln
                405                 410                 415

Gly Ala Met Leu Asp Leu Leu Gly Val Arg Gly Pro His Ala Thr Ala
                420                 425                 430

Pro Gly Thr Asn Ala Arg Gln Leu Ala Arg Ile Val Ala Cys Ala Val
            435                 440                 445

Leu Ala Gly Glu Leu Ser Leu Cys Ala Ala Leu Ala Ala Gly His Leu
        450                 455                 460

Val Gln Ser His Met Thr His Asn Arg Lys Pro Ala Glu Pro Thr Lys
465                 470                 475                 480

Pro Asn Asn Leu Asp Ala Thr Asp Ile Asn Arg Leu Lys Asp Gly Ser
                485                 490                 495

Val Thr Cys Ile Lys Ser
            500

<210> SEQ ID NO 27
<211> LENGTH: 22
<212> TYPE: DNA
<213> ORGANISM: Escherichia coli

<400> SEQUENCE: 27
taatacgact cactataggg ga                                        22

<210> SEQ ID NO 28
<211> LENGTH: 22
<212> TYPE: DNA
<213> ORGANISM: Artificial Sequence
<220> FEATURE:
<223> OTHER INFORMATION: T7 promoter variant

<400> SEQUENCE: 28
taatacgact cactaatggg ga                                        22

<210> SEQ ID NO 29
<211> LENGTH: 22
<212> TYPE: DNA
<213> ORGANISM: Artificial Sequence
<220> FEATURE:
<223> OTHER INFORMATION: T7 promoter variant

<400> SEQUENCE: 29
```
taatacgact cactcgaggg ga                                           22

<210> SEQ ID NO 30
<211> LENGTH: 22
<212> TYPE: DNA
<213> ORGANISM: Artificial Sequence
<220> FEATURE:
<223> OTHER INFORMATION: T7 promoter variant

<400> SEQUENCE: 30
taatacgact cactataaag ga                                           22

<210> SEQ ID NO 31
<211> LENGTH: 50
<212> TYPE: DNA
<213> ORGANISM: Artificial Sequence
<220> FEATURE:
<223> OTHER INFORMATION: Primer

<400> SEQUENCE: 31
gttgtagaga gttgagttca tggaatccct gacgttacaa cccatcgctc             50

<210> SEQ ID NO 32
<211> LENGTH: 50
<212> TYPE: DNA
<213> ORGANISM: Artificial Sequence
<220> FEATURE:
<223> OTHER INFORMATION: Primer

<400> SEQUENCE: 32
cattcaggct gcctggctaa tccgcgccag ctgctcgaaa taatccggaa             50

<210> SEQ ID NO 33
<211> LENGTH: 50
<212> TYPE: DNA
<213> ORGANISM: Artificial Sequence
<220> FEATURE:
<223> OTHER INFORMATION: Primer

<400> SEQUENCE: 33
cggagccgtg atggctggaa acacaattgg acaactcttt cgcgtaacca             50

<210> SEQ ID NO 34
<211> LENGTH: 50
<212> TYPE: DNA
<213> ORGANISM: Artificial Sequence
<220> FEATURE:
<223> OTHER INFORMATION: Primer

<400> SEQUENCE: 34
ccagcgtgga atatcagtct tcacatcggc attttgcgcc cgttgccgta             50

<210> SEQ ID NO 35
<211> LENGTH: 50
<212> TYPE: DNA
<213> ORGANISM: Artificial Sequence
<220> FEATURE:
<223> OTHER INFORMATION: Primer

<400> SEQUENCE: 35
ctgcgggtac agtaattaag gtggatgtcg cgttatggag aggattgtcg             50

<210> SEQ ID NO 36
<211> LENGTH: 50
<212> TYPE: DNA
<213> ORGANISM: Artificial Sequence

```
<220> FEATURE:
<223> OTHER INFORMATION: Primer

<400> SEQUENCE: 36
ccccatttca gcttcaatgg catgaccaaa ggtgtgtccc agattcagta            50

<210> SEQ ID NO 37
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(13)
<223> OTHER INFORMATION: w is a or t
<220> FEATURE:
<221> NAME/KEY: misc_feature
<222> LOCATION: (14)..(14)
<223> OTHER INFORMATION: d is a, g or t

<400> SEQUENCE: 37
actaaataga ctwdgaagag gcctaaaatg catcaccatc acca                  44

<210> SEQ ID NO 38
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (11)..(11)
<223> OTHER INFORMATION: h is a, c or t
<220> FEATURE:
<221> NAME/KEY: misc_feature
<222> LOCATION: (12)..(12)
<223> OTHER INFORMATION: w is a or t

<400> SEQUENCE: 38
aggcctcttc hwagtctatt tagtgtgctt tgacgcttcc gtc                   43

<210> SEQ ID NO 39
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (17)..(17)
<223> OTHER INFORMATION: k is g or t
<220> FEATURE:
<221> NAME/KEY: misc_feature
<222> LOCATION: (20)..(20)
<223> OTHER INFORMATION: r is a or g

<400> SEQUENCE: 39
tccactaaat agactnkaar gaggtataaa atgcatcac                        39

<210> SEQ ID NO 40
<211> LENGTH: 38
<212> TYPE: DNA
<213> ORGANISM: Artificial Sequence
<220> FEATURE:
<223> OTHER INFORMATION: Primer
<220> FEATURE:
```

-continued

```
<221> NAME/KEY: misc_feature
<222> LOCATION: (1)..(1)
<223> OTHER INFORMATION: y is c or t
<220> FEATURE:
<221> NAME/KEY: misc_feature
<222> LOCATION: (4)..(4)
<223> OTHER INFORMATION: m is a or c
<220> FEATURE:
<221> NAME/KEY: misc_feature
<222> LOCATION: (5)..(5)
<223> OTHER INFORMATION: n is a, c, g, or t

<400> SEQUENCE: 40
yttmnagtct atttagtgga ggggaattgt tatccgct                              38

<210> SEQ ID NO 41
<211> LENGTH: 38
<212> TYPE: DNA
<213> ORGANISM: Artificial Sequence
<220> FEATURE:
<223> OTHER INFORMATION: Primer

<400> SEQUENCE: 41
catcaccatc accatcacac gagccatagc ccgcgcgt                              38

<210> SEQ ID NO 42
<211> LENGTH: 40
<212> TYPE: DNA
<213> ORGANISM: Artificial Sequence
<220> FEATURE:
<223> OTHER INFORMATION: Primer

<400> SEQUENCE: 42
gtgatggtga tggtgatgca ttttaggcct cttcttagtc                            40

<210> SEQ ID NO 43
<211> LENGTH: 567
<212> TYPE: PRT
<213> ORGANISM: Melaleuca quinquenervia

<400> SEQUENCE: 43
```

Met Ser Gln Val Ser Ala Ile Pro Thr Thr Ser Pro Asn Lys Gly Thr
1               5                   10                  15

Gly Asp Val Ile Glu Arg Arg Ser Ala Gly Tyr His Pro Ser Val Trp
            20                  25                  30

Gly Asp Tyr Phe Leu Lys Tyr Asp Ser Pro Ser Asn Ser Val Lys Phe
        35                  40                  45

Glu Phe Leu Gly Arg Val Glu Glu Gln Ile Glu Glu Leu Lys Gly Glu
    50                  55                  60

Val Arg Lys Met Leu Ala Gly Ala Val Asp Lys Pro Trp Gln Met Leu
65                  70                  75                  80

His Leu Ile Asp Gln Ile Gln Arg Leu Gly Ile Glu Tyr His Phe Glu
                85                  90                  95

Arg Glu Leu Asp Glu His Leu Glu Arg Ile His Lys Ser Phe Ser Gln
            100                 105                 110

Leu Thr His Gly Tyr Phe Lys Gly Asp Asp Leu Arg Met Ile Ser Leu
        115                 120                 125

Leu Phe Arg Leu Leu Arg Gln Gln Gly Tyr Asn Ile Ser Ser Glu Val
    130                 135                 140

Phe Asn Lys Phe Lys Asp Ser Glu Gly Asn Phe Gly Glu Ser Leu Ala
145                 150                 155                 160

Thr Asp Leu Arg Gly Leu Leu Ser Leu Tyr Glu Ala Cys His Leu Arg

```
            165                 170                 175
Cys His Gly Asp Ile Ile Leu Asp Glu Ala Leu Pro Phe Ala Ile Ser
            180                 185                 190

His Leu Glu Ser Ile Asp Glu Ser Lys Ala Gly Ala Asn Leu Ala Lys
            195                 200                 205

Gln Val Asn His Ala Leu Lys Gln Pro Leu Arg Arg Gly Leu Pro Arg
            210                 215                 220

Leu Glu Ala Arg Arg Tyr Ile Pro Leu Tyr Glu Glu Pro Ser His
225                 230                 235                 240

Asp Lys Val Leu Leu Ala Leu Ala Lys Leu Asp Phe Asn Leu Leu Gln
                    245                 250                 255

Glu Gln His Gln Lys Glu Leu Gly Asn Val Ser Arg Trp Trp Lys Asp
                    260                 265                 270

Ile Asp Val Pro Arg Lys Phe Pro Phe Ala Arg Asp Arg Ile Ala Glu
                    275                 280                 285

Leu Phe Phe Trp Ala Cys Gly Val Tyr Phe Glu Pro Glu Phe Ser Val
                    290                 295                 300

Ala Arg Val Ile Gln Ala Lys Ala Phe Ala Met Thr Ser Ile Leu Asp
305                 310                 315                 320

Asp Ile Tyr Asp Val Tyr Gly Thr Leu Glu Glu Leu Val Leu Leu Thr
                    325                 330                 335

Glu Ala Ile Glu Lys Trp Asp Val Asp Ala Met Asp Gly Leu Pro Glu
                    340                 345                 350

Tyr Met Gln Ala Phe Tyr Lys Glu Leu Leu His Phe Tyr Glu Glu Val
                    355                 360                 365

Gly Asn Glu Val Ala Ala Lys Gly Arg Ser Tyr Arg Leu Val Tyr Ala
                    370                 375                 380

Lys Glu Val Met Lys Lys Leu Ala Arg Ala Tyr Tyr Gln Glu Ala Lys
385                 390                 395                 400

Trp Phe His Thr Asn Tyr Thr Pro Thr Leu Glu Glu Tyr Met Pro Leu
                    405                 410                 415

Gln Leu Ile Thr Thr Gly Tyr Gly Met Met Ala Thr Thr Ser Leu Val
                    420                 425                 430

Gly Met Asp Asp Val Val Pro Lys His Val Phe Glu Trp Ser Ile Gly
                    435                 440                 445

Asp Cys Lys Ile Val Lys Ala Ala Gln Thr Ile Cys Arg Leu Met Asp
                    450                 455                 460

Asp Ile Ser Ser His Glu Phe Glu Gln Lys Arg Gly His Leu Val Ser
465                 470                 475                 480

Ser Val Glu Leu Leu Met Lys Glu Arg Ser Leu Ser Glu Arg Glu Ala
                    485                 490                 495

Gly Glu Glu Leu Gln Lys Gly Val Ile Asp Ala Trp Lys Asp Thr Asn
                    500                 505                 510

Glu Glu Phe Leu Arg Pro Thr Ala Val Pro Met Lys Ile Leu Thr Arg
                    515                 520                 525

Val Leu Asn Leu Ser Arg Ala Met Asp Val Leu Tyr Ser Asp Gly Asp
                    530                 535                 540

Asn Tyr Thr His Ser Gly Thr Lys Leu Lys Asp Phe Val Thr Ser Leu
545                 550                 555                 560

Phe Val Ser Pro Leu Pro Val
                    565

<210> SEQ ID NO 44
```

```
<211> LENGTH: 430
<212> TYPE: PRT
<213> ORGANISM: Agrocybe aegerita

<400> SEQUENCE: 44
```

| | | | | | | | | | | | | | | |
|---|---|---|---|---|---|---|---|---|---|---|---|---|---|---|
Met Ala Ser Ser Leu Leu Glu Pro Leu Ala Ala Ile Ala Leu Val
1               5                   10                  15

Ile Leu Leu Ala Ser Val Ser Leu Ser Arg Lys Lys Arg Pro Ala Ala
                20                  25                  30

Pro Glu Pro Gln Gly Leu Ser Val Leu Gly Asn Leu Phe Asp Ile Pro
        35                  40                  45

Lys Arg Ala Ser Ser Ile Ile Tyr Leu Ala Leu Gly Lys Pro Tyr Asn
50                  55                  60

Thr Leu Thr Lys Arg Ala Val Ser Gln Leu Gln Gly Tyr Thr Pro Gly
65                  70                  75                  80

Ser His Ile Asp Ala Thr Ser His Ser Pro Arg Val Phe Arg Leu Pro
                85                  90                  95

Asn Leu Glu Glu Thr Phe Ser Val Phe Pro Asp His Gly Leu Asn Pro
            100                 105                 110

Asn Tyr Thr Ser Ala Arg Thr Asp Ser Arg Ala Trp Ile Asn Gln Tyr
        115                 120                 125

Thr Lys Val Val Cys Gly Pro Lys Met Val Ala Phe Met Asn Asn Cys
130                 135                 140

Glu Phe Glu Leu Ser Asn Ser His Cys Tyr Pro Tyr Ala Gly Tyr Lys
145                 150                 155                 160

Gly Leu Lys Ala Thr Met Asp Leu Thr Asn Ile Leu Trp Leu Tyr Asp
                165                 170                 175

Glu Tyr Thr Asp Thr Gly Ser Gly Ala Glu Ala Val Lys Ala Ala Gly
            180                 185                 190

Ile Val Ala Arg Ala Leu Arg Glu Pro Asp Tyr Asp Gly Thr Trp
        195                 200                 205

Val Cys Arg Met Met Lys Ser Phe Lys Gln Asn His Ile Asp Lys Ala
210                 215                 220

Gly Pro Gly Val Ala Arg Arg Phe Ile Asp Asn Phe Cys Asn Tyr Val
225                 230                 235                 240

Glu Val Val Gly Arg Glu Ala Glu Leu Arg Glu Lys Asn Glu Val Leu
                245                 250                 255

Asp Ile Pro Asn Tyr Val Thr Phe Arg Arg Glu Thr Ser Ala Val Arg
            260                 265                 270

Thr Cys Phe Asp Leu Val Glu Tyr Cys Leu Asp Leu Asp Leu Pro Gln
        275                 280                 285

Tyr Val His Asp Asp Pro Val Phe Ile Ser Gly Tyr Asn Ala Gly Met
290                 295                 300

Asp Leu Val Phe Trp Ala Asn Asp Leu Val Ser Tyr Asn Met Glu Gln
305                 310                 315                 320

Ser Lys Gly His Ser Gly Ala Asn Val Val Thr Val Ile Met Lys Ser
                325                 330                 335

Lys Gly Val Asp Leu Gln Thr Ala Val Asp Phe Leu Gly Gly Tyr Cys
            340                 345                 350

Glu Ala Leu Thr Ala Gln Leu Leu Glu Ala Lys Arg Ile Leu Gln Ala
        355                 360                 365

Arg Ser Asp Ala Ala Tyr Ser Arg Asp Val Val Arg Leu Met Asp Ala
370                 375                 380

Phe Gly Asp Trp Val Arg Gly Asn Val Ala Trp Ser Phe Glu Thr Glu

```
            385                 390                 395                 400
Arg Tyr Phe Gly Lys Glu Asn Lys Arg Val Lys Glu Thr Leu Leu Val
                    405                 410                 415
Glu Leu Lys Glu Pro Phe Val Gly Ala Leu Ala Leu Lys Glu
            420                 425                 430

<210> SEQ ID NO 45
<211> LENGTH: 315
<212> TYPE: PRT
<213> ORGANISM: Galerina marginata

<400> SEQUENCE: 45

Met Thr Thr Ser Ile Leu Thr Phe Arg Leu Pro Arg Leu Glu Asp Thr
1               5                   10                  15

Phe Ser Val Phe Pro His Asn Gly Ile Asn His His Phe Ser Glu Cys
            20                  25                  30

Arg Asp Gln Ser Arg Glu Trp Ile Asp Lys Phe Leu Lys Ile Ala Leu
        35                  40                  45

Gly Pro Lys Met Cys Ile Phe Leu Ser Asn Cys Asn Leu Glu Leu Asn
    50                  55                  60

Ala Ala Tyr Thr His Pro Asn Ser Glu Pro Asp Gly Leu Arg Ala Val
65                  70                  75                  80

Met Asp Tyr Leu Asn Val Ala Trp Thr Tyr Asp Glu Phe Thr Asp Asp
                85                  90                  95

Leu Ala Gly Glu Glu Ala Ala Gln Ala Ala Val Phe Gly Ser Asn
            100                 105                 110

Val Ala Pro Arg Phe Ile Asp His Phe Cys Gln Ala Val Glu Lys Thr
        115                 120                 125

Gly Ala Glu Ala Asp Leu Arg Glu Lys Asp Gln Ile Leu Asp Leu Asp
    130                 135                 140

Gly Tyr Ile Ser Leu Arg Arg Gly Thr Val Ala Val Arg Val Val Phe
145                 150                 155                 160

Asp Leu Val Glu Tyr Cys Leu Gly Leu Asp Leu Pro Gln Tyr Val His
                165                 170                 175

Glu Asp Pro Ala Phe Ile Ser Ala Tyr Asn Ala Gly Ile Asp Leu Ile
            180                 185                 190

Ala Trp Thr Asn Asp Leu Phe Ser Tyr Asn Met Glu Gln Ala Lys Gly
        195                 200                 205

His Ser Gly Ala Asn Ile Ile Thr Val Val Met Glu Cys Lys Gly Ile
    210                 215                 220

Ser Leu Gln Ser Ala Ile Asp Phe Val Ala Gly Tyr Cys Glu Cys Leu
225                 230                 235                 240

Thr Gln Gln Phe Val Trp Ala Lys Ala Ala Leu Thr Leu Arg Thr Asp
                245                 250                 255

Pro Ile Phe Ser Lys Asp Ala Val Arg Cys Leu Glu Ala Tyr Gly Asp
            260                 265                 270

Trp Ile Lys Gly Asn Asp Glu Trp Ser Phe Ala Thr Glu Arg Tyr Phe
        275                 280                 285

Gly Lys Glu Asn Ala Leu Ile Lys Lys Thr Arg Ile Val Glu Leu Arg
    290                 295                 300

Lys Pro Phe Glu Gly Ala Ile Arg Ser Thr Glu
305                 310                 315

<210> SEQ ID NO 46
<211> LENGTH: 336
```

<212> TYPE: PRT
<213> ORGANISM: Moniliophthora roreri

<400> SEQUENCE: 46

```
Met Gly Arg Ala Thr Val Leu Thr Phe Thr Leu Pro Asp Leu Glu Met
1               5                   10                  15

Phe Ser Ala Leu Pro Asp Gly Gly Ile Asn Pro His His Glu Met Ala
            20                  25                  30

Arg Gln Glu Ser Arg Arg Trp Val Ala Gln Tyr Thr Asn Val Thr Phe
        35                  40                  45

Gly Pro Lys Met Lys Ala Phe Tyr Glu Lys Cys Glu Phe Glu Leu Ser
    50                  55                  60

Ser Ser Tyr Cys Tyr Pro Gln Leu Asp Arg Glu Gly Leu Arg Ala Val
65                  70                  75                  80

Met Asp Leu Val Asn Ile Leu Trp Phe Ala Asp Glu Val Thr Asp Ala
                85                  90                  95

Glu Thr Gly Ser Gly Ala Ser Arg Thr Ala Glu Thr Val Cys Arg Thr
            100                 105                 110

Leu Arg Asp Pro Glu Tyr Asn Asp Gly Thr Pro Leu Cys Leu Thr Gly
        115                 120                 125

Thr Phe Cys Ser Phe Arg Ile Asn His Leu Ser Lys Ala Gly Pro Glu
    130                 135                 140

Thr Ser Arg Arg Phe Met Glu His Cys His Glu Thr Phe Phe Ala Phe
145                 150                 155                 160

Ser Glu Glu Ala Glu Leu Arg Ala Gln Gly Glu Val Leu Ser Ile Ala
                165                 170                 175

Gly Tyr Leu Ser Leu Arg Lys Arg Asn Gly Arg Gly Val Arg Pro
            180                 185                 190

Cys Phe Asp Leu Ala Glu Cys Phe Leu Asp Met Asp Leu Pro Asp Cys
        195                 200                 205

Val His Arg Leu Glu Ile Phe Arg Arg Gly His Asp Ala Ala Val Asp
    210                 215                 220

Leu Val Gly Leu Ala Asn Asp Leu Tyr Ser Tyr Asn Val Gln Gln Ala
225                 230                 235                 240

Arg Gly Tyr Gly Thr Ser Asn Ile Val Thr Val Met Lys Ala Arg
                245                 250                 255

Lys Ile Gly Leu Gln Glu Ala Ser Asp Tyr Val Gly Cys Leu Cys Lys
            260                 265                 270

Thr Leu Leu Ser Asn Leu Gln Glu Ser Gln Arg Ala Ile Glu Asp Leu
        275                 280                 285

Ala Arg Asp Ala Lys Asp Glu Asp Ser Ala Asn Thr Phe Arg Asp Ala
    290                 295                 300

Leu Arg Ala Leu Glu Ala Tyr Ser His Trp Val Arg Gly Asn Ala Ile
305                 310                 315                 320

Asp Val Ala Gly Ser Ala Arg Leu Lys Ala Pro Gly Leu Gly Leu Ala
                325                 330                 335
```

<210> SEQ ID NO 47
<211> LENGTH: 337
<212> TYPE: PRT
<213> ORGANISM: Galerina marginata

<400> SEQUENCE: 47

```
Met Ser Thr Pro Pro Gln Thr Tyr Arg Leu Pro Arg Leu Asn Glu Thr
1               5                   10                  15
```

```
Phe Ser Val Phe Pro Ser Asn Gly Val Asn Pro His Phe Ser Glu Cys
             20                  25                  30

Arg Ala Gln Ser Arg Glu Trp Ala Ser Pro Tyr Tyr Thr Leu Val Phe
         35                  40                  45

Pro Pro Asp Val Arg Val Asp Leu Glu Asn Cys Asn Phe Glu Leu Val
 50                  55                  60

Ser Ala Tyr Ala Leu Pro Tyr Ala Asn Pro Asp Gly Leu Ser Ala Ser
 65                  70                  75                  80

Met Asp Cys Tyr Asn Leu Thr Trp Met Phe Asp Glu Val Thr Asp Arg
                 85                  90                  95

Leu Ser Gly Lys Ala Ala Glu Ala Ala Val Val Ser Arg Ala
             100                 105                 110

Leu Arg Asp Ile Asp Tyr Asp Asn Gly Thr Ala Leu Cys Arg Met Thr
             115                 120                 125

Arg Asp Tyr Arg Cys Asn His Ile Glu Lys Phe Gly Ser Asn Val Ala
 130                 135                 140

Arg Arg Phe Ile Ala Asn Phe Cys Gln Tyr Val Glu His Thr Ala Thr
145                 150                 155                 160

Glu Ala Met Leu Arg Glu Arg Asp Gln Val Leu Asp Ile Asn Gly Tyr
                 165                 170                 175

Ile Ser Leu Arg Arg Gly Ala Val Gly Gly Arg Ile Val Phe Asp Leu
             180                 185                 190

Val Glu Tyr Ala Leu Gly Leu Asp Leu Pro Gln Tyr Val His Glu Asp
             195                 200                 205

Pro Val Phe Ile Gly Ala Leu Asn Ala Gly Val Asp Leu Leu Ala Phe
 210                 215                 220

Thr Asn Asp Leu Phe Ser Tyr Asp Met Glu Gln Ala Lys Gly His Ser
225                 230                 235                 240

Ala Ala Asn Ile Ile Thr Val Val Met Lys Ser Lys Gly Thr Asp Leu
                 245                 250                 255

Gln Ser Ala Val Asp Phe Val Ala Gly Tyr Cys Glu Cys Leu Ile Arg
             260                 265                 270

Gln Leu Leu Asp Ala Lys Ala Val Phe Thr Ser His Thr Asp Pro Val
             275                 280                 285

Phe Ser Arg Asp Ala Ala Arg Trp Leu Asp Gly Val Gly Asp Trp Val
 290                 295                 300

Arg Gly Asn Glu Glu Trp Cys Phe Ala Thr Glu Arg Tyr Phe Gly Lys
305                 310                 315                 320

Gln Asn Lys Leu Val Asn Glu Thr Arg Ile Val Glu Leu Thr Lys Arg
                 325                 330                 335

Leu

<210> SEQ ID NO 48
<211> LENGTH: 344
<212> TYPE: PRT
<213> ORGANISM: Galerina marginata

<400> SEQUENCE: 48

Met Thr Thr Pro Gln Thr Phe Arg Leu Pro Arg Leu Ser Asp Thr Phe
1               5                   10                  15

Ser Val Phe Pro Asp Asn Gly Leu Asn Pro His Tyr Ser Glu Cys Arg
             20                  25                  30

Leu Gln Ser Lys Glu Trp Ala Ser Lys Tyr Tyr Lys Ala Val Cys Gly
         35                  40                  45
```

```
Pro Asn Met Thr Ala Tyr Leu Gly Asp Cys Asn Phe Glu Leu Leu Ala
    50                  55                  60

Ala Tyr Ala Tyr Pro Tyr Ala Lys Pro Glu Gly Ile Ile Lys Val Met
 65                  70                  75                  80

Asp Tyr Tyr Asn Ile Thr Trp Ile Phe Asp Glu Phe Thr Asp Thr Leu
                 85                  90                  95

Pro Gly Lys Glu Ala Glu Ala Ala Ala Ile Val Ser Arg Thr Leu
            100                 105                 110

Arg Asn Arg Asp Tyr Asp Gly Ser Trp Leu Cys Gln Ile Met Thr
            115                 120                 125

Asp Tyr Arg Arg Asn His Ile Asp Lys Leu Gly Pro Asn Val Ala Arg
    130                 135                 140

Arg Phe Val Glu His Phe Cys Asn Tyr Val Glu Gly Thr Gly Thr Glu
145                 150                 155                 160

Ala Glu Leu Arg Glu Lys Asn Gln Val Leu Asp Ile Ser Gly Tyr Ile
                165                 170                 175

Ala Met Arg Arg Glu Ala Val Ala Ala Gln Val Ala Phe Asp Leu Val
            180                 185                 190

Glu Asp Cys Leu Gly Leu Asp Leu Pro Gln Tyr Val His Glu Asp Pro
            195                 200                 205

Ala Phe Val Ser Gly Tyr Met Ala Gly Val Asp Leu Ile Ala Leu Asn
210                 215                 220

Asn Asp Met Val Ser Tyr Asn Met Glu Gln Ser Lys Gly His Gly Gly
225                 230                 235                 240

Ala Asn Ile Val Thr Val Val Met Asn Ser Lys Gly Ile Gly Leu Gln
                245                 250                 255

Ser Ala Met Asp Phe Val His Gly Tyr Cys Glu Cys Ile Thr Gln Gln
            260                 265                 270

Leu Leu Asn Ala Arg Ile Ser Leu Leu Ser Arg Pro Asp Pro Val Phe
            275                 280                 285

Ser Arg Asp Ala Thr Arg Cys Leu Glu Ala Phe Gly Asp Trp Ile Arg
290                 295                 300

Gly Tyr Asp Glu Trp Asn Phe Ala Ile Glu Arg Tyr Phe Gly Lys Gln
305                 310                 315                 320

Thr Lys Leu Val Gln Glu Lys Arg Ile Val Glu Leu Met Arg Pro Phe
                325                 330                 335

Gln Gly Phe Met Ala Leu Lys Asp
            340

<210> SEQ ID NO 49
<211> LENGTH: 344
<212> TYPE: PRT
<213> ORGANISM: Galerina marginata

<400> SEQUENCE: 49

Met Thr Thr Ser Leu Thr Phe Arg Leu Pro Arg Leu Asp Asp Thr Phe
 1               5                  10                  15

Ala Val Phe Pro Asp Lys Gly Val Asn Pro His Phe Ser Glu Cys Arg
                20                  25                  30

Arg Gln Ser Arg Glu Trp Val Asp Lys Tyr Thr Glu Ile Ala Phe Gly
            35                  40                  45

Pro Lys Met Cys Ala Phe Leu Arg Asn Cys Asn Leu Glu Leu Val Ala
    50                  55                  60

Ala Tyr Ala Tyr Pro Asp Ala Lys Pro Asp Gly Leu Arg Ala Ala Met
 65                  70                  75                  80
```

Asp Tyr Leu Asn Ile Ala Trp Val Phe Asp Glu Phe Thr Asp Asp Leu
            85                  90                  95

Ser Gly Lys Glu Ala Ile Gln Ala Ala Val Ala Thr Arg Thr Leu
           100                 105                 110

Arg Asp Arg Asp Phe Asp Asp Gly Ser Trp Val Cys His Ile Leu Thr
115                 120                 125

Asp Tyr Arg Leu Asn His Ile Asp Lys Phe Gly Ser Asn Val Ala Leu
130                 135                 140

Arg Phe Ile Asp His Leu Cys Gln Ser Phe Gly Gln Thr Gly Ala Glu
145                 150                 155                 160

Ala Glu Leu Arg Glu Lys Asn Gln Val Leu Asn Leu Asp Ser Tyr Ile
                165                 170                 175

Ser Leu Arg Arg Ser Thr Val Ala Val Arg Val Phe Asp Leu Val
            180                 185                 190

Glu Tyr Cys Leu Gly Leu Asn Leu Pro Gln Tyr Val His Glu Asp Pro
            195                 200                 205

Val Phe Ile Ser Ala Tyr Leu Ala Ala Val Asp Val Ile Ala Trp Thr
210                 215                 220

Asn Asp Leu Ala Ser Tyr Asp Met Glu Gln Ala Lys Gly His Ser Gly
225                 230                 235                 240

Ala Asn Ile Val Thr Val Met Lys Ser Lys Gly Ile Asn Leu Gln
                245                 250                 255

Ser Ala Val Asp Phe Ile Ala Gly Tyr Cys Glu Cys Leu Thr Gln Gln
            260                 265                 270

Phe Ile Cys Ala Lys Ala Asp Leu Ala Ser Arg Thr Asp Pro Val Phe
            275                 280                 285

Ser Lys Asp Ser Val Arg Cys Leu Asp Ala Phe Gly Asp Trp Val Arg
290                 295                 300

Gly Asn Asp Glu Trp Asn Phe Val Thr Glu Arg Tyr Phe Gly Gln Arg
305                 310                 315                 320

Asn Thr Leu Val Lys Glu Thr Arg Val Val Glu Leu Arg Lys Pro Phe
                325                 330                 335

Glu Asp Val Val Leu Ser Thr Glu
            340

<210> SEQ ID NO 50
<211> LENGTH: 345
<212> TYPE: PRT
<213> ORGANISM: Galerina marginata

<400> SEQUENCE: 50

Met Asn Thr Thr Thr Arg Thr Phe Tyr Leu Pro Arg Leu Glu Asp Thr
1               5                   10                  15

Phe Ser Val Phe Pro Asp Asn Gly Leu Asn Pro His Tyr Ala Glu Cys
            20                  25                  30

Arg Ile Gln Ser Gln Ala Trp Ile Asp Lys Tyr Lys Ile Val Cys
        35                  40                  45

Gly Pro Lys Met Arg Ala Tyr Met Asp His Cys Lys Phe Glu Leu Ile
    50                  55                  60

Thr Ala Tyr Thr Tyr Pro Tyr Ala Ser Ser Asp Gly Leu Arg Lys Thr
65                  70                  75                  80

Met Asp Leu Ala Asn Ile Leu Trp Leu Tyr Asp Glu Phe Thr Asp Thr
                85                  90                  95

Leu Ser Gly Lys Asp Ala Thr Asn Ala Ala Ala Ile Val Ile Arg Thr

```
            100                 105                 110
Leu Arg Glu Arg Asp Phe Asp Asp Gly Ser Trp Ile Cys His Met Met
            115                 120                 125

Arg Asp Phe Tyr Ala Ala His Ile Glu Lys Phe Gly Pro Asn Val Ser
            130                 135                 140

Arg Arg Phe Ile Asp His Phe Cys Gln Tyr Val Glu Gly Thr Gly Thr
145                 150                 155                 160

Glu Ala Lys His Arg Glu Lys Asp His Val Leu Asp Ile Asn Ala Tyr
                165                 170                 175

Ile Ile Met Arg Arg Ala Ala Ser Ala Val Leu Thr Ala Phe Asp Leu
            180                 185                 190

Ala Glu Tyr Cys Leu Gly Ile Asp Leu Pro Gln Tyr Val His Asp Asp
            195                 200                 205

Pro Ala Phe Ile Ser Gly Tyr Asn Ala Gly Leu Asp Leu Val Phe Leu
            210                 215                 220

Asp Asn Asp Leu Phe Ser Tyr Asp Met Glu Gln Ala Lys Gly His Cys
225                 230                 235                 240

Thr Thr Asn Ile Ile Thr Val Val Met Lys Ser Lys Arg Ile Asp Leu
                245                 250                 255

Gln Ser Ala Phe Asp Phe Thr Ala Gly Tyr Cys Glu Ser Leu Thr Gln
            260                 265                 270

Gln Leu Ile Ala Ala Gln Ile Ser Leu Ala Ser Arg Thr Asp Pro Val
            275                 280                 285

Phe Ser Asn Asn Ala Val Lys Cys Leu Glu Ala Ile Ala Asn Trp Val
            290                 295                 300

Lys Gly Ser Asp Gly Trp Ser Phe Ala Thr Glu Arg Tyr Phe Gly Lys
305                 310                 315                 320

Gln Asn Val Ile Val Lys Glu Thr Arg Ala Val Glu Met Arg Lys Ser
                325                 330                 335

Phe Gln Asp Ile Ala Val Leu Lys Glu
            340                 345

<210> SEQ ID NO 51
<211> LENGTH: 345
<212> TYPE: PRT
<213> ORGANISM: Piloderma croceum

<400> SEQUENCE: 51

Met Pro Ser Gln Ser Leu Thr Ile Arg Leu Pro Lys Phe Glu Glu Thr
1               5                   10                  15

Phe Ser Val Phe Pro Asp Asn Gly Leu Asn Pro His Tyr Ala Asn Ser
            20                  25                  30

Arg Ala Glu Ser Arg Ala Trp Ile Asn Gln Tyr His His Ala Val Cys
            35                  40                  45

Gly Pro Asn Met Arg Thr Phe Met Asp Lys Cys Asn Phe Glu Leu Ala
        50                  55                  60

Gly Ala Leu Phe Tyr Pro Tyr Ala Asn Glu Ala Gly Leu Arg Ala Thr
65                  70                  75                  80

Met Asp Leu Ala Asn Leu Leu Trp Leu Tyr Asp Glu Leu Thr Asp Thr
                85                  90                  95

Lys Thr Glu Ala Glu Ala Val Asn Ala Ala Gln Ile Val Thr Cys Ala
            100                 105                 110

Leu Arg Glu Pro Asp Phe Asp Asn Gly Thr Trp Ile Cys Ser Met Ile
            115                 120                 125
```

```
Lys Asp Phe Asn Gln Arg His Ile Ser Lys Ala Gly Pro Asn Thr Ala
            130                 135                 140

Tyr Arg Phe Ile Tyr Asn Phe Cys Asn Tyr Val Glu Ala Val Gly Thr
145                 150                 155                 160

Glu Ala Gly Leu Arg Ala Lys Asn Glu Ile Leu Asp Ile Thr Thr Tyr
                165                 170                 175

Ile Ser Phe Arg Arg Glu Thr Ser Ala Leu Arg Leu Thr Phe Asp Leu
            180                 185                 190

Val Gln Tyr Cys Leu Gly Ile Asp Leu Pro Gln Tyr Val His Asp Asp
                195                 200                 205

Pro Val Phe Ala Ser Gly Tyr Asn Ala Ala Met Asp Leu Val Cys Trp
    210                 215                 220

Thr Asn Asp Leu Phe Ser Tyr Asn Arg Glu Gln Ala Lys Gly His Ala
225                 230                 235                 240

Gly Ala Asn Val Val Thr Val Ile Met Lys Ser Lys Gly Val Asp Ile
                245                 250                 255

Gln Ser Ala Val Asp Phe Val Gly Gly Tyr Cys Glu Ala Leu Thr Ser
            260                 265                 270

Gln Leu Val Glu Ala Arg Arg Ile Leu Leu Phe Arg Ser His Arg Val
    275                 280                 285

Tyr Ser Lys Asp Ala Val Arg Ile Leu Glu Ala Phe Gly Asp Phe Val
    290                 295                 300

Arg Gly Asn Asp Gln Trp Ser Phe Ala Ser Glu Arg Tyr Phe Gly Gln
305                 310                 315                 320

Lys Asn Lys Val Val Lys Glu Thr Arg Ile Val Glu Ile Met Thr Pro
                325                 330                 335

Phe Ser Asp Leu Ile Ala Ile Asn Glu
            340                 345

<210> SEQ ID NO 52
<211> LENGTH: 345
<212> TYPE: PRT
<213> ORGANISM: Piloderma croceum

<400> SEQUENCE: 52

Met Pro Ser Gln Ser Leu Thr Ile Arg Leu Pro Lys Phe Glu Glu Thr
1               5                   10                  15

Phe Ser Val Phe Pro Asp Asn Gly Leu Asn Pro His Tyr Ala Asn Ser
                20                  25                  30

Arg Ala Glu Ser Arg Ala Trp Ile Asn Gln Tyr His His Ala Val Cys
            35                  40                  45

Gly Pro Asn Met Arg Thr Phe Met Asp Lys Cys Asn Phe Glu Leu Ala
    50                  55                  60

Gly Ala Leu Phe Tyr Pro Tyr Ala Asn Glu Ala Gly Leu Arg Ala Thr
65                  70                  75                  80

Met Asp Leu Val Asn Leu Leu Trp Leu Tyr Asp Glu Leu Thr Asp Thr
                85                  90                  95

Lys Thr Glu Thr Glu Ala Val Asn Ala Ala His Ile Val Ala Cys Ala
                100                 105                 110

Leu Arg Glu Pro Asp Phe Asp Asp Gly Thr Trp Ile Cys Ser Met Ile
            115                 120                 125

Lys Asp Phe Asn Gln Arg His Ile Ser Lys Ala Gly Pro Asn Thr Ala
            130                 135                 140

Tyr Arg Phe Ile Tyr Asn Phe Cys Asn Tyr Val Glu Ala Val Gly Thr
145                 150                 155                 160
```

```
Glu Ala Gly Leu Arg Ala Lys Asn Glu Ile Leu Asp Ile Thr Thr Tyr
                165                 170                 175

Ile Ser Phe Arg Arg Glu Thr Ser Ala Leu Arg Leu Thr Phe Asp Leu
                180                 185                 190

Val Gln Tyr Cys Leu Gly Ile Asp Leu Pro Gln Tyr Val His Asp Asp
                195                 200                 205

Pro Val Phe Ala Ser Gly Tyr Asn Ala Ala Met Asp Leu Val Cys Trp
210                 215                 220

Thr Asn Asp Leu Phe Ser Tyr Asn Arg Glu Gln Ala Lys Gly His Ala
225                 230                 235                 240

Gly Ala Asn Val Val Thr Val Ile Met Lys Ser Lys Gly Val Asp Ile
                245                 250                 255

Gln Ser Ala Val Asp Phe Val Gly Gly Tyr Cys Glu Ala Leu Thr Ser
                260                 265                 270

Gln Leu Val Glu Ala Arg Arg Ile Leu Leu Ser Arg Ser His Arg Val
                275                 280                 285

Tyr Ser Lys Asp Ala Val Arg Ile Leu Glu Ala Phe Gly Asp Phe Val
                290                 295                 300

Arg Gly Asn Asp Gln Trp Ser Phe Ala Ser Glu Arg Tyr Phe Gly Gln
305                 310                 315                 320

Lys Asn Lys Val Val Lys Glu Ser Arg Ile Val Glu Ile Ile Thr Pro
                325                 330                 335

Phe Ser Asp Leu Ile Ala Ile Asn Glu
                340                 345

<210> SEQ ID NO 53
<211> LENGTH: 347
<212> TYPE: PRT
<213> ORGANISM: Sphaerobolus stellatus

<400> SEQUENCE: 53

Met Pro Leu Leu Ser Cys Ser Gln Thr Phe Arg Leu Pro Pro Leu His
1               5                   10                  15

Glu Thr Phe Ser Val Phe Pro Asp Asn Gly Leu Asn Pro Asn Tyr Asn
                20                  25                  30

Ala Cys Arg Ala Gln Ser Arg Ala Trp Ile Ser Lys Tyr Asn Val Gln
                35                  40                  45

Val Cys Gly Pro Lys Met Arg Ala Phe Met Asp Asn Cys Asn Phe Glu
            50                  55                  60

Leu Ser Asn Ala Tyr Val Tyr Pro Tyr Ala Gln Pro Ala Gly Leu Arg
65                  70                  75                  80

Ala Thr Met Asp Leu Ala Asn Ile Leu Trp Leu Tyr Asp Glu Tyr Thr
                85                  90                  95

Asp Met Gln Thr Gly Glu Asp Ala Ala Lys Ala Val Thr Val Ser
                100                 105                 110

Lys Thr Leu Leu Asn Pro Glu Tyr Asp Asp Thr Trp Ile Cys His
            115                 120                 125

Met Met Arg Asp Phe Tyr Val Asn His Ile Gln Lys Cys Arg Pro Asn
                130                 135                 140

Val Ala His Arg Phe Ile Glu Asn Phe Cys Arg Tyr Thr Glu Val Val
145                 150                 155                 160

Gly Thr Glu Ala Lys Leu Arg Glu Lys Asn Glu Val Leu Asp Ile Pro
                165                 170                 175

Gly Tyr Val Ala Leu Arg Arg Glu Ile Ser Ala Val Arg Thr Cys Phe
```

```
             180                 185                 190
Asp Leu Val Glu Tyr Cys Leu Asp Leu Asp Phe Pro Asp Tyr Val His
            195                 200                 205

Lys Asp Pro Ile Phe Val Ile Gly Tyr Asn Ala Ala Met Asp Leu Val
210                 215                 220

Phe Trp Ala Asn Asp Leu Phe Ser Tyr Asn Ser Glu Gln Ala Lys Gly
225                 230                 235                 240

His Ala Ala Ala Asn Val Val Thr Val Ile Met Thr Ser Lys Lys Met
                245                 250                 255

Asn Leu Gln Ser Thr Val Asp Phe Ile Ala Gly Phe Cys Glu Ala Leu
            260                 265                 270

Thr Phe Gln Leu Leu Asp Ala Lys Arg Ala Leu Ser Leu His Glu Asp
        275                 280                 285

Pro Thr Phe Ser Arg Asp Ala Val Arg Cys Leu Glu Ala Phe Gly Asp
    290                 295                 300

Trp Val Arg Gly Asn Asp Ala Trp Ser Phe Ala Thr Thr Arg Tyr Phe
305                 310                 315                 320

Gly Pro Glu Asn Lys Ile Val Lys Glu Thr Arg Ile Val Lys Leu Lys
                325                 330                 335

Ala Pro Val Glu Glu Ser Val Ala Leu Lys Glu
            340                 345

<210> SEQ ID NO 54
<211> LENGTH: 348
<212> TYPE: PRT
<213> ORGANISM: Dendrothele bispora

<400> SEQUENCE: 54

Met Ala Ser Lys Ser Pro Ser Pro Arg Thr Phe Tyr Leu Pro Arg Leu
1               5                   10                  15

Glu Asp Thr Phe Ser Val Phe Pro Asp Asn Gly Leu Asn Pro Asn Phe
            20                  25                  30

Ala Ala Val Arg Pro Glu Ser Arg Ala Trp Ile Asn Gln Tyr Thr Lys
        35                  40                  45

Leu Val Cys Gly Pro Lys Met Cys Ala Phe Met Asp Asn Cys Asn Phe
    50                  55                  60

Glu Leu Ser Asn Ala Tyr Cys Tyr Pro Tyr Ala Glu Lys Pro Gly Leu
65                  70                  75                  80

Arg Ala Ser Met Asp Leu Ala Asn Ile Leu Trp Leu Tyr Asp Glu Phe
                85                  90                  95

Thr Asp Thr Glu Ser Gly Ala Glu Ala Gln Arg Ala Ala Ile Ile Val
            100                 105                 110

His Arg Thr Leu Arg Glu Pro Asp Phe Asp Asp Gly Ser Trp Ile Cys
        115                 120                 125

His Met Met Arg Asp Phe Arg Ile His His Val Asn Lys Ala Gly Pro
    130                 135                 140

Asn Val Ala Arg Arg Phe Ile Asp Asn Phe Cys Ser Tyr Val Glu Val
145                 150                 155                 160

Val Gly Thr Glu Ala Ile Leu Arg Glu Arg Lys Gln Val Leu Asp Ile
                165                 170                 175

Pro Gly Tyr Val Lys Phe Arg Arg Glu Thr Ser Ala Val Arg Ala Cys
            180                 185                 190

Phe Asp Leu Val Glu Tyr Ser Leu Gly Ile Asp Leu Pro Gln His Val
        195                 200                 205
```

-continued

His Asp Asp Pro Val Phe Ile Ser Gly Tyr Asn Ala Ala Met Asp Leu
210                 215                 220

Val Phe Trp Ala Asn Asp Leu Phe Ser Tyr Asn Met Glu Gln Ala Lys
225                 230                 235                 240

Gly His Gly Gly Ala Asn Val Val Thr Val Ile Met Lys Ser Lys Gly
                245                 250                 255

Met Asp Ile Gln Ser Thr Val Asn Phe Leu Ala Gly Tyr Cys Glu Ala
            260                 265                 270

Leu Thr Ala Gln Leu Leu Glu Ser Arg Arg Ile Leu Ala Ser Arg Pro
        275                 280                 285

Asp Pro Val Phe Asn Lys Asp Ala Val Arg Val Ile Asp Ala Phe Gly
290                 295                 300

Asp Trp Val Arg Gly Asn Asp Gln Trp Ser Phe Ala Thr Glu Arg Tyr
305                 310                 315                 320

Phe Gly Lys Asp Asn Glu Thr Ile Lys Lys Thr Arg Ile Val Glu Ile
                325                 330                 335

Lys Glu Pro Phe Met Asp Ser Leu Ala Leu Asn Glu
            340                 345

<210> SEQ ID NO 55
<211> LENGTH: 349
<212> TYPE: PRT
<213> ORGANISM: Moniliophthora roreri

<400> SEQUENCE: 55

Met Ala Arg Ile Ile Val Ile Pro Asp Phe Glu Ser Met Cys Ser Val
1               5                   10                  15

Leu Pro Asn Gly Gly Val Asn Pro His His Asp Glu Ala Phe Thr Glu
                20                  25                  30

Ala Arg Cys Trp Ile Ala Gln Tyr His Asn Ser Asp Phe Gly Pro Asn
            35                  40                  45

Met Thr Ala Phe Met Glu Ser Cys Lys Phe Glu Leu Ala Gly Ser Tyr
        50                  55                  60

Thr Tyr Pro His Leu Asp Lys Tyr Gly Leu Arg Ala Thr Met Asp Trp
65                  70                  75                  80

Leu Asn Ile Leu Trp Phe Phe Asp Glu Val Thr Asp Thr Glu Thr Gly
                85                  90                  95

Lys Asp Ala Arg Arg Ser Ala Asp Ile Val Cys His Thr Leu Arg Asp
            100                 105                 110

Ser Glu Tyr Asn Asp Gly Thr Ser Leu Cys Arg Met Ile Thr Asp Phe
        115                 120                 125

Arg Ile Asp His Leu Ser Arg Ala Gly Pro Glu Thr Thr Arg Arg Phe
130                 135                 140

Leu Asn His Cys Asp Asp Met Phe Ser Ala Val Ala Arg Glu Ala Gly
145                 150                 155                 160

Phe Arg Glu Gln Gly Thr Val Leu Ser Val Glu Glu Tyr Leu Val His
                165                 170                 175

Arg Lys Glu Thr Ser Gly Val Arg Val Cys Tyr Asp Met Ala Glu Phe
            180                 185                 190

Cys Ile Gly Ile Asp Leu Pro Gly Ala Ile Tyr Asp Met Glu Asp Phe
        195                 200                 205

Arg Lys Gly Tyr Glu Ala Ser Leu Asp Phe Val Cys Leu Ser Asn Asp
210                 215                 220

Leu Phe Ser Tyr Asn Ala Glu Gln Ser Lys Gly His Ser Gly Phe Asn
225                 230                 235                 240

```
Ile Leu Thr Val Leu Ile Lys Ala Lys Ser Ile Glu Leu Gln Glu Ala
                245                 250                 255

Ala Asp Tyr Val Gly Ser Leu Cys Thr Asn Leu Leu Thr Glu Phe Arg
            260                 265                 270

Glu Ser Gln Gln Val Ile Glu Glu Cys Ala Arg Thr Ala Lys Asp Glu
        275                 280                 285

Ala Ser Ala Asn Thr Phe Arg Asp Ala Leu Cys Val Leu Glu Ala Tyr
    290                 295                 300

Gly His Trp Val Arg Gly Ile Glu Trp Ser Phe Glu Ser Glu Arg
305                 310                 315                 320

Tyr Phe Gly Lys Glu Asn Lys Met Val Arg Lys Ser Leu Thr Val Val
                325                 330                 335

Leu Ser Gln Ala Asp Ser Val Ser Arg Pro Leu His Ser
            340                 345

<210> SEQ ID NO 56
<211> LENGTH: 352
<212> TYPE: PRT
<213> ORGANISM: Moniliophthora roreri

<400> SEQUENCE: 56

Met Val Tyr Thr Ser Ser Pro Ser Phe Thr Leu Pro Asp Leu Glu Gly
1               5                   10                  15

Met Phe Ser Ile Leu Pro Asn Trp Gly Arg Asn Pro Tyr His Glu Ala
                20                  25                  30

Ala Arg Glu Glu Ser Arg Arg Trp Phe Ala Glu Tyr Thr Glu Thr Thr
            35                  40                  45

Phe Gly Pro Lys Met Thr Ala Phe Phe Glu Asn Cys Glu Phe Glu Leu
        50                  55                  60

Cys Met Ser Tyr Cys Tyr Pro Gln Leu Asp Tyr Glu Gly Leu Arg Ala
65                  70                  75                  80

Val Val Asp Trp Ala Asn Ile Leu Trp Tyr Leu Asp Glu Leu Thr Asp
                85                  90                  95

Thr Glu Thr Gly Lys Asp Ala Gly Gln Thr Ala Glu Ile Val Cys Arg
                100                 105                 110

Thr Leu Arg Asp Pro Cys Tyr Asn Asp Gly Thr Ser Leu Cys Arg Met
            115                 120                 125

Ile Thr Asp Phe Arg Val Asn His Leu Ser Arg Ala Gly Pro Glu Thr
        130                 135                 140

Thr Arg Arg Phe Ile Glu His Cys Arg Lys Thr Phe Phe Ala Phe Ser
145                 150                 155                 160

Asp Glu Ala Glu Leu Arg Ala Arg Arg Val Ile Leu Ser Ile Asn Asp
                165                 170                 175

Tyr Leu Thr Leu Arg Arg Glu Asn Gly Ser Val Arg Asn Cys Phe Asp
            180                 185                 190

Leu Ala Glu Cys Phe Met Gly Leu Asp Leu Pro Glu Ser Val Tyr Arg
        195                 200                 205

Leu Pro Asp Phe Arg Lys Ala Tyr Glu Ala Ala Val Asp Leu Val Cys
    210                 215                 220

Leu Thr Asn Asp Val Tyr Ser Tyr Asn Ala Glu Gln Ala Arg Gly Tyr
225                 230                 235                 240

Pro Ser Ser Asn Ile Met Thr Val Val Met Lys Glu Lys Gly Leu Gly
                245                 250                 255

Leu Gln Glu Ala Ser Asp Tyr Val Gly Ser Leu Cys Arg Lys Leu Phe
```

```
                    260                 265                 270
Asp Ile Phe Gln Ala Ser Gln Arg Glu Ile Gln Lys Leu Ala Tyr Asn
                275                 280                 285

Thr Asp Gly Ala Ser Val Asn Val Leu Arg Asp Ala Leu Arg Gly Leu
            290                 295                 300

Glu Ala Tyr Gly His Trp Val Arg Gly Asn Ala Glu Trp Ser Phe Glu
305                 310                 315                 320

Thr Glu Arg Tyr Phe Gly Arg Asp Lys Lys Ile Gln Ser Ser Leu
                325                 330                 335

Val Val Val Leu Trp Pro Ala Asn Ser Val Ser Arg Ser Leu Glu Gln
            340                 345                 350

<210> SEQ ID NO 57
<211> LENGTH: 389
<212> TYPE: PRT
<213> ORGANISM: Agrocybe aegerita

<400> SEQUENCE: 57

Met Val Trp Asp Phe Val Leu Ser Leu Phe His Ser Leu Leu Ala Ala
1               5                   10                  15

Phe Gln Thr Leu Thr Ser Trp Leu Thr Gly Ser Phe Leu Phe Asn Asn
            20                  25                  30

Lys Met Ala Pro Ala Pro Asn Pro Ala Pro Val Thr Phe Ile Leu Pro
        35                  40                  45

Asp Leu Glu Lys Thr Phe Asn Ser Leu Pro Asp Gly Leu Asn Pro
    50                  55                  60

His His Asp Val Ala Cys Ala Glu Ser Arg Glu Trp Phe Ala Lys Tyr
65                  70                  75                  80

Asn Lys Lys Val Leu Gly Ala Gln Met Gln Glu Phe Phe Arg Arg Cys
                85                  90                  95

Lys Phe Glu Leu Ile Thr Ser Tyr Thr Tyr Pro Tyr Val Asp Lys Glu
            100                 105                 110

Gly Leu Arg Ala Thr Met Asp Trp His Asn Ile Leu Trp Phe Phe Asp
        115                 120                 125

Glu Val Thr Asp Thr Glu Thr Gly Lys Asp Ala His Lys Ser Ala Ile
    130                 135                 140

Ile Thr Ile Arg Thr Leu Arg Glu Pro Asp Phe Asp Asp Gly Ser Ser
145                 150                 155                 160

Leu Cys Arg Met Val Arg Asp Phe Arg Leu Ser His Leu Ser Arg Ala
                165                 170                 175

Gly Pro Glu Cys Thr Arg Arg Phe Leu Glu His Cys Asp Val Ala Phe
            180                 185                 190

His Ala Gly Ala Val Glu Ala Glu Leu Arg Glu Lys Gly Glu Val Leu
        195                 200                 205

Ser Ile Glu Gly Tyr Leu Lys Leu Arg Arg Glu Thr Ser Gly Ala Arg
    210                 215                 220

Thr Cys Phe Asp Met Ala Glu Tyr Leu Met Asp Ile Asp Leu Pro Gln
225                 230                 235                 240

Asp Met Tyr Asp Asp Pro Val Phe Gln Lys Gly Tyr Ile Ala Ala Leu
                245                 250                 255

Asp Leu Ile Phe Leu Ala Asn Asp Leu Tyr Ser Tyr Asn Met Glu Gln
            260                 265                 270

Ala Lys Gly His Asn Gly Ala Asn Val Leu Thr Val Val Met Lys Glu
        275                 280                 285
```

```
Thr Lys Leu Asn Leu Gln Ser Ala Ala Asp Tyr Val Gly Val Leu Cys
    290                 295                 300
Glu Lys Leu Ile Lys Gln Phe Gln Glu Ala Lys Ser Thr Leu Glu Asn
305                 310                 315                 320
Arg Leu Ala Lys Glu Lys Asn Pro Ala Lys Ala Ala Leu Lys Asp
                325                 330                 335
Ala Ile Arg Ser Leu Val Gly Tyr Gly His Trp Val Arg Gly Asn Val
            340                 345                 350
Glu Trp Ser Phe Glu Thr Glu Arg Tyr Phe Gly Lys Lys Asn Lys Glu
        355                 360                 365
Ile Lys Lys Ser Arg Val Val Thr Leu Thr Pro Thr Asn Ser Val Asn
    370                 375                 380
Arg Ala Leu Lys Ala
385

<210> SEQ ID NO 58
<211> LENGTH: 50
<212> TYPE: DNA
<213> ORGANISM: Artificial Sequence
<220> FEATURE:
<223> OTHER INFORMATION: Upstream sequence

<400> SEQUENCE: 58
aacaggagga attaaccacg acggaagcgt caaagcacac taaatagact                50

<210> SEQ ID NO 59
<211> LENGTH: 50
<212> TYPE: DNA
<213> ORGANISM: Artificial Sequence
<220> FEATURE:
<223> OTHER INFORMATION: Upstream sequence

<400> SEQUENCE: 59
actatagggg aattgtgagc ggataacaat tcccctccac taaatagact                50

<210> SEQ ID NO 60
<211> LENGTH: 15
<212> TYPE: DNA
<213> ORGANISM: Artificial Sequence
<220> FEATURE:
<223> OTHER INFORMATION: RBS sequence
<220> FEATURE:
<221> NAME/KEY: misc_feature
<222> LOCATION: (1)..(1)
<223> OTHER INFORMATION: w is a or t
<220> FEATURE:
<221> NAME/KEY: misc_feature
<222> LOCATION: (2)..(2)
<223> OTHER INFORMATION: d is a, g or t

<400> SEQUENCE: 60
wdgaagaggc ctaaa                                                      15

<210> SEQ ID NO 61
<211> LENGTH: 15
<212> TYPE: DNA
<213> ORGANISM: Artificial Sequence
<220> FEATURE:
<223> OTHER INFORMATION: RBS sequence
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (2)..(2)
```

```
<223> OTHER INFORMATION: k is g or t
<220> FEATURE:
<221> NAME/KEY: misc_feature
<222> LOCATION: (5)..(5)
<223> OTHER INFORMATION: r is a or g

<400> SEQUENCE: 61
nkaargaggt ataaa                                                    15

<210> SEQ ID NO 62
<211> LENGTH: 1311
<212> TYPE: DNA
<213> ORGANISM: Artificial Sequence
<220> FEATURE:
<223> OTHER INFORMATION: Codon optimized VS sequence with N-terminal
      6-histidine tag

<400> SEQUENCE: 62
atgcatcacc atcaccatca cgctagctcc ctgctggaac cgtctctggc tgcaatcgcg    60
ctggtgatcc tgctggcgag cgtgagcctg agccgcaaaa aacgccctgc cgccccggaa   120
ccgcaaggct tgtcagttct gggcaacctg ttcgacattc cgaaacgggc ttccagcatc   180
atttacctgg ctctgggcaa accgtacaac actctgacca gcgcgcggt gtcgcagctg    240 caaggttata ctccgggctc tcacatcgat gcaacgagcc atagcccgcg cgttttcgc    300 ctgcccaacc tggaagaaac cttctccgtc ttccggacc acggtctgaa cccgaactat    360
accagcgctc gtactgatag ccgcgcttgg atcaaccagt acaccaaggt tgtttgcggt    420
ccgaaaatgg tcgcatttat gaacaactgt gaatttgaac tgtcgaattc acactgctac    480
ccgtacgccg gttacaaagg tctgaaagct accatggacc ttaccaacat tctgtggttg    540
tatgatgaat ataccgacac tggttccggt gctgaagcgg taaaggcagc cggtatcgtt    600
gctcgcgccc tgcgcgaacc agattacgat gatgggacct gggtttgccg tatgatgaag    660
tccttcaaac aaaaccacat cgacaaagct ggtccgggtg tcgcgcgtcg ttttattgac    720
aacttctgca actatgtaga agtggtgggt cgcgaagctg aactgcgcga gaaaaacgaa    780
gttctggata tccccaacta cgtaactttc cgtcgtgaaa cctcagcagt ccgcacctgt    840
tttgatctgg ttgaatattg cctggatctg gacctgcctc aatacgttca tgatgacccg    900 gttttattt ccggctacaa tgctggcatg gacctggtct tttgggcgaa cgacttggtt    960
tcttacaaca tggaacagtc taagggccat tccggcgcta cgttgttac tgtcatcatg   1020 aagagcaaag gtgttgacct gcagaccgcc gtagactttc tgggcggcta ctgtgaggca   1080
ctcactgccc agctgctgga agctaaacgc attctccagg cgcgtagcga tgcggcctac   1140
tctcgcgatg ttgttcgtct gatggatgcg ttcggtgatt gggtacgcgg caatgtggct   1200
tggtcttttg aaaccgaacg ctatttcggt aaagaaaaca aacgcgttaa agaaaccctg   1260
ctggtggagc tgaaggaacc gttcgtaggt gcgctggcct aaaagaata a             1311

<210> SEQ ID NO 63
<211> LENGTH: 1059
<212> TYPE: DNA
<213> ORGANISM: Artificial Sequence
<220> FEATURE:
<223> OTHER INFORMATION: Truncated VS (del2-85) sequence with N-terminal
      6-histidine tag

<400> SEQUENCE: 63
atgcatcacc atcaccatca cacgagccat agcccgcgcg ttttcgcct gcccaacctg     60 gaagaaacct tctccgtctt cccggaccac ggtctgaacc cgaactatac cagcgctcgt   120
```

```
actgatagcc gcgcttggat caaccagtac accaaggttg tttgcggtcc gaaaatggtc      180
gcatttatga acaactgtga atttgaactg tcgaattcac actgctaccc gtacgccggt      240
tacaaaggtc tgaaagctac catggacctt accaacattc tgtggttgta tgatgaatat      300
accgacactg gttccggtgc tgaagcggta aaggcagccg gtatcgttgc tcgcgccctg      360
cgcgaaccag attacgatga tgggacctgg gtttgccgta tgatgaagtc cttcaaacaa      420
aaccacatcg acaaagctgg tccgggtgtc gcgcgtcgtt ttattgacaa cttctgcaac      480
tatgtagaag tggtgggtcg cgaagctgaa ctgcgcgaga aaaacgaagt tctggatatc      540
cccaactacg taactttccg tcgtgaaacc tcagcagtcc gcacctgttt tgatctggtt      600
gaatattgcc tggatctgga cctgcctcaa tacgttcatg atgaccggt tttatttcc        660 ggctacaatg ctggcatgga cctggtcttt tgggcgaacg acttggtttc ttacaacatg      720
gaacagtcta agggccattc cggcgctaac gttgttactg tcatcatgaa gagcaaaggt      780
gttgacctgc agaccgccgt agactttctg ggcggctact gtgaggcact cactgcccag      840
ctgctggaag ctaaacgcat tctccaggcg cgtagcgatg cggcctactc tcgcgatgtt      900
gttcgtctga tggatgcgtt cggtgattgg gtacgcggca atgtggcttg gtcttttgaa      960
accgaacgct atttcggtaa agaaaacaaa cgcgttaaag aaaccctgct ggtggagctg    1020
aaggaaccgt tcgtaggtgc gctggcctta aaagaataa                           1059
```

VIRIDIFLOROL PRODUCTION IN AUXOTROPHIC ESCHERICHIA COLI

CROSS-REFERENCE TO RELATED APPLICATIONS

This application claims the benefit of priority of Singapore application No. 10201907354Y, filed 8 Aug. 2019, the contents of it being hereby incorporated by reference in its entirety for all purposes.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "55746_Seqlisting.txt", which was created on Jul. 16, 2020 and is 78,138 bytes in size. The subject matter of the Sequence Listing is incorporated herein in its entirety by reference.

FIELD OF THE INVENTION

The invention is in the field of biotechnology. In particular, the invention relates to methods for the production of terpenoids and the optimization thereof.

BACKGROUND OF THE INVENTION

Terpenoids, also known as isoprenoids, have enormous regiochemical and stereochemical diversity, ranging from C5 (hemiterpenes) to C40 (tetraterpenes) to polyterpenes (such as natural rubber). The terpenoid diversity is attributed primarily to terpene synthases (TPSs), which convert acyclic prenyl diphosphate precursors into a multitude of cyclic and acyclic terpene scaffolds. In accordance with their structural diversity, the functions of terpenoids range from mediating symbiotic or antagonistic interactions between organisms to electron transfer, protein prenylation, or contribution to membrane fluidity. The structural and functional diversity of terpenoids has allowed terpenoids to be widely used in various applications including pharmaceuticals, nutraceuticals, agriculture, flavorings, fragrances and biofuels.

Terpenes and terpenoids are the primary constituents of the essential oils of many plants and the main contributors to the aroma of these essential oils. One terpenoid of particular interest is viridiflorol, a known fragrance molecule isolated from Niaouli (*Melaleuca quinquenervia*) essential oil. Due to its antibacterial, anti-inflammatory and antioxidant properties, viridiflorol is currently used in several cosmetics and personal care products. In addition, viridiflorol is a strong feeding deterrent for *melaleuca* leaf weevil and a potent inhibitor of bacterial biofilm formation. Therefore, viridiflorol can be potentially applied in the agriculture and food industries to replace current broad-spectrum toxic pesticides and unhealthy food preservatives. However, high cost of plant extracts and supply fluctuations due to political and weather conditions have limited the production and the use of viridiflorol. Chemical synthesis of viridiflorol has low enantioselectivity. The existence of 6 chiral centres, or 64 different stereoisomers, has posed a great challenge to the chemical synthesis of viridiflorol, resulting in low yields and ultra-high costs.

There is therefore a need to identify methods of viridiflorol synthesis that can produce higher yields.

SUMMARY

In one aspect, there is provided a method of increasing terpenoid production in a host cell that produces one or more terpenoids, comprising:
a) providing a host cell that produces one or more terpenoids, said host cell comprising a vector comprising a polynucleotide sequence encoding a terpene synthase enzyme;
b) modifying the vector to:
  i. introduce an inducible promoter operably linked to the polynucleotide sequence encoding the terpene synthase enzyme; and
  ii. introduce a polynucleotide sequence encoding a ribosomal binding site (RBS) that increases translation initiation rate of the terpenoid compared to a wild type ribosomal binding site;
c) determining the dosage of an inducer capable of inducing the inducible promoter;
d) culturing the host cell in a culture medium in the presence of the inducer at the dosage determined from step c); and
e) isolating the terpenoid from the culture medium.

In another aspect, there is provided a host cell comprising at least one vector, wherein said at least one vector comprises:
a) a polynucleotide sequence encoding one or more genes of the mevalonate pathway operably linked to an inducible promoter;
b) a polynucleotide sequence encoding a ispA gene;
c) a polynucleotide sequence encoding a terpene synthase enzyme operably linked to an inducible promoter; and
d) a polynucleotide sequence encoding a ribosomal binding site (RBS) that increases translation initiation rate of the terpene synthase enzyme compared to a wild type ribosomal binding site.

In another aspect, there is provided an *Escherichia coli* cell deficient in the genes aroA, aroB and aroC, comprising:
a. a first vector comprising:
  i. a polynucleotide sequence encoding a viridiflorol synthase enzyme operably linked to a TM1 promoter; wherein said viridiflorol synthase enzyme is mutated, and wherein said mutation is G227C, V314Y and deletion of amino acids at positions 2 to 85 of SEQ ID NO: 24;
  ii. a polynucleotide sequence encoding a RBS ribosomal binding site (RBS) that increases translation initiation rate of the terpenoid compared to a wild type ribosomal binding site, said polynucleotide sequence located upstream of the polynucleotide sequence encoding a viridiflorol synthase enzyme; wherein the polynucleotide sequence encoding the RBS is selected from the group consisting of SEQ ID NO: 9, SEQ ID NO: 10, SEQ ID NO: 11 and SEQ ID NO: 17;
  iii. a polynucleotide sequence encoding a ispA gene operably linked to a promoter;
  iv. a polynucleotide sequence encoding a aroA gene operably linked to a promoter;
b. a second vector comprising:
  i. a polynucleotide sequence encoding the genes atoB, hmgS and truncated hmgR operably linked to a TM2 promoter; and
  ii. a polynucleotide sequence encoding a aroC gene operably linked to a promoter;
c. a third vector comprising:
  i. a polynucleotide sequence encoding the genes mevK, pmK, pmd and idi operably linked to a TM3 promoter; and
  ii. a polynucleotide sequence encoding a aroBgene operably linked to a promoter.

In another aspect, there is provided an engineered viridiflorol synthase enzyme comprising one or more amino acid substitutions at positions selected from the group consisting of position 227, 249, 267, 314, 318, 326, deletion of amino acids at positions 2 to 85 of SEQ ID NO: 24 and combinations thereof.

In another aspect, there is provided a method of producing viridiflorol comprising culturing the host cell according as described herein, or an *E. coli* cell as described herein in a culture medium that comprises between about 0.001-0.5 mM isopropyl β-D-1-thiogalactopyranoside (IPTG) or between about 0.1-50 mM lactose.

In another aspect, there is provided a kit for producing viridiflorol comprising the host cell as described herein, or an *E. coli* cell as described herein, together with instructions for use.

Definitions

As used herein, the term "terpene" refers to a class of organic compounds produced by plants, bacteria, fungi and insects. Terpenes are derived from isoprene, which has the molecular formula $C_5H_8$. Terpenes may be classified by the number of isoprene units in the molecule.

As used herein, the term "terpenoid" refers to a large and diverse class of organic compounds derived from terpenes and include terpenes. Terpenes are a subset of terpenoids. The building blocks of terpenes and terpenoids have a five-carbon isoprene unit and contain additional functional groups, typically oxygen-containing functional groups. Terpenoids may be derived from the chemical modification of terpenes, such as the oxidation of terpenes or recombination of the carbon skeleton of terpenes.

As used herein, the term "terpene synthase" refers to an enzyme that enzymatically modifies the terpene precursors isopentenyl pyrophosphate (IPP), dimethylallyl pyrophosphate (DMAPP) or a polyprenyl pyrophosphate, such that a terpene or terpenoid compound is produced. Terpene synthases refer to enzymes catalyzing complex carbocation-driven cyclization, rearrangement, and elimination reactions that enable the transformation of a few acyclic prenyl diphosphate substrates into a vast chemical library of terpenes or terpenoids.

The term "inducer" as used herein refers to a factor or substance that acts to stimulate the rate of transcription from an inducible promoter. Inducers may directly stimulate transcription from a promoter by physically interacting with the promoter or with DNA sequences in the vicinity of the promoter. Alternatively, inducers may indirectly stimulate transcription from a promoter by interacting with molecules that, themselves, physically interact with the promoter or with DNA sequences in the vicinity of the promoter. Inducers may be biomolecules or factors such as light and temperature. Examples of chemical inducers include lactose, arabinose, tryptophan, allolactose and isopropyl β-D-1-thiogalactopyranoside (IPTG).

As used herein, the term "promoter" refers to a region of DNA that initiates transcription of a gene. A promoter may be a major promoter, a minor promoter or an alternative promoter. A major promoter is a promoter that is the most frequently used for the transcription of a gene. A promoter may be a constitutive promoter or an inducible promoter. A constitutive promoter is a promoter that is always active. The term "inducible promoter" as used herein refers to a promoter that can be regulated in the presence of inducers which may include certain biomolecules. Examples of inducible promoter systems in *Escherichia coli* include the Tet-on system, Tet-off system, T7 system, Trp system, Tac system and Lac system.

In the context of this application, the term "ribosomal binding site" refers to a site within an mRNA molecule to which a ribosome binds, allowing the ribosome to select the proper initiation codon during the initiation of translation. Ribosomal binding sites are especially critical for regulating the protein translation in prokaryotes. In some prokaryotes, this polynucleotide sequence within the mRNA is called the Shine-Dalgarno sequence, and the Shine-Delgarno sequence base pairs with the 16S RNA of the ribosome.

BRIEF DESCRIPTION OF THE DRAWINGS

The patent or application file contains at least one drawing executed in color. Copies of this patent or patent application publication with color drawings will be provided by the Office upon request and payment of the necessary fee.

The invention will be better understood with reference to the detailed description when considered in conjunction with the non-limiting examples and the accompanying drawings, in which:

FIG. 1A shows the biosynthetic pathway: module 1 AHT, including atoB, hmgS and thmgR; module 2 MPPI, including mevk, pmk, pmd and idi; and module 3 VI, including vs, or ads, and ispA (or fpps). Abbreviation for the compounds: HMG-CoA, 3-hydroxy-3-methyl-glutaryl-coenzyme A; MVA, mevalonate; MVAP, phosphomevalonate; MVAPP, diphosphomevalonate; IPP, isopentenyl pyrophosphate; DMAPP, dimethylallyl pyrophosphate; FPP, farnesyl pyrophosphate. Dashed arrow indicates multiple enzymatic steps. The genes expressed encode the following enzymes: atoB, acetoacetyl-CoA thiolase; hmgS, HMG-CoA synthase; thmgR, truncated HMG-CoA reductase; mevk, mevalonate kinase; pmk, phosphomevalonate kinase; pmd, mevalonate pyrophosphate decarboxylase; idi, IPP isomerase; fpps, FPP synthase; vs, viridiflorol synthase; ads, *amorpha*-4,11-diene synthase. FIG. 1B shows the viridiflorol specific yields (mg/g dry cell weight (DCW)) and FIG. 1C shows the titres (mg/L) over different inducer concentrations for 6 strains. FIG. 1D shows the mathematical modelling of the optimal ranges of inducer dosages based on sum*M3. Here, 'sum' was M1+M2+M3, where M1, M2, M3 referred to the PSs of module 1, 2 and 3, respectively. FIG. 1E shows mRNA data for different modules with inducer titration. Error bars, mean±s.d., n=6.

FIG. 2A shows the specific yields (mg/g DCW) for the 27 transcriptionally tuned strains. The top 3 strains (#12, #21 and #24) were marked here. FIG. 2B shows the model-predicted yields versus the experimental yields. The regression model used polynomial equation. FIG. 2C shows a two-factor interaction plot. FIG. 2D shows the correlation between predicted yields and M1, M2 or M3. FIG. 2E is a ternary plot of viridiflorol (mg/g DCW) versus M1, M2 and M3.

FIGS. 3A-3D illustrate translation optimization and correlation. FIG. 3A shows the correlation between viridiflorol specific yields (mg/g DCW) and in silico predicted ribosomal binding site (RBS) strength or translational initiation rates (TIRs). FIG. 3B shows the correlation between titre (mg/L) and TIRs. The control (#12), top 5 (#38, #39, #40, #41 and #46) and bottom 3 producer strains (#34, #35 and #31) were highlighted in the figures. FIG. 3C shows RBS library I and their nucleic acid sequence. Design 1 (SEQ ID NO:60) refers to the design of RBS sequences in RBS library I. "W", the first base in Design 1, may be adenine or thymine. "D", the second base in Design 1, may be adenine, guanine or thymine.

FIG. 3D shows RBS library II and their nucleic acid sequence. Strain #12 and #31-52 had different upstream sequence: the upstream nucleic acid sequences of #12 and #31-52 were aacaggaggaattaaccacgacggaagcgt-caaagcacactaaatagact (SEQ ID NO: 58) and actataggggaat-tgtgagcggataacaattcccctccactaaatagact (SEQ ID NO: 59), respectively. Design 2 (SEQ ID NO: 61) refers to the design of RBS sequences in RBS library II. "N", the first base in Design 2, may be any base. "K", the second base in Design 2, may be guanine or thymine. "R", the fifth base in Design 2, may be adenine or guanine.

FIG. 4A shows the relative activities of the selected 48 single mutations based on phylogeny of fungal terpene synthases. FIG. 4B shows the viridiflorol titres and FIG. 4C shows the specific yields of wildtype, single, double and triple mutants. Error bars, mean±s.d., n=3. In FIG. 4D, the VS homologue model and 6 chosen amino acids mutation sites (G227C, L249F, E267S, V314Y, M318V and G326A) were highlighted in the model. The ligand pyrophosphate and magnesium are labelled. FIG. 4E shows the distance (Angstrom) between the ligand pyrophosphate and the 3 amino acids (G227, E267 and V314).

FIG. 5A shows the primary structure of VS. The $2^{nd}$-$85^{th}$ amino acids and those in active sites are labelled. FIG. 5B shows the viridiflorol titres in ZYM and chemically defined media. FIG. 5C shows the viridiflorol specific yields in ZYM and the defined media. Error bars, mean±s.d., n=3. Statistically significant difference of viridiflorol yield was denoted *P<0.05 (two-tailed Student's t-test). FIG. 5D shows the SDS-PAGE gel and western blot of wildtype (WT, 48 kDa) and truncated (del2-85, 39.2 kDa) VS. The control used an empty plasmid. IspA was expressed in the same operon with VS.

FIG. 6A shows the time-course profiles of dry cell weight (DCW) and viridiflorol titre (mg/L). FIG. 6B shows a summary of all the methods used in the study and their viridiflorol titres achieved. FIG. 6C shows time-course profiles of dry cell weight (DCW) and amorpha-4,11-diene titre (mg/L). The dashed arrow refers to the induction time. Error bars, mean±s.d., n=2.

FIG. 10A shows the sum*VI values for the 27 strains. FIG. 10B shows the yields over different inducer dosages for the six strains (#2, #5, #13, #17, #20 and #25). FIG. 10C shows the validation of the inducer model. Filled data points were the data of the six strains for validation. "●" refers to the upper boundary of optimal inducer dosages. "■" refers to the lower boundary of optimal inducer dosages. Empty dots and squares are the first randomly chosen strains (#1, #7, #9, #12, #24 and #27 in FIG. 8). Filled dots and squares are the validating strains (#2, #5, #13, #17, #20 and #25).

FIG. 15A shows the titre in mg/L, FIG. 15B shows the specific yield in mg/g DCW, and FIG. 15C shows the optical density OD600. The strain was induced by lactose or IPTG in chemically defined media.

FIG. 17A shows a plasmid map of the vector comprising a polynucleotide sequence encoding the atoB, hmgS and truncated hmgR genes. FIG. 17B shows a plasmid map of the vector comprising a polynucleotide sequence encoding the genes mevK, pmK, pmd and idi. FIG. 17C shows a plasmid map of the vector comprising two genes (ads, amorphadiene synthase gene and ispA). FIG. 17D shows a plasmid map of the vector comprising a polynucleotide sequence encoding the two genes (vs, viridiflorol synthase gene and ispA).

DETAILED DESCRIPTION OF THE PRESENT INVENTION

Figure 1A:
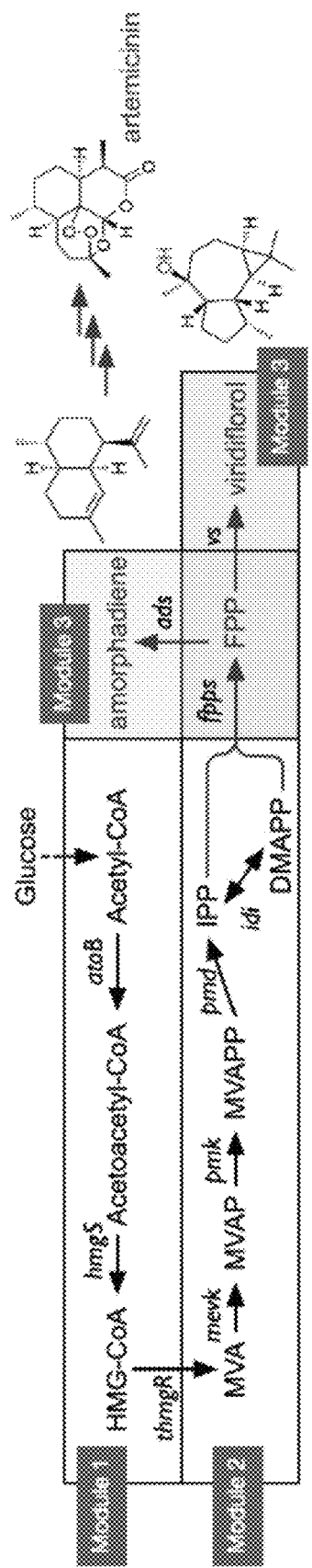
FIGS. 1A-1E show the biosynthetic pathway of viridiflorol/amorphadiene and its production with lactose titration.
Figure 1B:
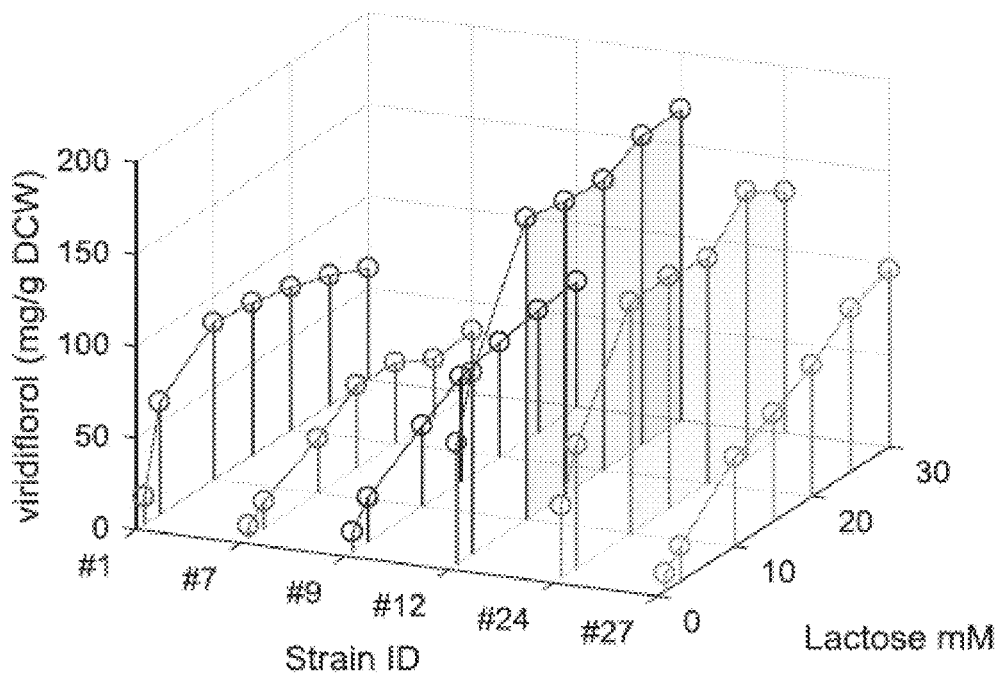
Figure 1C:
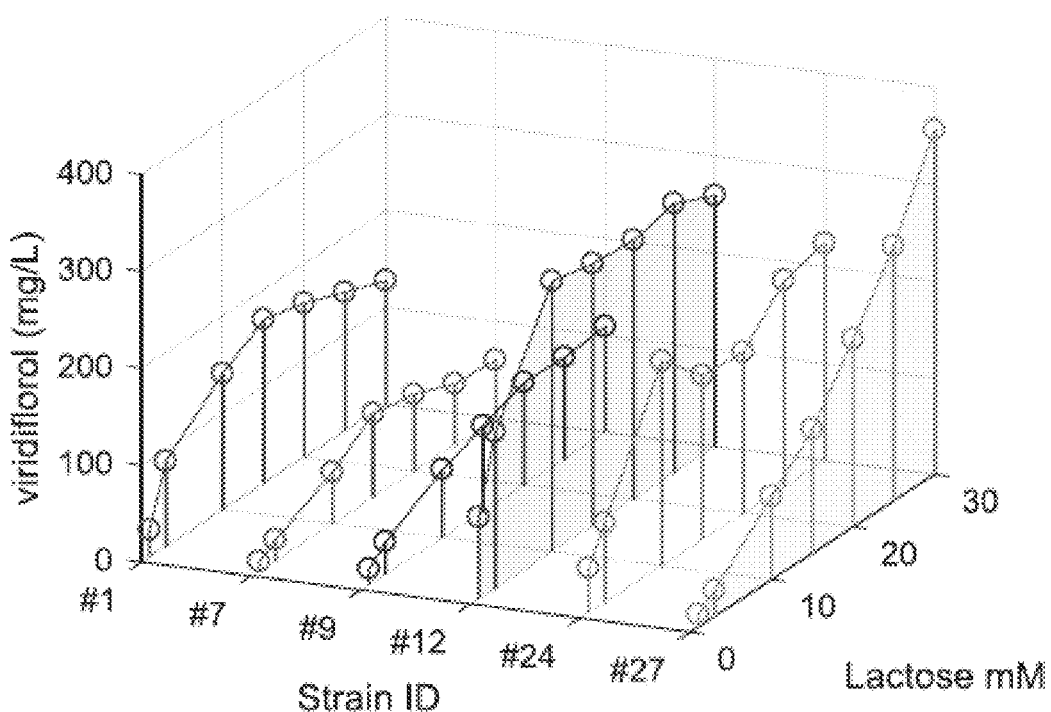

In a first aspect, the present invention refers to a method of increasing terpenoid production in a host cell that produces one or more terpenoids, comprising:
a) providing a host cell that produces one or more terpenoids, said host cell comprising a vector comprising a polynucleotide sequence encoding a terpene synthase enzyme;
b) modifying the vector to:
   i. introduce an inducible promoter operably linked to the terpene synthase enzyme; and
   ii. introduce a polynucleotide sequence encoding a ribosomal binding site (RBS) that increases translation initiation rate of the terpenoid compared to a wild type ribosomal binding site;
c) determining the dosage of an inducer capable of inducing the inducible promoter;
d) culturing the host cell in a culture medium in the presence of the inducer at the dosage determined from step c); and
e) isolating the terpenoid from the culture medium.

In one embodiment, the vector further comprises a polynucleotide sequence encoding the ispA gene.

The host cell may comprise one or more additional vectors. In one embodiment, the one or more additional vectors comprise a polynucleotide sequence encoding one or more genes of the mevalonate pathway operably linked to an inducible promoter. The genes of the mevalonate pathway may include but are not limited to atoB, hmgS, truncated hmgR, mevK, pmK, pmd, and idi. The gene truncated hmgR produces a protein with a deletion of amino acids at position 2 to 553 of hmgR (SEQ ID NO: 26). The genes of the mevalonate pathway may be located on one module or divided into multiple metabolic modules and each module may be expressed in a plasmid vector.

In another embodiment, the host cell further comprises two additional vectors. Each vector comprises a polynucleotide sequence encoding genes in a module. In yet another embodiment, the first additional vector comprises a polynucleotide sequence encoding the genes atoB, hmgS and truncated hmgR of the mevalonate pathway and the second additional vector comprises a polynucleotide sequence encoding the genes mevK, pmK, pmd and idi of the mevalonate pathway.

In one embodiment, the inducible promoter operably linked to the polynucleotide sequence encoding the terpene synthase enzyme may be selected from the group consisting of T7 promoter, Lac promoter, Trp promoter, Tac promoter, tetracycline (Tet) inducible promoter, LasR quorum-sensing promoter and EL222 light-inducible promoter.

In one embodiment, the inducible promoter is a T7 promoter. In another embodiment, the T7 promoter is a variant of the wild-type T7 promoter. A variant of the T7 promoter refers to a T7 promoter with a polynucleotide sequence that differs from the wild-type T7 promoter by one or more nucleotides. The T7 promoter variants are generated using mutations. The T7 promoter variant may be selected from the group consisting of TM1, TM2 and TM3. In one embodiment, TM1, TM2 and TM3 have the polynucleotide sequence of SEQ ID NO: 28, SEQ ID NO: 29 and SEQ ID NO: 30 respectively.

In one embodiment, the inducible promoter in each vector is the same T7 promoter variant. In another embodiment, the inducible promoter in each vector is a different T7 promoter variant.

In one embodiment, the inducible promoter in the vector comprising a polynucleotide sequence encoding a terpene synthase enzyme is TM1, the inducible promoter in the first additional vector comprising the atoB, hmgS and truncated hmgR genes is TM2, and the inducible promoter in the second additional vector comprising the mevK, pmK, pmd and idi genes is TM3.

In one embodiment, in the vector comprising a polynucleotide sequence encoding a terpene synthase enzyme, the polynucleotide sequence encoding the RBS is situated upstream of the polynucleotide sequence encoding the terpene synthase enzyme.

In another embodiment, the polynucleotide sequence encoding the RBS is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21, SEQ ID NO: 22 and SEQ ID NO: 23. In yet another embodiment, the polynucleotide sequence encoding the RBS is selected from the group consisting of SEQ ID NO: 9, SEQ ID NO: 10, SEQ ID NO: 11 and SEQ ID NO: 17.

The inducer capable of inducing the inducible promoter operably linked to the terpene synthase enzyme may be selected from the group consisting of lactose, isopropyl β-D-1-thiogalactopyranoside (IPTG), tryptophan, arabinose, tetracycline, or light. In one embodiment, the inducer is lactose or IPTG.

The inducer may be added to the culture medium at the start and be present in the culture throughout the growth of the host cell. Alternatively, the inducer may be added to the culture medium after the host cell has grown to an optimal density.

In one embodiment, the inducer dosage is determined using a regression model of promoter strength and terpenoid yield. Regression is based on experimental sampling, where inducer dosages are tuned and the corresponding terpenoid yields are measured. In one embodiment, the optimum ranges for selected strains are identified and different mathematical equations are used to fit the correlation with promoter strengths of different modules.

In another embodiment, wherein the inducer dosage is determined using the product of the total promoter strength and the strength of the promoter operably linked to the mevK, pmK, pmd and idigenes. In one embodiment, where M1 refers to the promoter strength of the promoter operably linked to the atoB, hmgS and truncated hmgR genes, M2 refers to the promoter strength of the promoter operably linked to the mevK, pmK, pmd and idigenes, and M3 refers to the promoter strength of the promoter operably linked to the viridiflorol synthase and ispA gene, the inducer dosage is determined by multiplying M2 with the sum of M1, M2 and M3.

In one embodiment, the inducer dosage is between about 0.001-0.5 mM IPTG or between about 0.1-50 mM lactose. In another embodiment, the inducer dosage is between about 0.01-0.2 mM IPTG or between about 1-25 mM lactose.

In the method of increasing terpenoid production in a host cell as described herein, the host cell may be a bacterial host cell. In one embodiment, the bacterial host cell is an *Escherichia coli* cell.

The *Escherichia coli* strain may be selected from the group consisting of BL21, BL21(DE3), K-12(RV308), K-12 (HMS174), K-12 (MG1655), W strain (ATCC 9637 and, JM109(DE3). In one embodiment, the *Escherichia coli* is a MG1655 strain. In another embodiment, the *Escherichia coli* is a BL21(DE3) strain.

In one embodiment, the *Escherichia coli* cell comprises a polynucleotide encoding a T7 RNA polymerase integrated into its genome. In another embodiment, the *Escherichia coli* is a MG1655 strain comprising a polynucleotide encoding a T7 RNA polymerase integrated into its genome.

In one embodiment, the host cell is deficient in at least one gene involved in amino acid synthesis.

In one embodiment, the vector comprising a polynucleotide sequence encoding a terpene synthase enzyme and/or the one or more additional vectors further comprises a polynucleotide sequence encoding the one or more genes that the host cell is deficient in. The polynucleotide sequence encoding the one or more genes that the host cell is deficient in may be located on the same or different vector from the vector comprising the polynucleotide sequence encoding the terpene synthase enzyme. In one embodiment, the one or more genes of that the host cell is deficient in is present on only 1 vector. The one or more genes involved in amino acid synthesis that the host cell is deficient in encode one or more enzymes that produce one or more amino acids.

The one or more genes that the host cell is deficient in may be selected from the group consisting of aroA, aroB and aroC.

In one embodiment, the vector comprising a polynucleotide sequence encoding a terpene synthase enzyme further comprises a polynucleotide sequence encoding the gene aroA. In another embodiment, the first additional vector comprising a polynucleotide sequence encoding the genes atoB, hmgS and truncated hmgR further comprises a polynucleotide sequence encoding the gene aroC, and the second additional vector comprising a polynucleotide sequence encoding the genes mevK, pmK, pmd and idi further comprises a polynucleotide sequence encoding the gene aroB.

In one embodiment, the host cell is deficient in aroA, aroB and aroC and the host cell comprises:
a) a vector comprising a polynucleotide sequence encoding a terpene synthase enzyme, a polynucleotide sequence encoding the gene ispA and a polynucleotide sequence encoding the gene aroA,
b) a first additional vector comprising a polynucleotide sequence encoding the genes atoB, hmgS, truncated hmgR and aroC, and
c) a second additional vector comprising a polynucleotide sequence encoding the genes mevK, pmK, pmd, idi and aroB.

In one embodiment, the terpene synthase enzyme may be selected from the group consisting of viridiflorol synthase and amorphadiene synthase. In one embodiment, the terpene synthase enzyme is viridiflorol synthase.

In one embodiment, the viridiflorol synthase is isolated from *Agrocybe aegerita*. In another embodiment, the amorphadiene synthase is isolated from *Artemisia annua* (Sweet wormwood).

In one embodiment, the viridiflorol synthase is mutated at one or more amino acid positions. The mutation may be selected from the group consisting of substitution, insertion, deletion, truncation and combinations thereof. The mutation may be introduced by targeted mutation, random mutation, or combinations thereof. The term "truncation" when used in the context of viridiflorol synthase refers to the viridiflorol synthase sequence with the deletion of one or more amino acids.

In one embodiment, the mutation is a substitution of one or more amino acids at positions selected from the group consisting of position 227, 249, 267, 314, 318, 326 of SEQ ID NO: 24. In another embodiment, the mutation is selected from the group consisting of G227C, L249F, E267S, V314Y, M318V, G326A and combinations thereof. In another embodiment, the mutation is a deletion of amino acids at positions 2 to 85 of SEQ ID NO: 24. In another embodiment, the mutation is selected from the group consisting of a deletion of amino acids at positions 2 to 40, 2 to 60 or 2 to 85 of SEQ ID NO: 24. In another embodiment, the mutation is selected from the group consisting of G227C, L249F, E267S, V314Y, M318V, G326A and combinations thereof and deletion of amino acids at positions 2 to 85 of SEQ ID NO: 24. In yet another embodiment, the mutation is G227C, V314Y and deletion of amino acids at positions 2 to 85 of SEQ ID NO: 24.

In one embodiment, in the method of increasing terpenoid production as described herein, the host cell is cultured in a batch, fed-batch or continuous fermentation culture. In another embodiment, the host cell is cultured in a fed-batch fermentation culture.

In another embodiment, the host cell is cultured in culture medium that does not contain antibiotics.

In one embodiment, in the method of increasing terpenoid production as described herein, the terpenoid is produced at a rate of between 0.3 g/L/h to 0.5 g/L/h. In another embodiment, terpenoid production is increased by at least 2000-fold compared to a host cell that produces one or more terpenoids comprising a vector comprising a polynucleotide sequence encoding a terpene synthase enzyme that has not been modified.

In one aspect, there is provided a host cell comprising at least one vector, wherein said at least one vector comprises:
a) a polynucleotide sequence encoding one or more genes of the mevalonate pathway operably linked to an inducible promoter;
b) a polynucleotide sequence encoding a ispA gene;
c) a polynucleotide sequence encoding a terpene synthase enzyme operably linked to an inducible promoter; and
d) a polynucleotide sequence encoding a ribosomal binding site (RBS) that increases translation initiation rate of the terpene synthase enzyme compared to a wild type ribosomal binding site.

In one embodiment, the polynucleotide sequence encoding a terpene synthase enzyme and the ispA gene are located on the same vector, and the polynucleotide sequence encoding one or more genes of the mevalonate pathway is located on a different vector. The genes of the mevalonate pathway may include but are not limited to atoB, hmgS, truncated hmgR, mevK, pmK, pmd, and idi. In yet another embodiment, the polynucleotide sequence encoding a terpene synthase enzyme and the ispA gene are located on the same vector, and the polynucleotide sequence encoding one or more genes of the mevalonate pathway is located on one or two different vectors.

In one embodiment, the polynucleotide sequence encoding the genes atoB, hmgS and truncated hmgR of the mevalonate pathway is located on a first vector and the polynucleotide sequence encoding the genes mevK, pmK, pmd and idi of the mevalonate pathway is located on a second vector.

In one embodiment, the inducible promoter operably linked to polynucleotide sequence encoding one or more genes of the mevalonate pathway or to a polynucleotide sequence encoding a terpene synthase enzyme may be selected from the group consisting of T7 promoter, Lac promoter, Trp promoter, Tac promoter, tetracycline (Tet)

inducible promoter, LasR quorum-sensing promoter and EL222 light-inducible promoter.

In one embodiment, the inducible promoter is a T7 promoter. In another embodiment, the T7 promoter is a variant of the wild-type T7 promoter. The T7 promoter variant may be selected from the group consisting of TM1, TM2 and TM3. In one embodiment, TM1, TM2 and TM3 have the polynucleotide sequence of SEQ ID NO: 28, SEQ ID NO: 29 and SEQ ID NO: 30 respectively.

In one embodiment, the inducible promoter in each vector is the same T7 promoter variant. In another embodiment, the inducible promoter in each vector is a different T7 promoter variant.

In one embodiment, the inducible promoter in the vector comprising a polynucleotide sequence encoding a terpene synthase enzyme is TM1, the inducible promoter in the first vector comprising the atoB, hmgS and truncated hmgR genes is TM2, and the inducible promoter in the second vector comprising the mevK, pmK, pmd and idi genes is TM3.

In one embodiment, in the vector comprising a polynucleotide sequence encoding a terpene synthase enzyme, the polynucleotide sequence encoding the RBS is situated upstream of the polynucleotide sequence encoding the terpene synthase enzyme.

In another embodiment, the polynucleotide sequence encoding the RBS is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21, SEQ ID NO: 22 and SEQ ID NO: 23. In yet another embodiment, the polynucleotide sequence encoding the RBS is selected from the group consisting of SEQ ID NO: 9, SEQ ID NO: 10, SEQ ID NO: 11 and SEQ ID NO: 17.

In one embodiment, the host cell as described herein is deficient in at least one gene involved in amino acid synthesis.

In one embodiment, the at least one vector further comprises a polynucleotide sequence encoding the one or more genes that the host cell is deficient in. The one or more genes involved in amino acid synthesis that the host cell is deficient in encode one or more enzymes that produce one or more amino acids.

The one or more genes that the host cell is deficient in may be selected from the group consisting of aroA, aroB and aroC.

In one embodiment, the vector comprising a polynucleotide sequence encoding a terpene synthase enzyme further comprises a polynucleotide sequence encoding the gene aroA. In another embodiment, the first vector comprising a polynucleotide sequence encoding the genes atoB, hmgS and truncated hmgR further comprises a polynucleotide sequence encoding the gene aroC, and the second vector comprising a polynucleotide sequence encoding the genes mevK, pmK, pmd and idi further comprises a polynucleotide sequence encoding the gene aroB.

In one embodiment, the terpene synthase enzyme may be selected from the group consisting of viridiflorol synthase and amorphadiene synthase. In one embodiment, the terpene synthase enzyme is viridiflorol synthase.

In one embodiment, the viridiflorol synthase is isolated from *Agrocybe aegerita*. In another embodiment, the amorphadiene synthase is isolated from *Artemisia annua* (Sweet wormwood).

In one embodiment, the viridiflorol synthase is mutated at one or more amino acid positions. The mutation may be selected from the group consisting of substitution, insertion, deletion, truncation and combinations thereof. The mutation may be introduced by targeted mutation, random mutation, or combinations thereof.

In one embodiment, the mutation is a substitution of one or more amino acids at positions selected from the group consisting of position 227, 249, 267, 314, 318, 326 of SEQ ID NO: 24. In another embodiment, the mutation is selected from the group consisting of G227C, L249F, E267S, V314Y, M318V, G326A and combinations thereof. In another embodiment, the mutation is a deletion of amino acids at positions 2 to 85 of SEQ ID NO: 24. In another embodiment, the mutation is selected from the group consisting of G227C, L249F, E267S, V314Y, M318V, G326A and combinations thereof and deletion of amino acids at positions 2 to 85 of SEQ ID NO: 24. In yet another embodiment, the mutation is G227C, V314Y and deletion of amino acids at positions 2 to 85 of SEQ ID NO: 24.

The host cell as described herein may be a bacterial host cell. In one embodiment, the bacterial host cell is an *Escherichia coli* cell.

The *Escherichia coli* strain may be selected from the group consisting of BL21, BL21(DE3), K-12(RV308), K-12 (HMS174), K-12 (MG1655), W strain (ATCC 9637) and JM109(DE3). In one embodiment, the *Escherichia coli* is a MG1655 strain. In another embodiment, the *Escherichia coli* is a BL21(DE3) strain.

In another aspect, there is provided an *Escherichia coli* cell deficient in the genes aroA, aroB and aroC, comprising:
a. a first vector comprising:
  i. a polynucleotide sequence encoding a viridiflorol synthase enzyme operably linked to a TM1 promoter; wherein said viridiflorol synthase enzyme is mutated, and wherein said mutation is G227C, V314Y and deletion of amino acids at positions 2 to 85 of SEQ ID NO: 24;
  ii. a polynucleotide sequence encoding a RBS ribosomal binding site (RBS) that increases translation initiation rate of the terpenoid compared to a wild type ribosomal binding site, said polynucleotide sequence located upstream of the polynucleotide sequence encoding a viridiflorol synthase enzyme; wherein the polynucleotide sequence encoding the RBS is selected from the group consisting of SEQ ID NO: 9, SEQ ID NO: 10, SEQ ID NO: 11 and SEQ ID NO: 17;
  iii. a polynucleotide sequence encoding a ispA gene operably linked to a promoter;
  iv. a polynucleotide sequence encoding a aroA gene operably linked to a promoter;
b. a second vector comprising:
  i. a polynucleotide sequence encoding the genes atoB, hmgS and truncated hmgR operably linked to a TM2 promoter; and
  ii. a polynucleotide sequence encoding a aroC gene operably linked to a promoter;
c. a third vector comprising:
  i. a polynucleotide sequence encoding the genes mevK, pmK, pmd and idi operably linked to a TM3 promoter; and
  ii. a polynucleotide sequence encoding a aroB gene operably linked to a promoter.

In another aspect, there is provided an engineered viridiflorol synthase enzyme comprising one or more amino acid substitutions at positions selected from the group consisting of position 227, 249, 267, 314, 318, 326, deletion of amino acids at positions 2 to 85 of SEQ ID NO: 24 and combinations thereof.

In one embodiment, the engineered viridiflorol synthase enzyme comprises the mutation G227C, V314Y and deletion of amino acids at positions 2 to 85 of SEQ ID NO: 24.

In another aspect, there is provided a method of producing viridiflorol comprising culturing the host cell as described herein, or an *E. coli* cell as described herein in a culture medium that comprises between about 0.001-0.5 mM IPTG or between about 0.1-50 mM lactose.

In one embodiment, there is provided a method of producing *amorpha*-4,11-diene comprising culturing the host cell as described herein in a culture medium that comprises between about 0.001-0.5 mM IPTG or between about 0.1-50 mM lactose. In one embodiment, the culture medium does not contain antibiotics.

In another aspect, there is provided a kit for producing viridiflorol comprising the host cell as described herein, or an *E. coli* cell as described herein, together with instructions for use.

In one embodiment, there is provided a kit for producing *amorpha*-4,11-diene comprising the host cell as described herein, together with instructions for use.

EXPERIMENTAL SECTION

Non-limiting examples of the invention and comparative examples will be further described in greater detail by reference to specific Examples, which should not be construed as in any way limiting the scope of the invention.

Materials and Methods

Strain and Plasmid Construction

*E. coli* K12 MG1655 ΔrecAΔendA DE3 and MG1655 ΔrecAΔendAΔaroAΔaroBΔaroC DE3 were used for terpenoid production. The auxotrophic *E. coli* strain was obtained by sequential knockout of the three genes aroABC with the primers aroA-F&R, aroB-F&R and aroC-F&R (Table 1) and the λ red recombinase. The plasmids p15A-spec-hmgS-atoB-hmgR (L2-8) and p15A-cam-mevK-pmk-pmd-idi (L2-5) were also used. The operon crtEBI in the plasmid p15A-kan-crtEBI-ispA was replaced with the codon-optimized viridiflorol synthase (VS) from *Agrocybe aegerita*, obtaining the plasmid p15A-kan-vs-ispA. *Amorpha*-4,11-diene synthase (ADS) was amplified from plasmid pACM-T7-dxs-T7-idi-ADS-ispA and cloned into p15A-kan vector together with ispA. The genes aroA, aroB and aroC were subsequently integrated into the plasmids, p15A-kan, p15A-cam, p15A-spec, respectively. The promoters of plasmids were mutated with in-house cloning method modified based on Agilent QuikChange II method. The strains and plasmids used in this study were summarized in Table 2.

TABLE 1

Primers used in the study

| Primer name | Sequence | Remarks | SEQ ID NO |
|---|---|---|---|
| aroA-F | gttgtagagagttgagttcatggaatccctgacgttacaacccatcgctc | aroA-F | 31 |
| aroA-R | cattcaggctgcctggctaatccgcgccagctgctcgaaataatccggaa | aroA-R | 32 |
| aroC-F | cggagccgtgatggctggaaacacaattggacaactctttcgcgtaacca | aroC-F | 33 |
| aroC-R | ccagcgtggaatatcagtcttcacatcggcattttgcgcccgttgccgta | aroC-R | 34 |
| aroB-F | ctgcgggtacagtaattaaggtggatgtcgcgttatggagaggattgtcg | aro B-F | 35 |
| aroB-R | ccccatttcagcttcaatggcatgaccaaaggtgtgtcccagattcagta | aro B-R | 36 |
| OL(24)-F | ACTAAATAGACTWDGAAGAGGCCTaaaatgcatcaccatcacca | RBS library 1 | 37 |
| OL(24)-R | AGGCCTCTTCHWAGTCTATTTAGTgtgctttgacgcttccgtc | RBS library 1 | 38 |
| TS-20-OL(24)-F | tccactaaatagactNKAaRgaggTAtaaaatgcatcac | RBS library 2 | 39 |
| TS-20-OL(24)-R | YTTMNAGTCTATTTAGTGGAggggaattgttatccgct | RBS library 2 | 40 |
| 4879_DEL_F | catcaccatcaccatcacacgagccatagcccgcgcgt | VS truncation | 41 |
| 4879_DEL_R | gtgatggtgatggtgatgcattttaggcctcttcttagtc | VS truncation | 42 |

TABLE 2

Strain Nomenclature

| plasmids | Remarks |
|---|---|
| p15A-spec-aroC-hmgS-atoB-hmgR (L2-8) | Expressing three genes in the module 1 or HAT and aroC gene |
| p15A-cam-aroB-mevK-pmk-pmd-idi (L2-5) | Expressing three genes in the module 2 or MPPI and aroB gene |
| p15A-kan-aroA-vs-ispA | Expressing three genes in the module 3 or VI (for viridiflorol) and aroC gene |
| p15A-kan-aroA-ads-ispA | Expressing three genes in the module 3 (for amorphadiene) and aroC gene |

Wild-type *E. coli* MG1655 - K12 MG1655 ΔrecAΔendA with a T7 RNA polymerase (DE3) integrated. Auxotrophic *E. coli* MG1655ΔaroABC - with the three genes deleted in MG1655 wildtype. The gene VS was isolated from *Agrocybe aegerita*.

Construction of RBS Library

Two RBS libraries were designed for viridiflorol synthase (VS) using the degenerate primer OL(24)-F&R (SEQ ID NOs 37-38) and TS-20-OL(24)-F&R (SEQ ID NOs 39-40) (Table 1), respectively. The cloning method used was the Cross-Lapping In Vitro Assembly (CLIVA) method. RBS design was aided by RBS Calculator, version 2.0. The predicted translation efficiencies of the RBS libraries were listed in FIGS. 3C and 3D.

Statistical Analysis

Linear regression models were used to study the relationships between the response (viridiflorol yields) and the variables (e.g. promoter strengths of different modules, RBS strengths or TIRs of the VS gene). For transcriptional optimization, our strain design is a $3^3$ full factorial design [3 factors or variables (M1, M2 and M3) and 3 levels (TM1=0.92, TM2=0.37, TM3=0.16) for each factor]. As in response surface methodology, the polynomial model (FIG. 2B) was used to describe the relationship between the response and the variables. Here, the model includes linear terms (e.g. M1), cross product terms (e.g. M1*M2) and a second order term (e.g. $M1^2$) of each factor. The parameters (a, b, . . . , j) were calculated by multiple linear regression. Coefficient of determination ($R^2$) was calculated with the polynomial model and was used to compare the fit of the models.

Enzyme Engineering

Targeted point mutations were introduced into VS using in-house cloning method modified based on Agilent QuikChange II method. The primers (1F&R to 52F&R) used were listed in Table 1. Random mutations were introduced with GeneMorph II Random Mutagenesis Kit (Agilent, Stratagene). Double mutation and triple mutation were introduced sequentially with the single VS mutant as the template. For VS truncation, the same cloning method was used with the primer pair 4879_DEL_F&R. All the enzyme mutants were sequenced afterwards to confirm the mutation.

Homologue Model Building

The homologue model of VS was built on the structure of epi-isozizaene synthase (PDB ID: 4ltz). Sequence alignment (FIG. 14) was performed with Clustal Omega (https-:colon-forward-slash-forward-slash-www.ebi.ac.uk/Tools/msa/clustalo/) with default setting. The binding pocket, consisting of 15 residues within 6 angstroms from the substrate, was determined by PyMOL software v2.1.1. All the protein structures in the study were prepared by PyMOL software.

Media Used in the Study

ZYM medium was prepared using 1% tryptone, 0.5% yeast extract, 25 mM $Na_2HPO_4$, 25 mM $KH_2PO_4$, 50 mM $NH_4Cl$, 5 mM $Na_2SO_4$, 2 mM $MgSO_4$, 0.5% glycerol, 0.05% glucose and 1-30 mM of α-lactose. Chemically defined medium contained 10 g/L glucose, 2 g/L $(NH_4)_2SO_4$, 4.2 g/L $KH_2PO_4$, 11.24 g/L $K_2HPO_4$, 1.7 g/L citric acid, 0.5 g/L $MgSO_4$ and 10 ml/l trace element solution, pH 7.0. The trace element solution (100×) contained 0.25 g/L $CoCl_2.6H_2O$, 1.5 g/L $MnSO_4.4H_2O$, 0.15 g/L $CuSO_4.2H_2O$, 0.3 g/L $H_3BO_3$, 0.25 g/L $Na_2MoO4._2H_2O$, 0.8 g/L $Zn(CH_3COO)_2$, 5 g/L Fe(III) citrate and 0.84 g/L EDTA, pH 8.0.

Tube Culture of the E. coli Strains

For strain optimization, the cells were grown in 1 mL of ZYM medium in 14 ml BD Falcon™ tube at 28° C./250 rpm for 2-3 days. In addition, 200 µL dodecane (with 500 mg/L β-caryophyllene as internal control) was used to extract viridiflorol during cell culture. When used the defined media, the cells were initially grown at 37° C./250 rpm until OD600 reached ~0.8, induced by 0.01~0.15 mM IPTG (or 1~30 mM lactose), and were then grown at 28° C. for 2 days. For wildtype strains, the media were supplemented with the antibiotics (34 µg/ml chloramphenicol, 50 µg/ml kanamycin and 50 µg/ml spectinomycin) to maintain the three plasmids.

Bioreactor Fermentation for Viridiflorol Production

Two 250 ml Mini Bioreactors (Applikon Biotechnology) were used with 100-200 mL working volume in this study. The cells (−80° C. stock) were grown 10 ml defined medium for 48 h at 37° C. Five milliliter of the grown cell suspension (OD of ~5) was harvested, washed and inoculated into 100 ml the defined medium in the bioreactor. Once OD reached about 5, feed solution (500 g/L glucose and 5 g/L $MgSO_4$) was added into the bioreactor at the rate of 0.6-1.8 mL/h for about 3 h and another feeding cycle was started by DO trigger or offline checking of residual glucose (e.g. DO increased abruptly or glucose concentration dropped below 3 g/L). The feeding cycle was repeated until induction. The cells were induced by 0.1 mM IPTG when OD reached about 30-40 (16-18 h from inoculation). After induction, a constant feeding rate at 5 g/L/h of glucose and 0.05 g/L/h of $MgSO_4$ was maintained. The culture temperature was adjusted to 30° C. and 20% (v/v) of dodecane with 1 g/L of caryophyllene was supplemented into the bioreactor. During the fermentation, dissolved oxygen level was maintained at 30% (800-2000 r.p.m.) by supplying filtered air at a gas rate of 1.5 vvm. The pH of the culture was controlled at 7.0 with 28% ammonia solution. The fed-batch experiments were performed in the defined media without any antibiotics.

Theoretic Yield of Viridiflorol and Amorphadiene

It is known that the production of isoprene or isopentenyl pyrophosphate (IPP) via the mevalonate pathway under aerobic fermentation requires three acetyl coenzyme A (AcCoA), three ATP and two NAD(P)H. Therefore, (1) 1.5 Glucose+2 $O_2$→3 AcCoA+3 ATP+3 $CO_2$+6 NAD(P)H (glycolysis)

(2) 3 AcCoA+2 NAD(P)H→MVA (3) MVA+3 ATP→IPP+$CO_2$ (4) 3 IPP→Viridiflorol/amorphadiene Overall 4.5 Glucose+9 $O_2$→Viridiflorol/amorphadiene+12 $CO_2$+15 $H_2O$, viridiflorol and amorphadiene mass yield on glucose is 27.4% and 25.2%, respectively.

Quantification of Terpenoids

The terpenoid samples were prepared by diluting 10-20 µl of organic layer into 1000 µl hexane. The samples were analyzed on an Agilent 7890 gas chromatography equipped with an Agilent 5977B MSD. Samples were injected into Agilent VF-WAXms column with a split ratio of 40:1 at 240° C. The oven program started at 100° C. for 1 min, was raised up to 150° C. at 50° C./min, then to 240° C. at 15° C./min and maintained at 240° C. for another 2 min. The compound concentrations were calculated by interpolating with a standard curve prepared by authentic viridiflorol standard (Santa Cruz Biotechnology, USA) or relative ratios to the internal standard β-caryophyllene. Mass spectrometer was operated in EI mode with full scan analysis (m/z 30-300, 2 spetra/s).

RNA Purification and Quantitative PCR Assay

Total RNA samples from E. coli cells were prepared using PureLink® RNA Mini Kit (Thermo Fisher Scientific, USA) according to the manufacturer's instructions. RNA samples were collected 1 hour after induction (at an $OD_{600}$ of ~1.5) in biological triplicates. RNA was reversed transcribed and cDNA was quantified in technical duplicates with SYBR green. Transcript levels were normalized by the reference cycG. For module 1 (HAT), the genes hmgr and hmgs were used. For module 2 (MPPI), the genes mk and idiwere used; for module 3 VI, the genes vs and ispA were used. All the genes were analyzed for the four strains (#1 #7, #12, #27). The primers (primer names started with 'rt') used for quantitative PCR were in Table 1.

Results

Example 1: Transcriptional Optimization and Statistical Analysis

Figure 7:
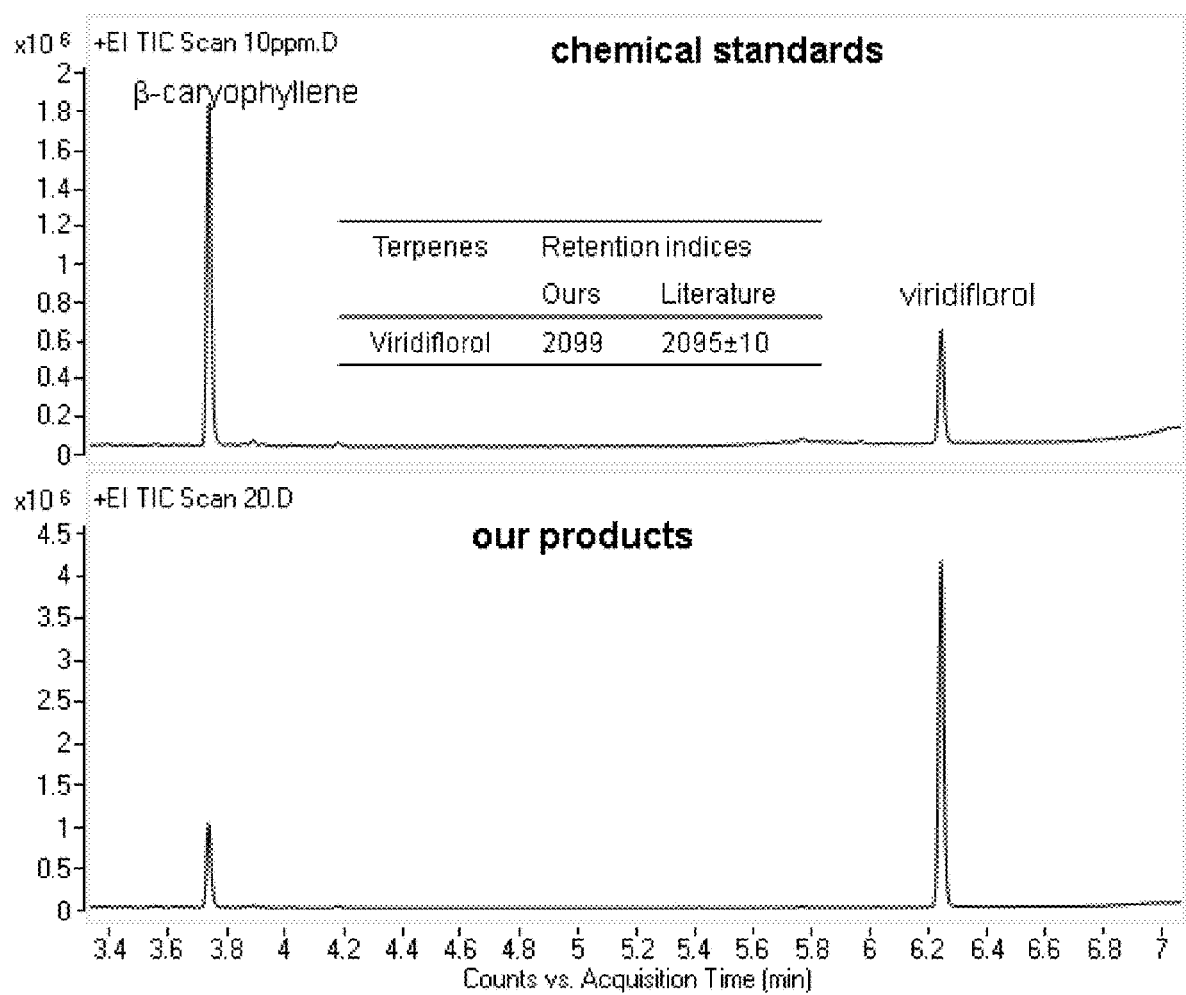
FIG. 7 shows GC chromatograms and mass spectra of viridiflorol and amorphadiene. β-Caryophyllene was spiked into the culture media as an internal control. Retention index and mass spectrum were used to validate the viridiflorol product.
Figure 7:
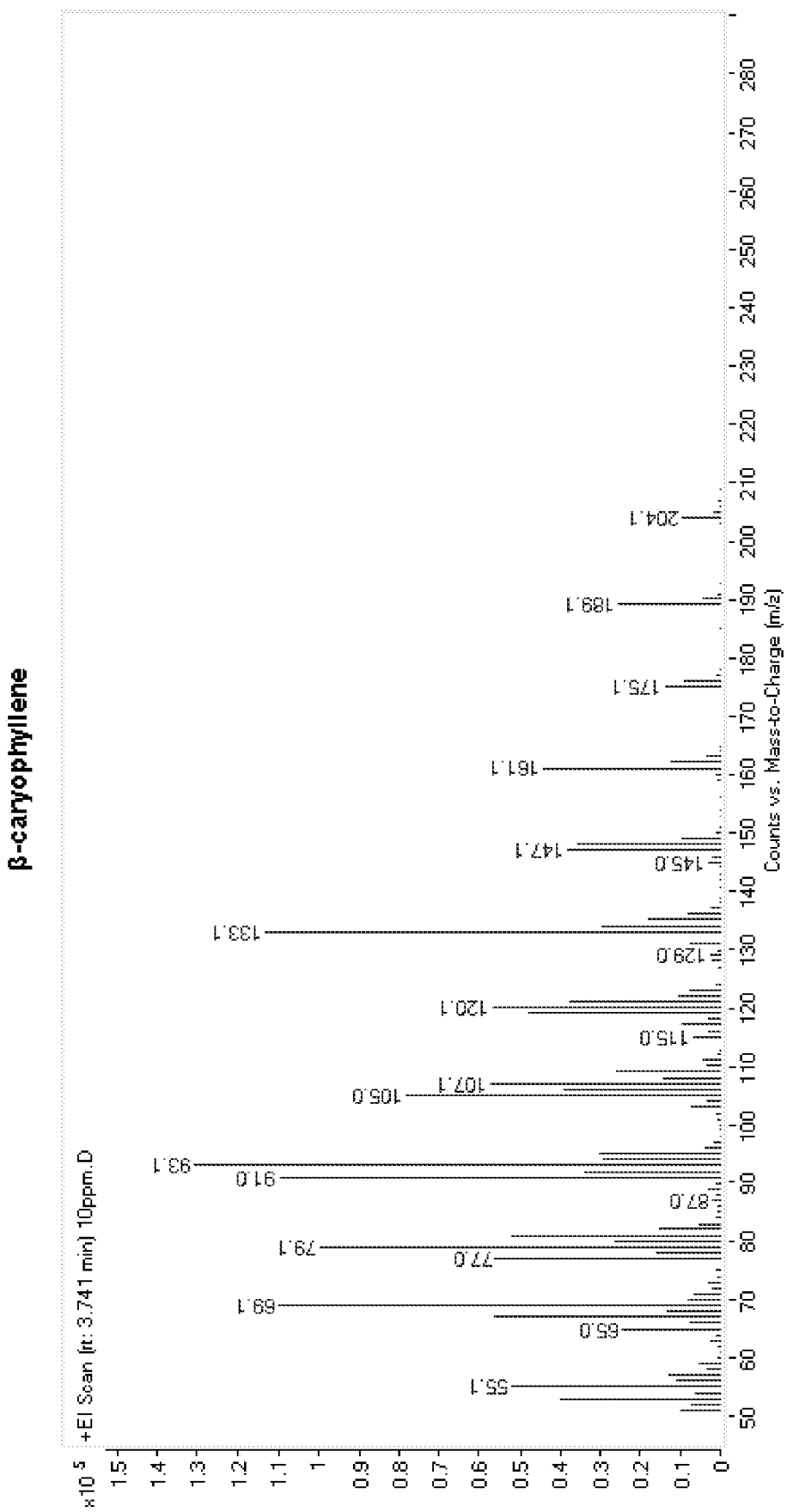
Figure 7:
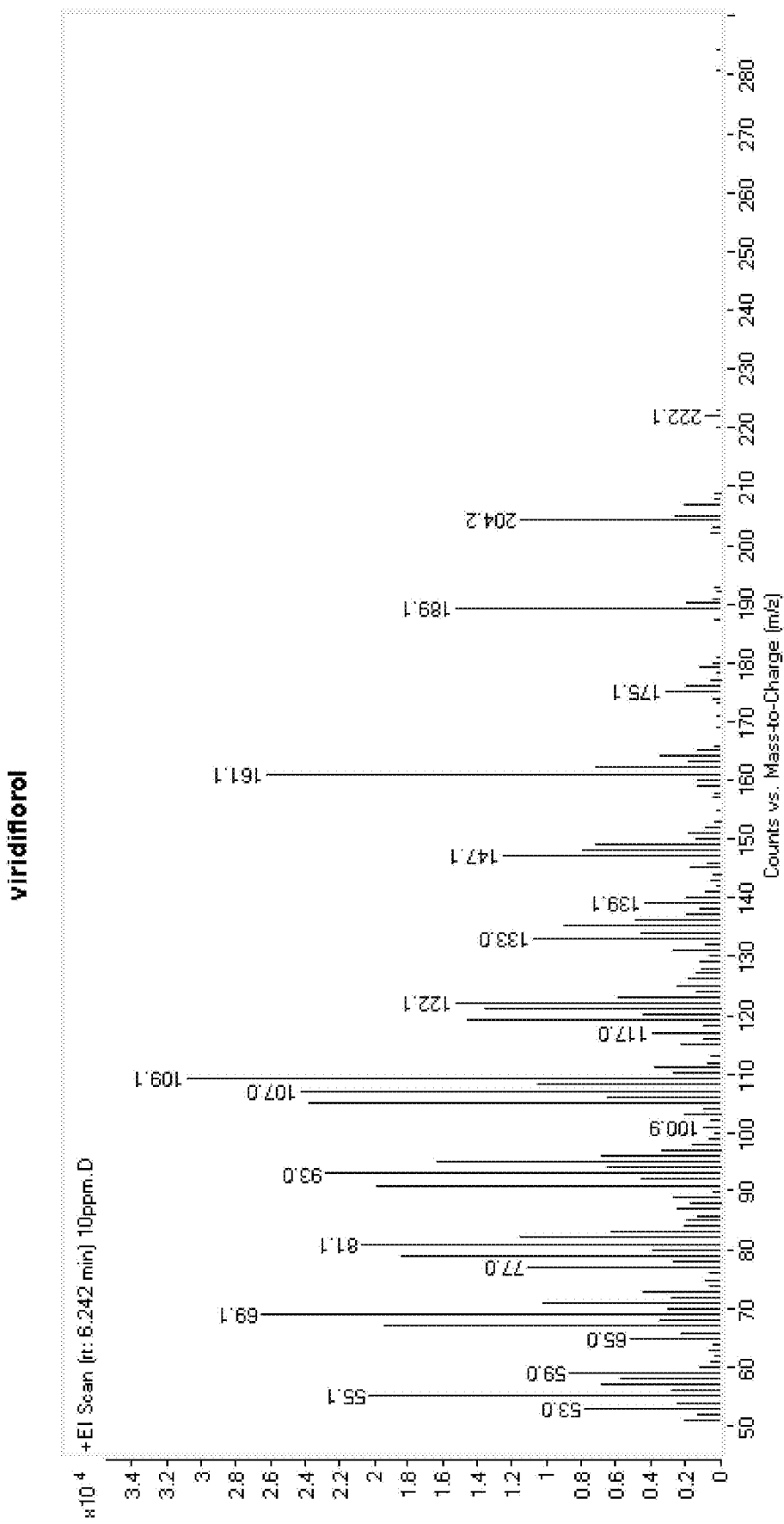

The mevalonate pathway genes of Saccharomyces cerevisiae were grafted into the E. coli MG1655 strain. Briefly, the mevalonate pathway genes were divided into two metabolic modules—module 1 or AHT including the genes atoB, hmgS and truncated hmgR and module 2 or MPPI including the genes mevK, pmK, pmd and idi(FIGS. 1A-1E). The farnesyl diphosphate (FPP) synthase (fpps, or ispA) was on module 3 or VI, together with the VS gene. The three modules were expressed in three plasmids (Table 2). It has previously been shown that such module structure works for both carotenoids and sesquiterpenes. And this natural modular method by dividing genes into modules according to their positions in the metabolic pathway (e.g. upstream, midstream and downstream) enable easier diagnosis of the pathway bottlenecks. Remarkably, the fungal VS produced viridiflorol as the single product (FIG. 7, where β-caryophyllene was an internal control). It has been shown that the three T7 promoter variants (TM1, TM2 and TM3, whose strengths were 92%, 37% and 16% of that of T7 promoter, respectively) are sufficient to cover an initial searching resolution. Thus, 27 different strains (strain #1 to #27, Table 3), covering a full permutation (3 promoters and 3 modules, $3^3=27$), were constructed. With different promoters, modules were coordinated transcriptionally to prevent accumulation of toxic intermediates and thus maximizing the product yield.

TABLE 3

Promoter information for the 27 strains

| Strain | Promoter | | | Promoter strength | | | Promoter indices | | |
|---|---|---|---|---|---|---|---|---|---|
| ID | AHT | MPPI | VI | AHT | MPPI | VI | AHT | MPPI | VI |
| #1 | TM1 | TM1 | TM1 | 92% | 92% | 92% | 31% | 31% | 31% |
| #2 | TM1 | TM2 | TM1 | 92% | 37% | 92% | 38% | 6% | 38% |
| #3 | TM1 | TM3 | TM1 | 92% | 16% | 92% | 42% | 1% | 42% |
| #4 | TM1 | TM1 | TM2 | 92% | 92% | 37% | 38% | 38% | 6% |
| #5 | TM1 | TM2 | TM2 | 92% | 37% | 37% | 51% | 8% | 8% |
| #6 | TM1 | TM3 | TM2 | 92% | 16% | 37% | 58% | 2% | 9% |
| #7 | TM1 | TM1 | TM3 | 92% | 92% | 16% | 42% | 42% | 1% |
| #8 | TM1 | TM2 | TM3 | 92% | 37% | 16% | 58% | 9% | 2% |
| #9 | TM1 | TM3 | TM3 | 92% | 16% | 16% | 68% | 2% | 2% |
| #10 | TM2 | TM1 | TM1 | 37% | 92% | 92% | 6% | 38% | 38% |
| #11 | TM2 | TM2 | TM1 | 37% | 37% | 92% | 8% | 8% | 51% |
| #12 | TM2 | TM3 | TM1 | 37% | 16% | 92% | 9% | 2% | 58% |
| #13 | TM2 | TM1 | TM2 | 37% | 92% | 37% | 8% | 51% | 8% |
| #14 | TM2 | TM2 | TM2 | 37% | 37% | 37% | 12% | 12% | 12% |
| #15 | TM2 | TM3 | TM2 | 37% | 16% | 37% | 15% | 3% | 15% |
| #16 | TM2 | TM1 | TM3 | 37% | 92% | 16% | 9% | 58% | 2% |
| #17 | TM2 | TM2 | TM3 | 37% | 37% | 16% | 15% | 15% | 3% |
| #18 | TM2 | TM3 | TM3 | 37% | 16% | 16% | 20% | 4% | 4% |
| #19 | TM3 | TM1 | TM1 | 16% | 92% | 92% | 1% | 42% | 42% |
| #20 | TM3 | TM2 | TM1 | 16% | 37% | 92% | 2% | 9% | 58% |
| #21 | TM3 | TM3 | TM1 | 16% | 16% | 92% | 2% | 2% | 68% |
| #22 | TM3 | TM1 | TM2 | 16% | 92% | 37% | 2% | 58% | 9% |
| #23 | TM3 | TM2 | TM2 | 16% | 37% | 37% | 3% | 15% | 15% |
| #24 | TM3 | TM3 | TM2 | 16% | 16% | 37% | 4% | 4% | 20% |
| #25 | TM3 | TM1 | TM3 | 16% | 92% | 16% | 2% | 68% | 2% |
| #26 | TM3 | TM2 | TM3 | 16% | 37% | 16% | 4% | 20% | 4% |
| #27 | TM3 | TM3 | TM3 | 16% | 16% | 16% | 5% | 5% | 5% |

Figure 8:
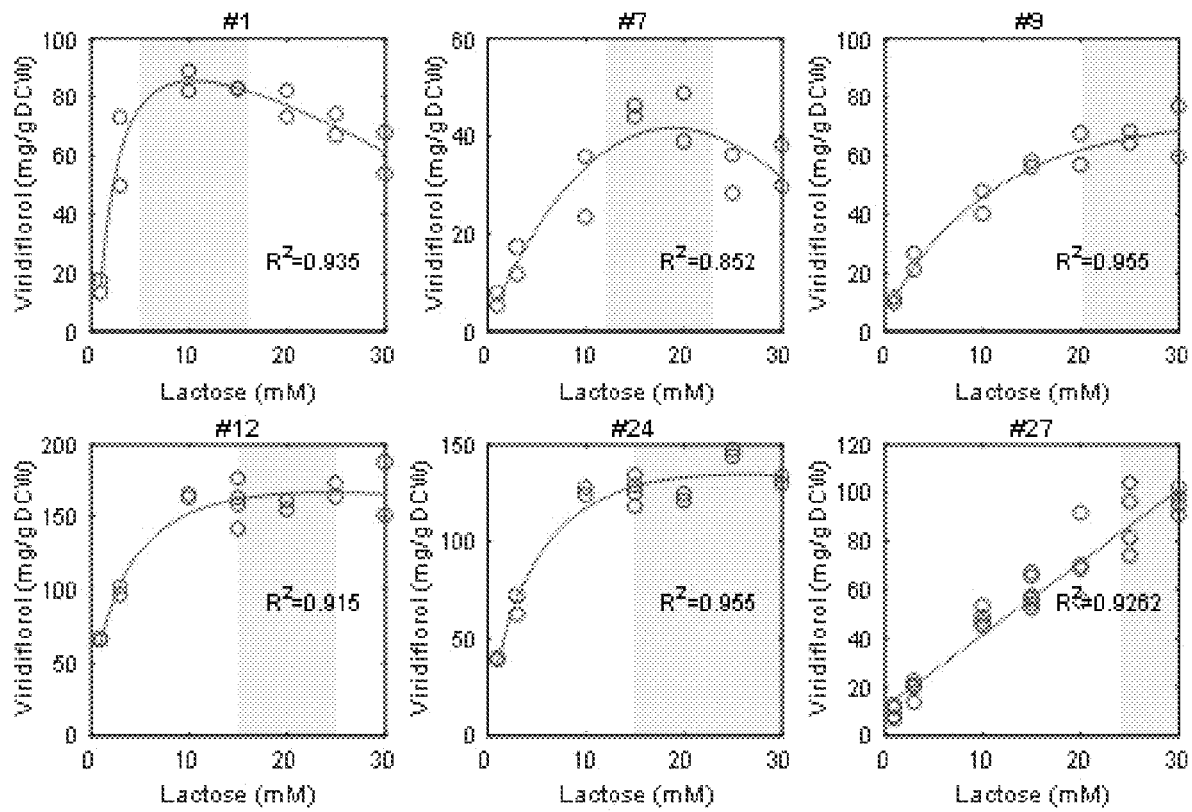
FIG. 8 shows the data fitting of viridiflorol yield (mg/g DCW) and lactose concentration for the 6 strains. The two equations were used for the data fitting. The relative strength of promoters for each module was listed in the figure. EQ1 was used to simulate strains #1, #7, #9, #12 and #24; EQ2 was used to simulate strain #27.
Figure 9:
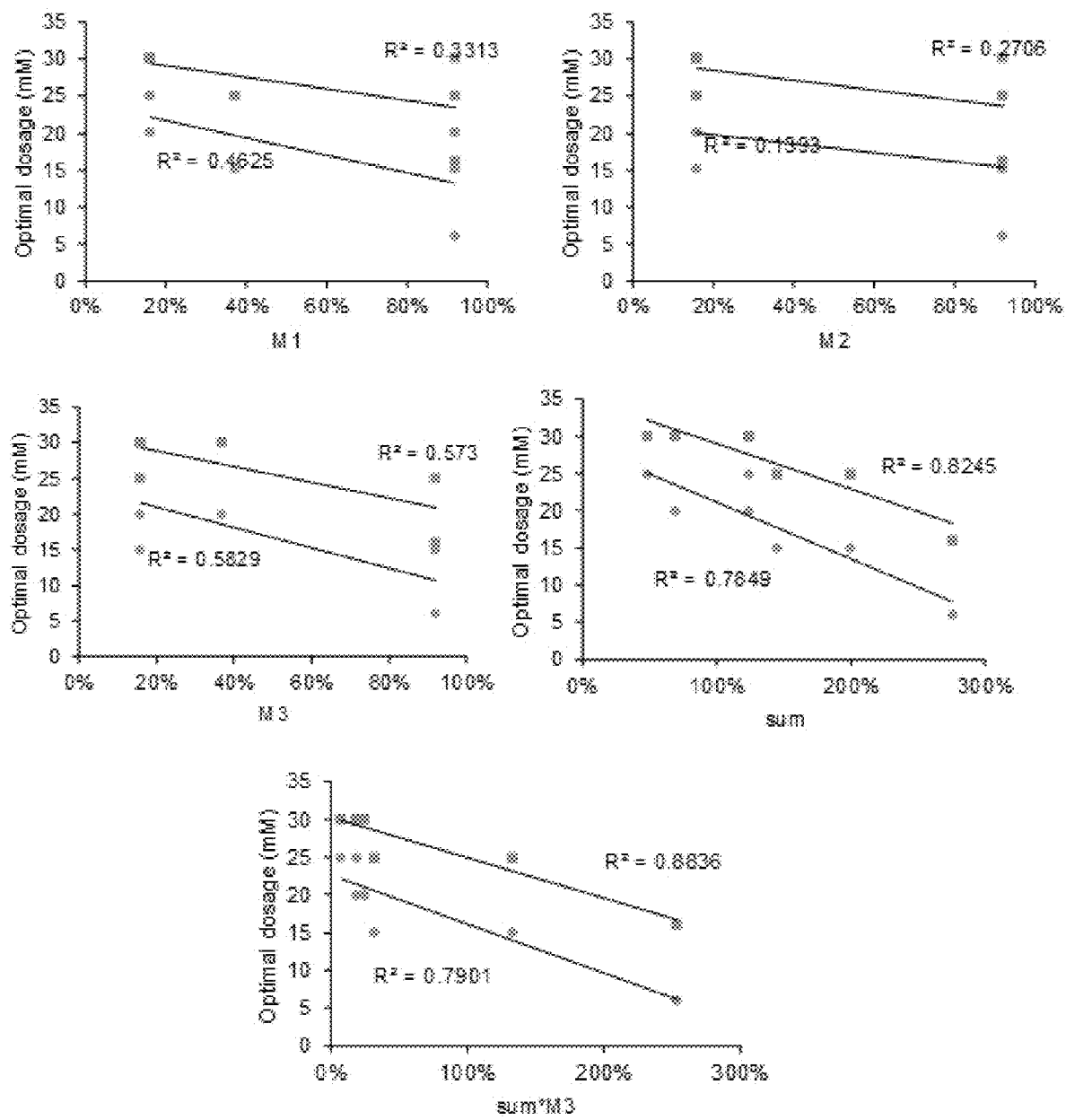
FIG. 9 shows the correlation of optimal inducer dosages with different parameters (M1, M2, M3, sum and sum*M2). M1, M2, M3 referred to the PSs of module 1, 2 and 3, respectively. Sum referred to the sum of M1, M2 and M3. The optimal inducer dosages were better correlated with sum*M2 than other parameters. "■" refers to the upper boundary of optimal inducer dosages. "●" refers to the lower boundary of optimal dosages.

Inducer concentration is critical for achieving the maximal yields of proteins or metabolites. Generally, strains with stronger promoters require less amount of inducer than those with weaker promoters. However, little is known about the absolute inducer dosage for each strain and it is tedious to test a large number of strains with many different concentrations of inducers. Therefore, a study was carried out to investigate the mathematical relationship between inducer concentrations and viridiflorol yields via auto-induction in ZYM medium with lactose as the inducer, as auto-inducing media is more convenient and can avoid human errors and mistiming of induction especially when the growth rates of different strains vary. The experiment started with six randomly selected strains (#1, #7, #9, #12, #24 and #27). Firstly, the data in FIGS. 1B and 1C reaffirmed inducer dosages were critical for viridiflorol production and several strains did have distinct optimal inducer dosages. Secondly, two equations were sufficient to simulate their relationship with $R^2$ value of 0.85-0.95 (FIG. 8). Furthermore, the optimal ranges of inducer dosage (the upper and lower limits) determined by the data in FIG. 8 were correlated with M1, M2, M3, sum, and the product of sum and M1. Here, 'M1', 'M2' and 'M3' referred to the promoter strength (PS) of module 1, 2 and 3 of each strain, respectively; 'sum' referred to the sum of M1, M2 and M3 (e.g. for strain #7, M1, M2 and M3 were 0.92, 0.92 and 0.16, respectively; sum was 0.92+0.92+0.16=2 and sum*M3 was 2*0.16=0.32). It was found the optimal inducer dosages were better correlated (inversely) with the product of sum and M1 (FIG. 9).

Figure 1D:
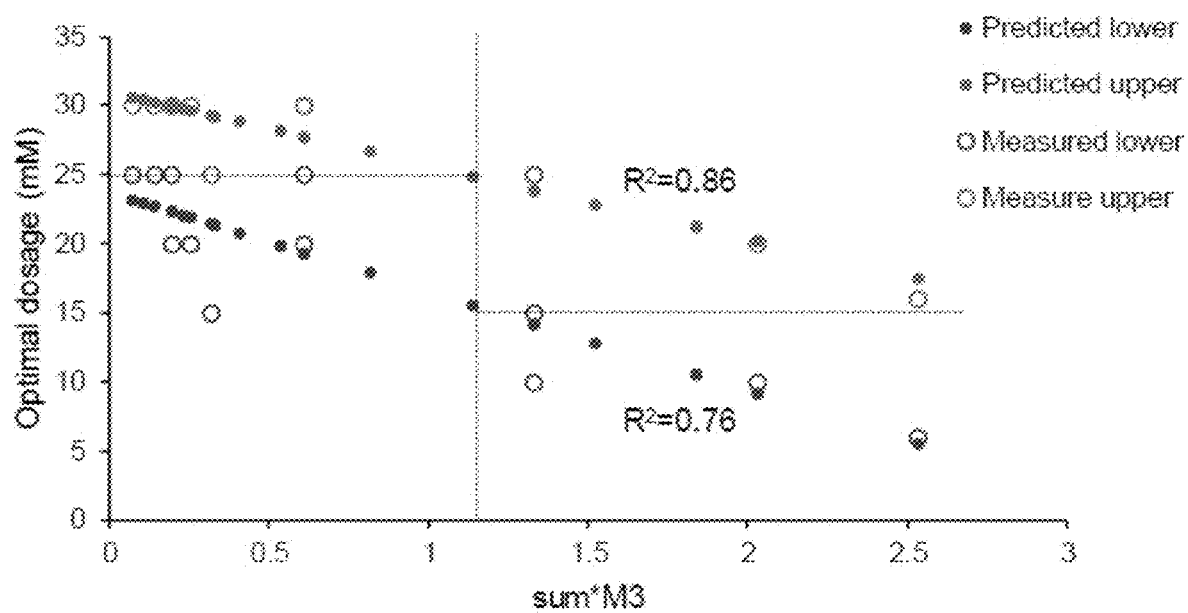
Figure 1E:
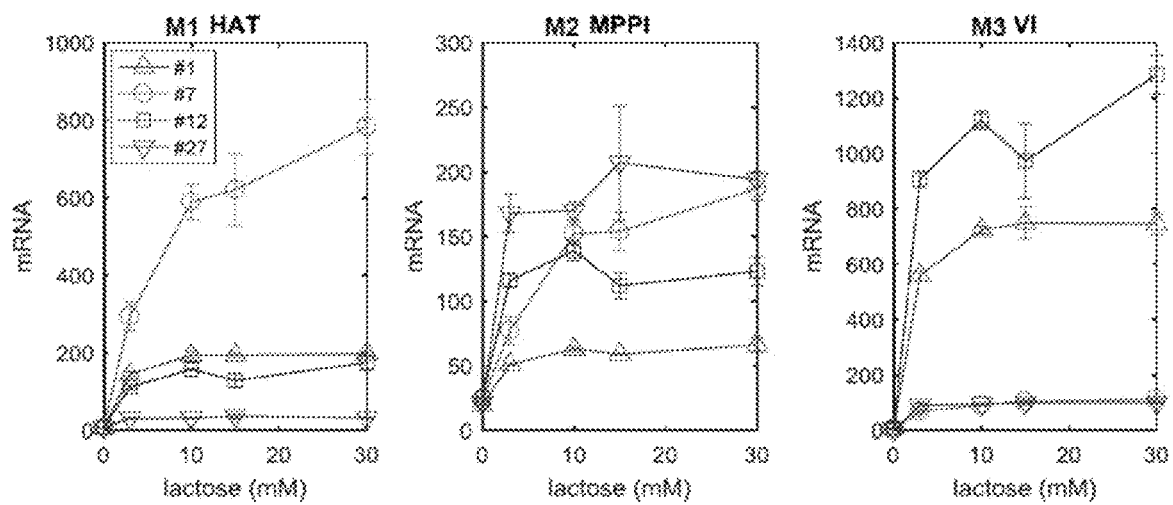
Figure 10:
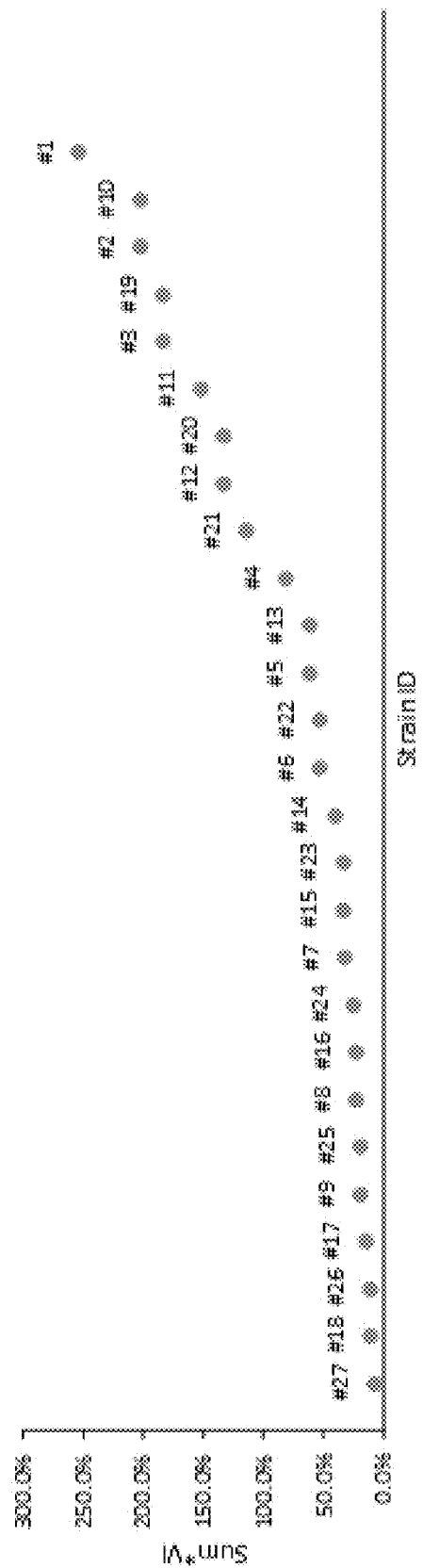
FIGS. 10A-10C show the validation of the inducer model.
Figure 10B:
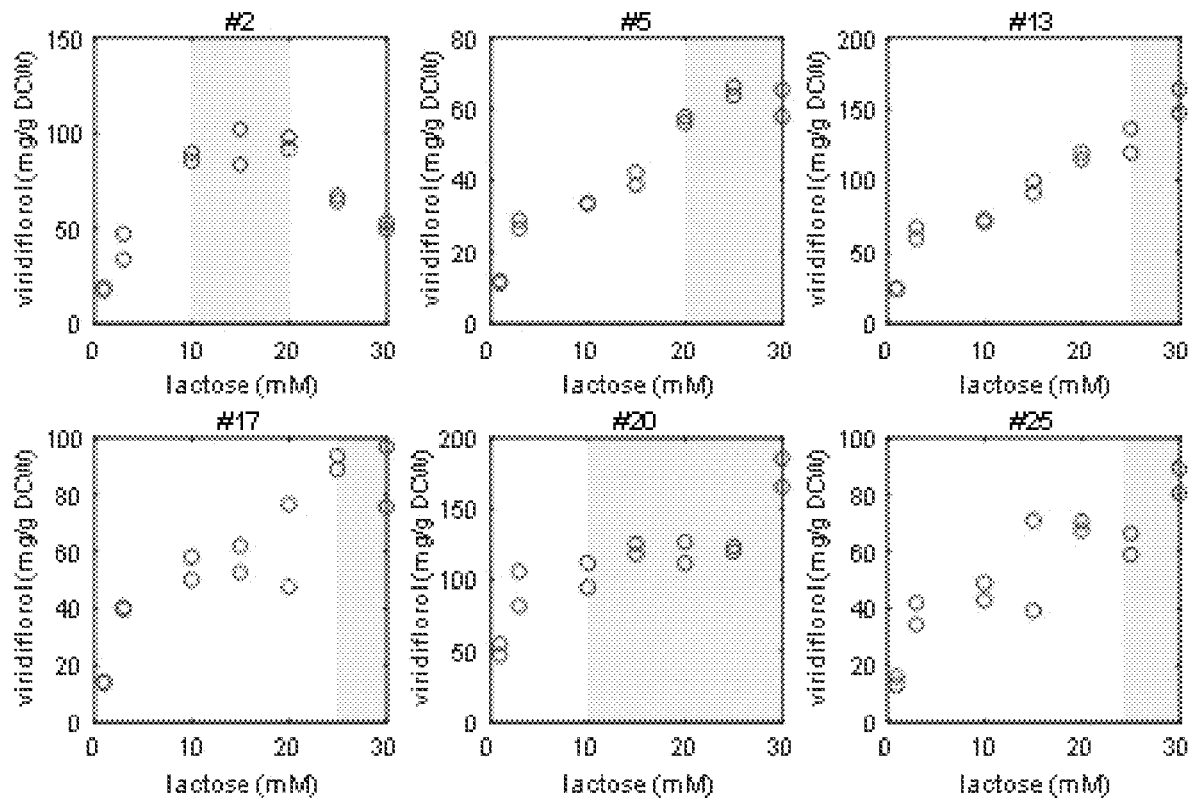
Figure 10C:
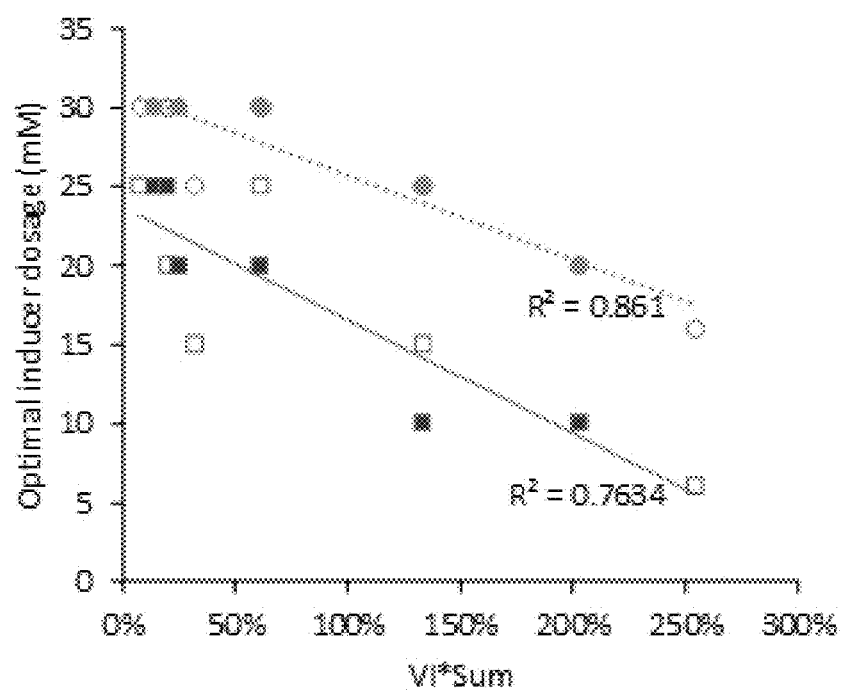

With a linear regression model, the optimal inducer ranges were predicted for all the 27 strains (FIG. 1D and FIG. 10A). Based on the model, the optimal ranges shifted gradually from 5-15 mM to 25-30 mM for the 27 strains; and one of two concentrations (15 and 25 mM) would be within the optimal range for all the 27 strains. To validate the model, another six strains (#2, #5, #13, #17, #20 and #25) were tested and the experimental data were consistent with our prediction (FIGS. 10B and 10C). Furthermore, mRNA data was measured to better understand the relationship between viridiflorol production and inducer dosages. It was found that for the majority of the gene transcription levels plateaued at 10-15 mM of lactose (FIG. 1E) and others at 25-30 mM, consistent with our inducer model in FIG. 1D.

Figure 2A:
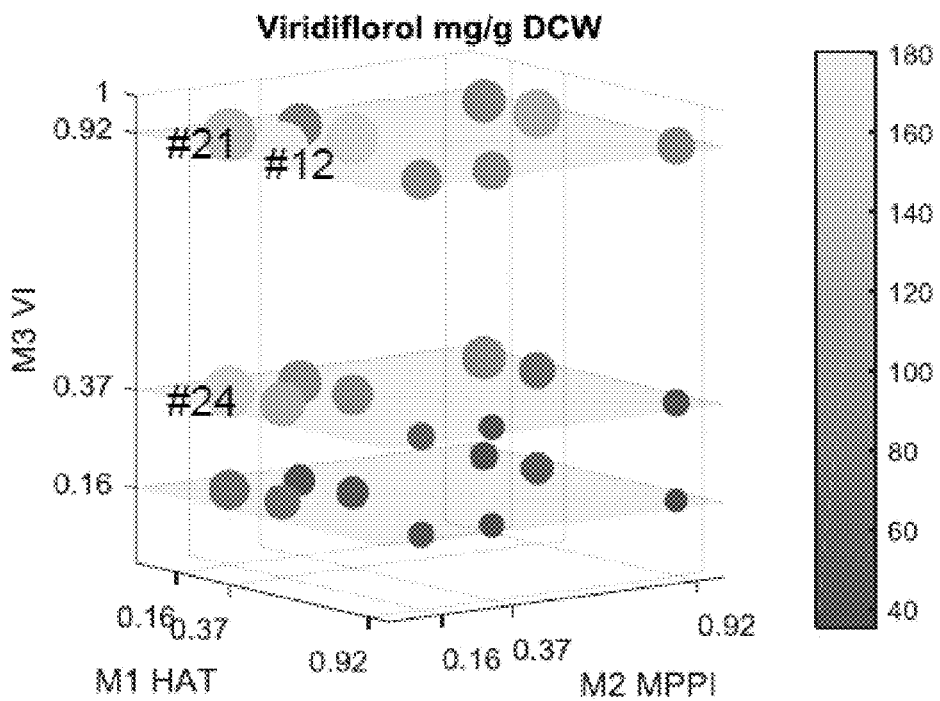
FIGS. 2A-2E illustrate transcriptional optimization and modelling.
Figure 2B:
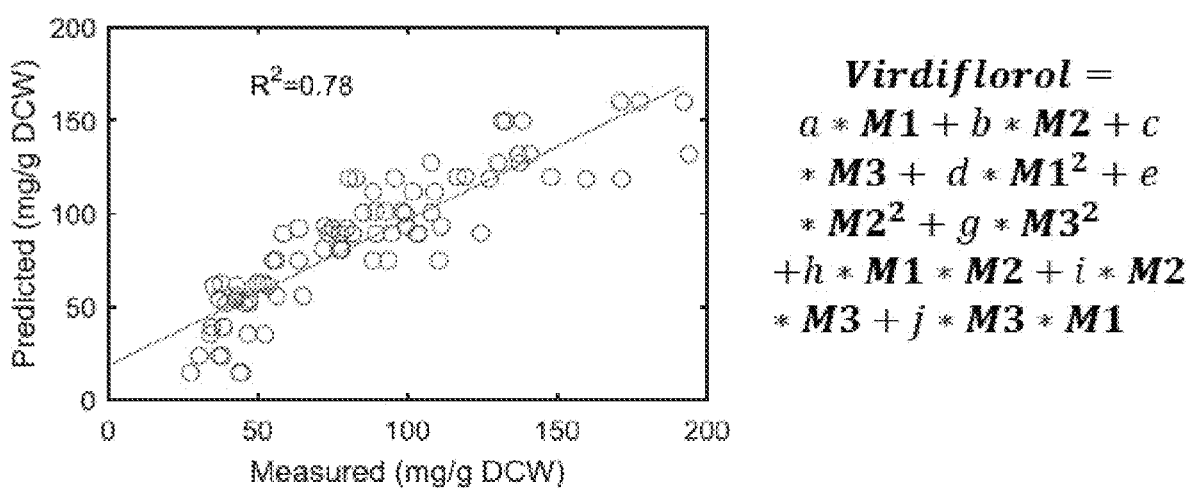
Figure 2C:
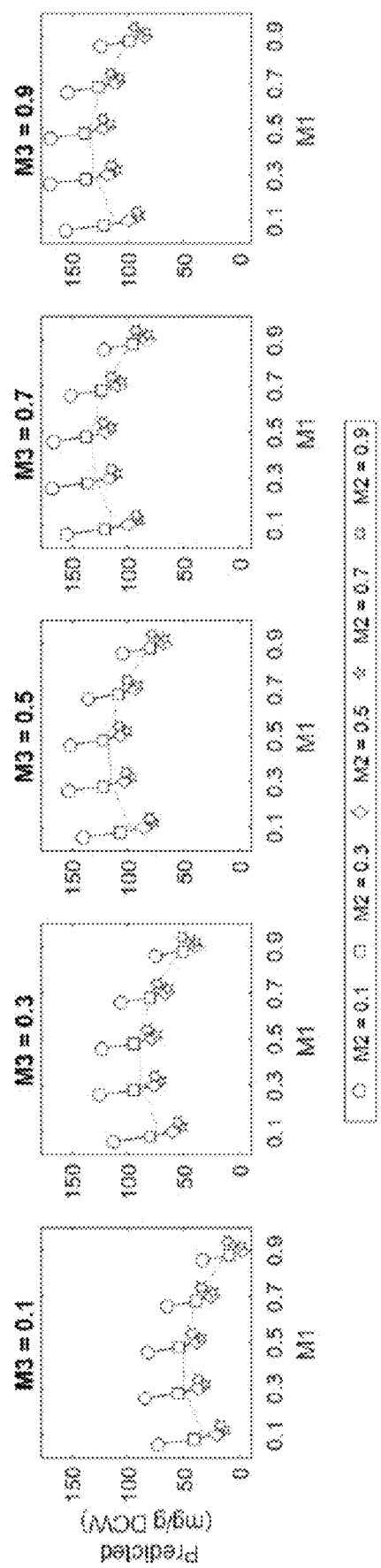
Figure 2D:
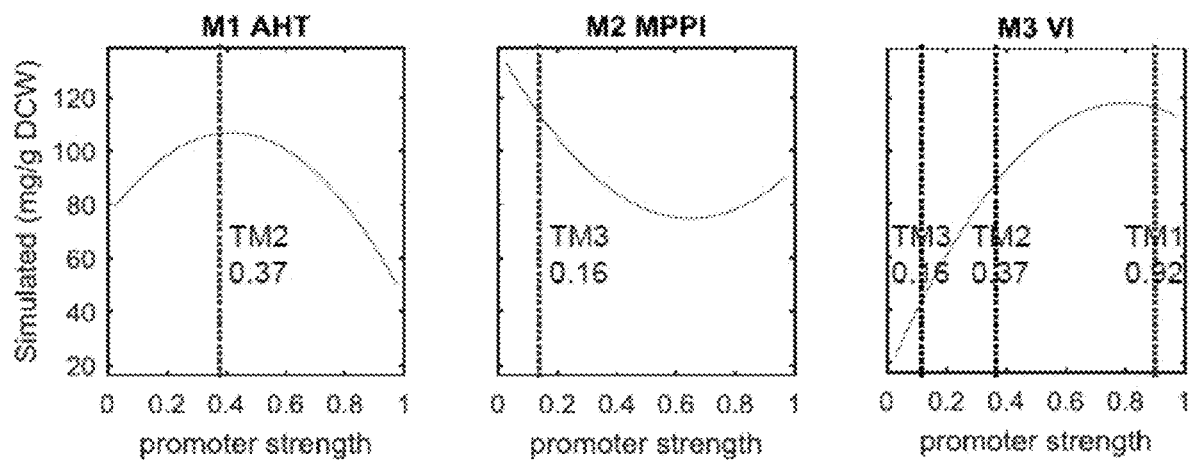
Figure 2E:
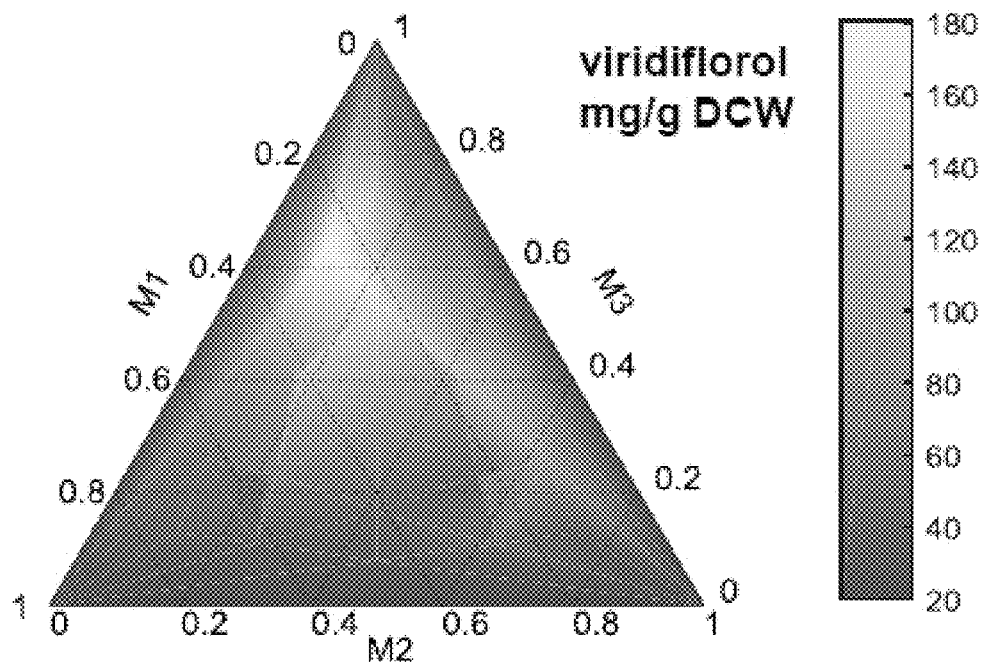
Figure 11:
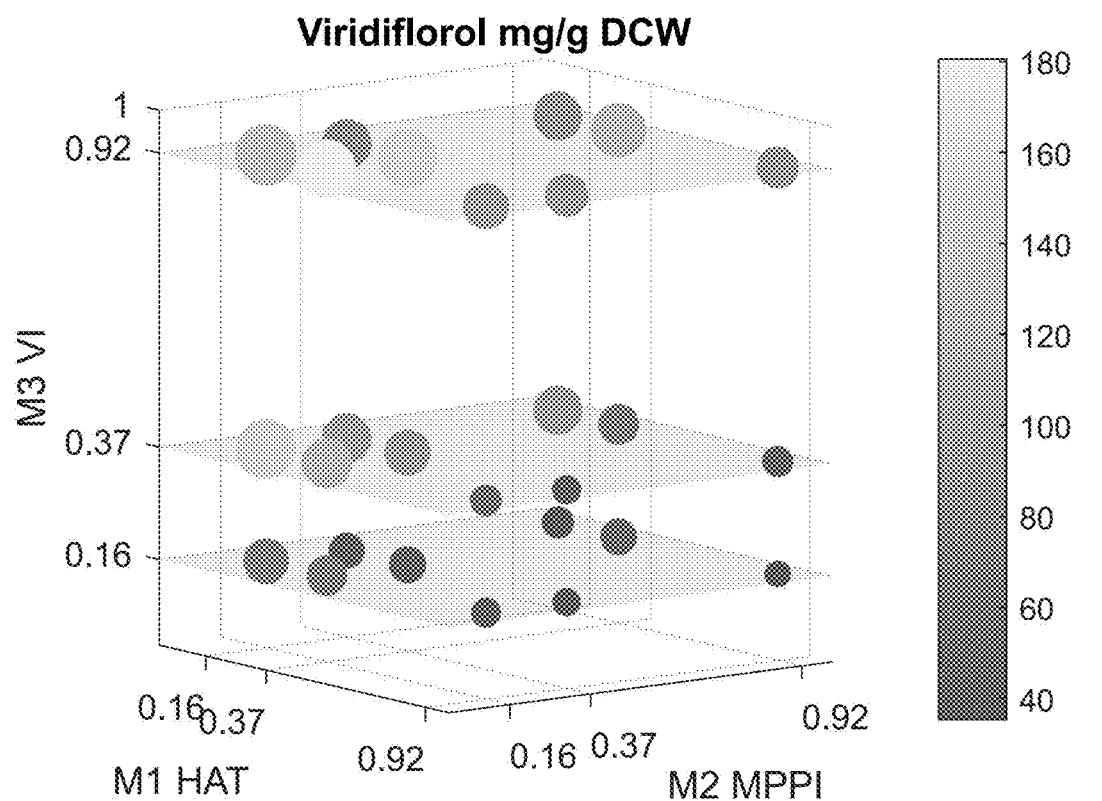
FIG. 11 shows the 4d plot and triplot of viridiflorol titre with the three modules. M1, M2, M3 referred to the promoter strengths (PS) of module 1, 2 and 3, respectively. The shade and size of the circles indicate the viridiflorol titres. Shade from dark to light: titres from low to high. Size from small to large: titres from low to high. Both figures represent the effect of the promoter strength of each module on viridiflorol titres.
Figure 11:
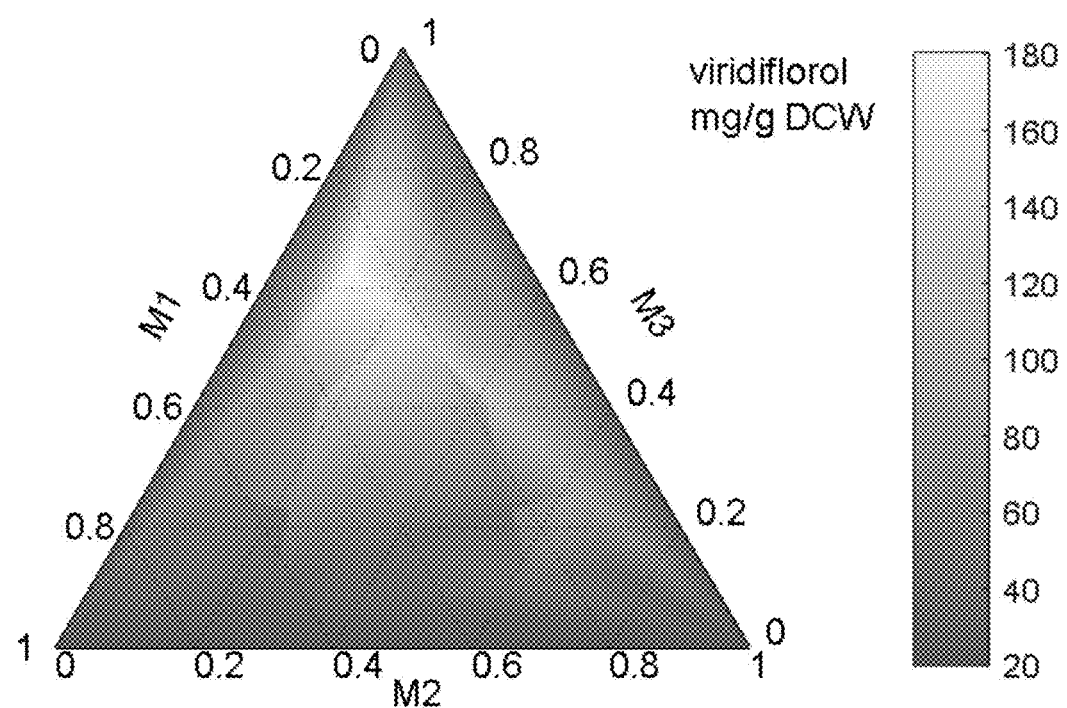

Thus, the 27 strains were tested with their own optimal inducer dosages (15 or 25 mM). Among them, the top three producers were strain #12, #21 and #24, where #12 produced the high amount of viridiflorol (specific yield 174±8 mg/g dry cell weight, or DCW, titre 275±12 mg/L, FIG. 2A and FIG. 11). The polynomial model was used to simulate and to predict the response (viridiflorol yields) over a range of input parameter values (M1, M2 and M3). The model fitted with the experimental data ($R^2=0.78$, FIG. 2B). Based on the model, viridiflorol production was positively correlated with M3 but negatively with M2. The predicted optimal values for M1, M2 and M3 were 0.4±0.1, 0.1±0.1 and 0.8±0.1, respectively (FIGS. 2C and D). Within the 27 strains, strain #12 (whose M1, M2 and M3 were, 0.37, 0.16 and 0.92, respectively) was closest to the optimal values. Indeed, #12 had the highest production, ~180 mg/g DCW or 283 mg/L (FIG. 2A and FIG. 11).

Example 2: Translational Optimization of Viridiflorol

Figure 3A:
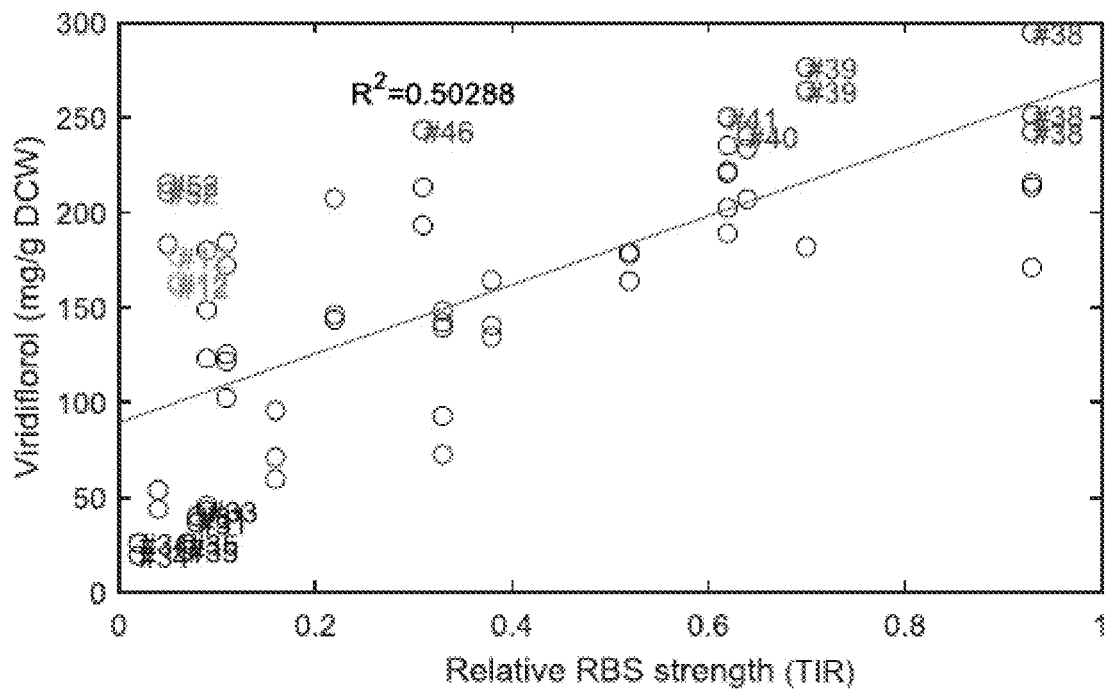
Figure 3B:
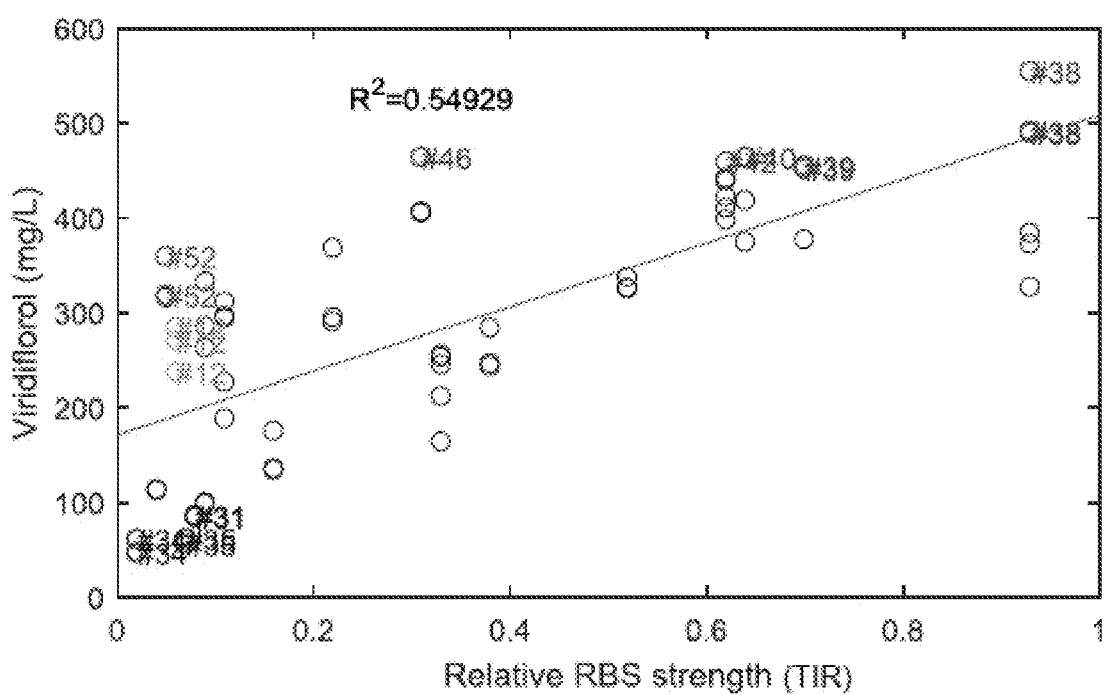
Figure 12:
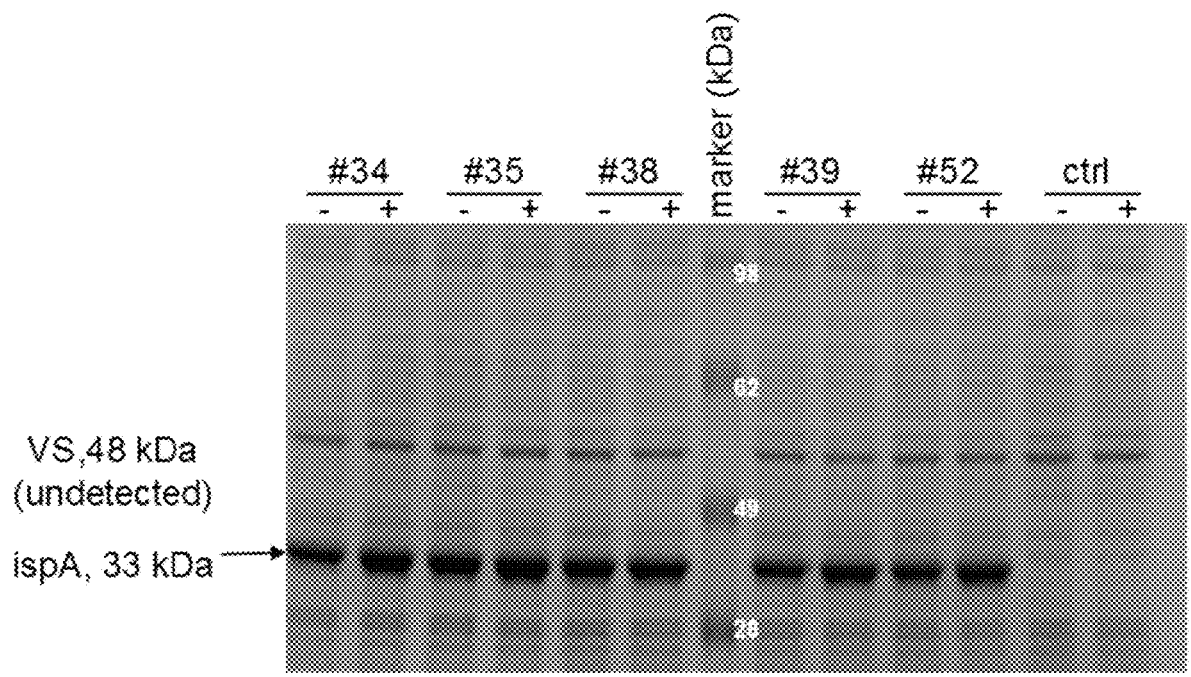
FIG. 12 shows a SDS-PAGE gel for the viridiflorol synthase (VS) with different-strength RBSs. IspA was co-expressed with VS in the same operon. VS, 48 kDa; IspA, 33 kDa.

Through the statistical analysis (FIGS. 2A-2E), it was observed that the viridiflorol yield was positively correlated with the transcription of module 3. This led to the hypothesis that the viridiflorol yield might be still limited by insufficient enzyme activities on module 3. Module 3 contains two enzymes, VS and ispA. IspA is a native *E. coli* enzyme with high expression and good activity, thus unlikely to be the limiting step. In contrast, as a fungal terpene synthase, VS was not even detectable in sodium dodecyl sulfate (SDS) polyacrylamide gel electrophoresis (PAGE) gel when co-expressed with ispA in the same operon (FIG. 12). Thus, the production was more likely to be limited by insufficient VS activity. To test this hypothesis, two ribosomal binding site (RBS) libraries for VS were designed that covered a broad range of translational initiation rates (TIRs) from 4000 to 18,206 a.u. (strains #31 to #52, FIGS. 3A-3D, here the TIRs were not experimental but in silico predicted values by RBS calculator, https-colon-forward-slash-forward-slash-salishlab.net/software/). Strain #12 (whose TIR was 11,608 a.u.), the top producer among the 27 strains, was used as the parental strain for translational optimization (strains #31 to #52). In line with the hypothesis, the tuning of the VS RBS had a marked effect on the viridiflorol production (FIGS. 3A and 3B). Among all the strains, the strain #38 produced the highest amount of viridiflorol (262±28 mg/g DCW, 511±37 mg/L), which was ~50% higher than its parental strain #12. A weak but positive correlation was observed between viridiflorol yields and the predicted TIRs ($R^2$=0.5 and 0.55 with specific yield and titres, respectively). The weak correlation could have had two possible explanations. Firstly, some of the predicted TIRs were not accurate; secondly, other unknown post-transcriptional effects may have led to the difference between experiment and prediction of VS. To test the first hypothesis, three representative groups of RBSs were chosen: #34 and #35 with low viridiflorol production and low TIRs; #52 with high viridiflorol production but low TIR; #38 and #39 with high viridiflorol yield and high TIRs. VS band (48 kDa) was not observed in the SDS-PAGE gels for any of them, despite the ispA (the polycistronic gene of VS) band (33 kDa) being quite distinct (FIG. 12).

Example 3: Enzyme Engineering of Viridiflorol Synthase

Figure 4A:
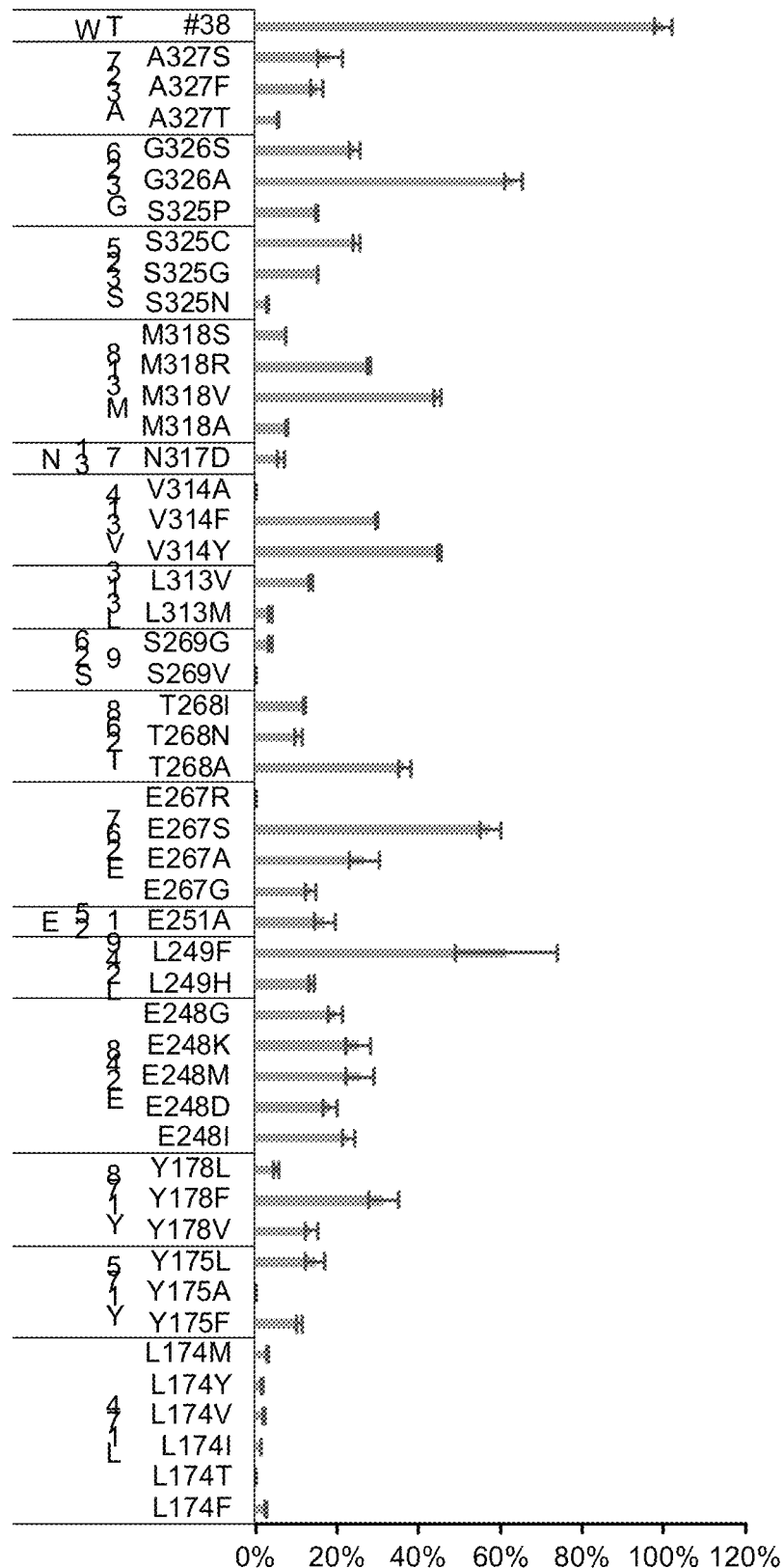
FIGS. 4A-4E show viridiflorol synthase (VS) mutation for improved activity.
Figure 4B:
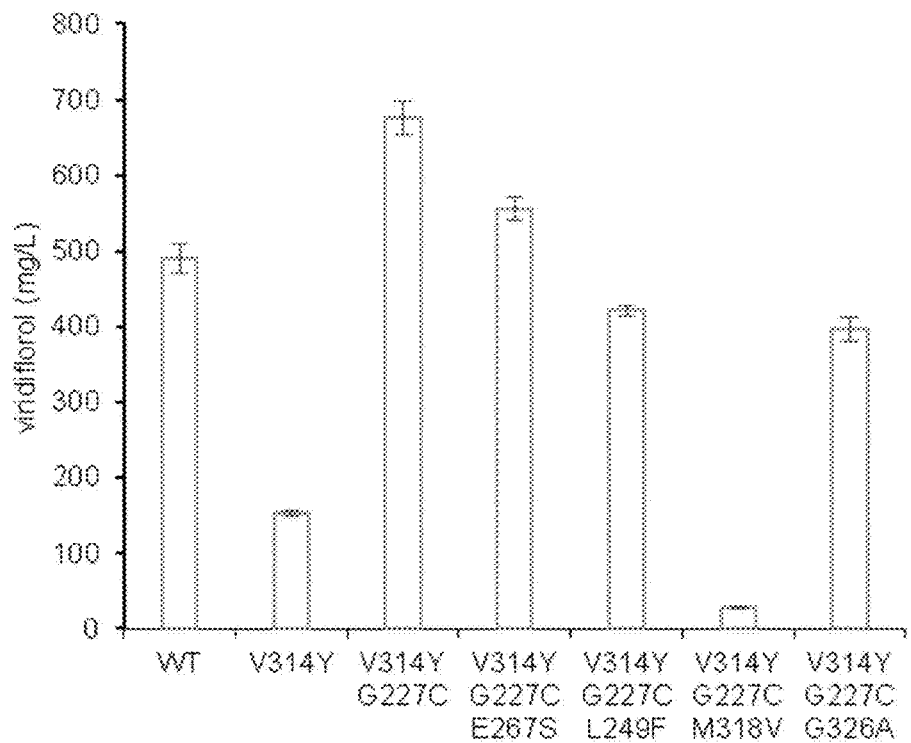
Figure 4C:
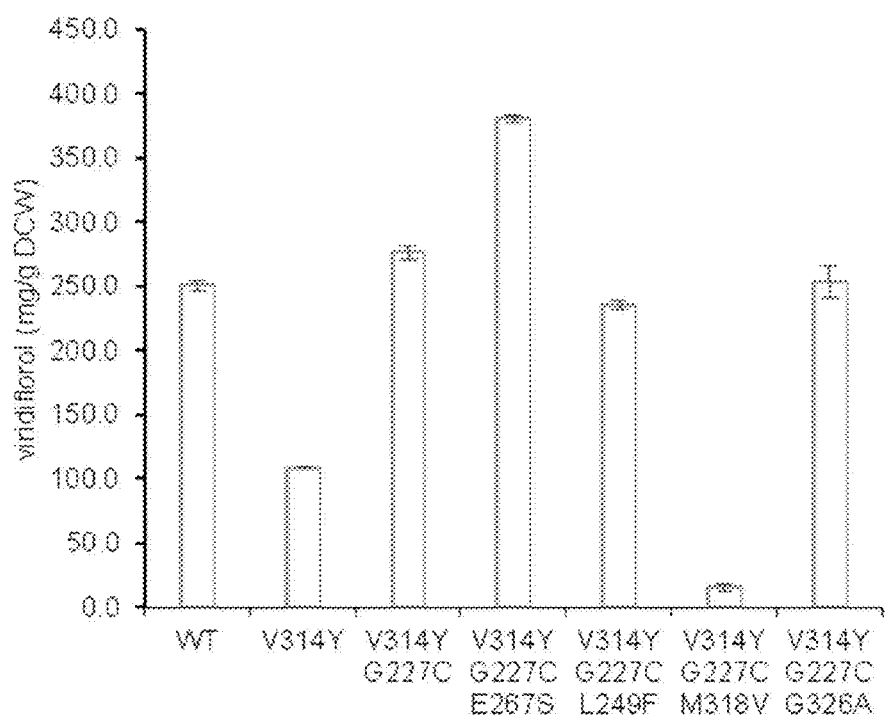
Figure 4D:
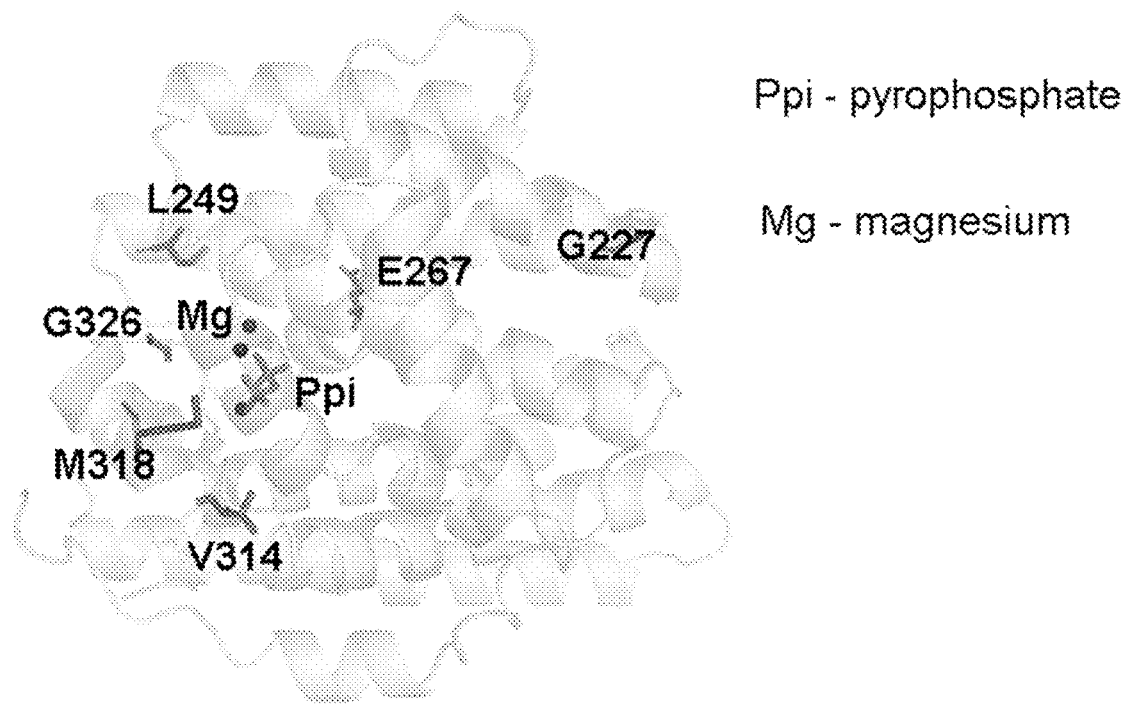
Figure 4E:
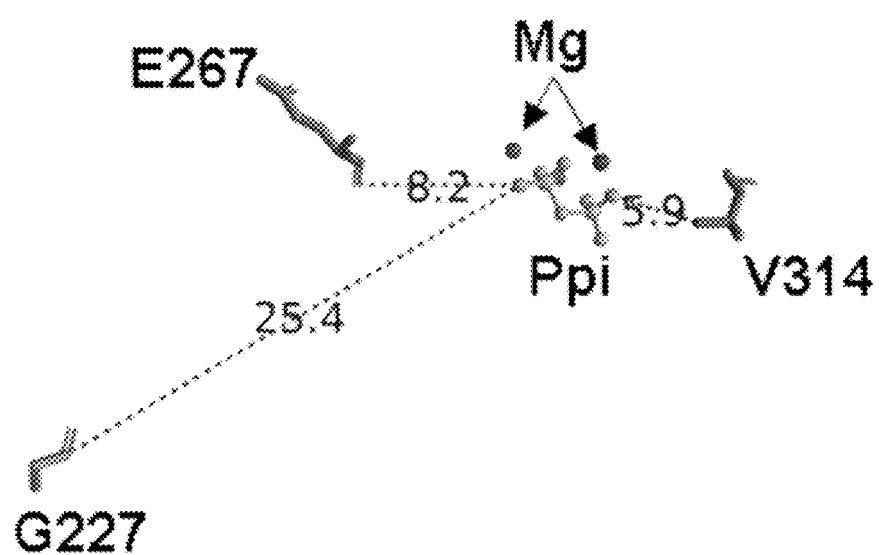
Figure 13:
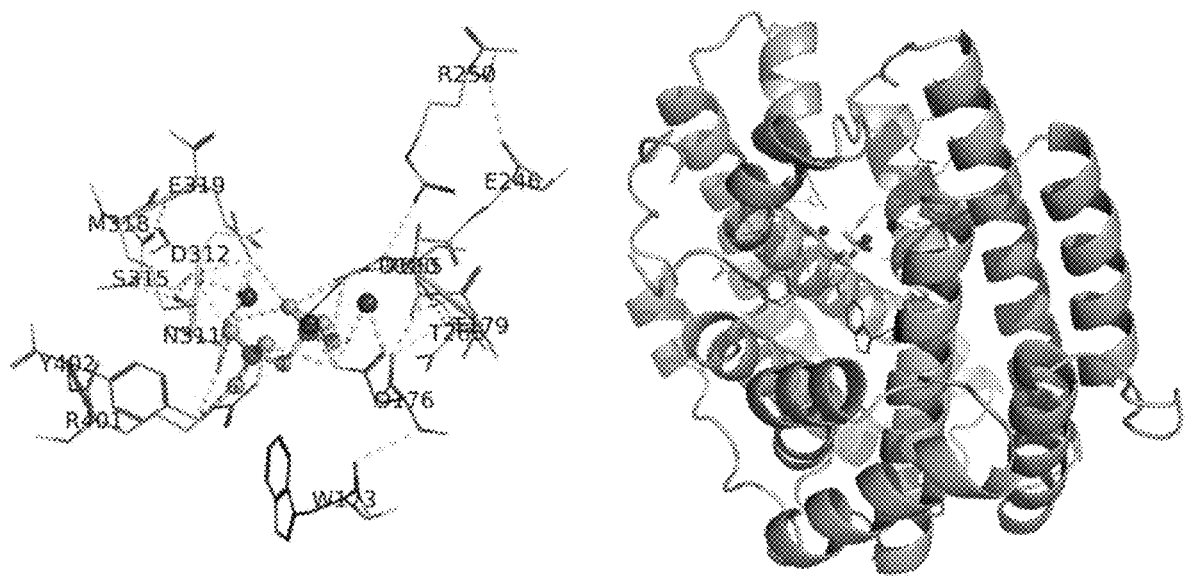
FIG. 13 shows a homologue model of VS and the predicted active sites. The ligand pyrophosphate was shown in salmon colour and magnesium was in firebrick colour. Hydrogen bonds among substrates, cofactors and active sites were shown in yellow dash lines.
Figure 14:
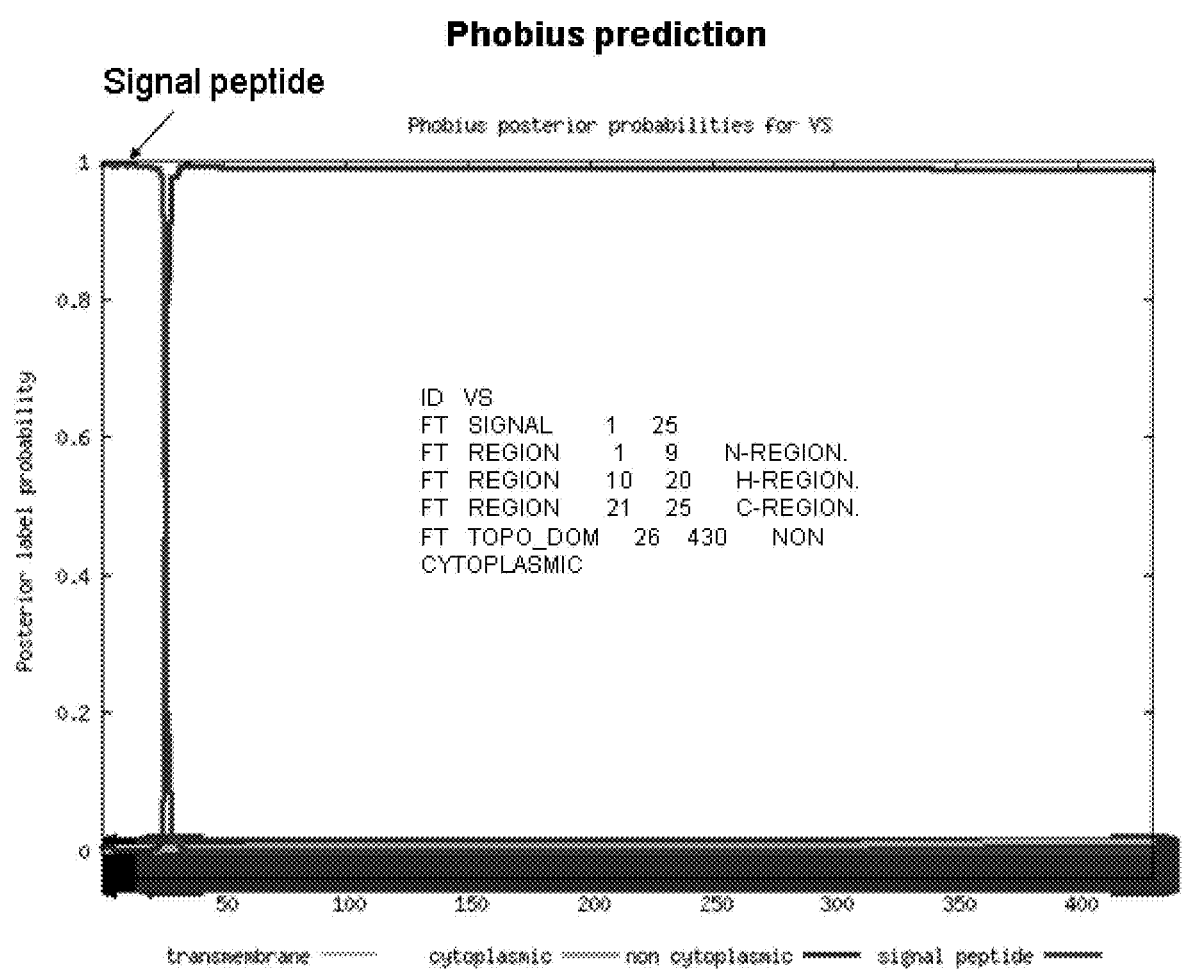
FIG. 14 shows transmembrane topology and signal peptide prediction for VS using Phobius and Signal P 4.1 server. Both of the two webtools predicted there is a signal peptide region for VS. The S-score is signal peptide score, and those amino acids above the threshold are predicted to be within the signal peptide region.
Figure 14:
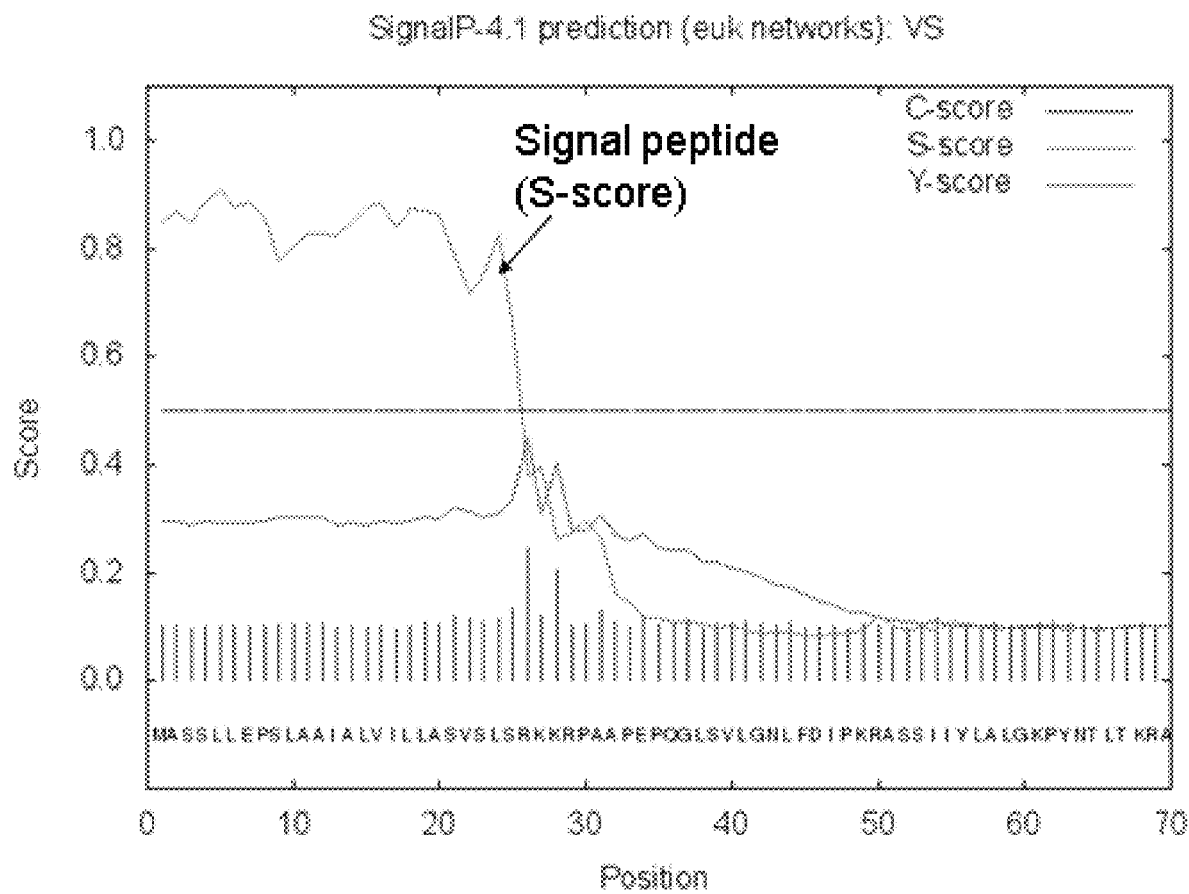

After the study of transcriptional and translational optimization, it was observed that the insufficient VS activity limited the viridiflorol production. The synthetic biology toolboxes used to this point were unable to resolve this flux limitation beyond what had been obtained. To overcome it, enzyme engineering approaches were further explored. A homologue model of the fungal VS was built based on the structure of epi-isozizaene synthase (PDB ID: 4ltz). With pyrophosphate (POP) and magnesium (Mg) as ligand, the amino acids in the binding pocket were shown in FIG. 13. A BLAST search was carried out with VS as the template in UniProt (https-colon-forward-slash-forward-slash-www.uniprot.org/) and Joint Genome Institute fungal database (JGI, https-colon-forward-slash-forward-slash-jgi.doe.gov/). Fourteen putative fungal terpene synthases were identified that share high similarity with the VS, or AAE3_13291 (FIG. 14). Based on the homologue model and the alignment of the 15 enzymes, a small library was designed to target 16 sites which were positioned, either in vicinity of active sites, or the conserved regions (such as magnesium binding motifs). Instead of using saturation mutation, phylogeny-based mutation with the 15 enzymes (FIG. 4A) was chosen due to the lack of a suitable high-throughput screen. However, all the chosen 48 single mutations were less active than the wild type. Specifically, L174 was critical for VS activity, all 6 mutations (L174M, L174Y, L174V, L174I, L174T and L174F) at the positions reduced viridiflorol production by >95%. L174 is positioned in vicinity of "DEYTD" (magnesium binding motif), hence its mutation could affect the binding of cofactor and thus reduced the activity. As the targeted mutation was not successful, random mutations were introduced to VS by error-prone PCR. By screening ~400 colonies, one VS mutant was found to have higher viridiflorol production. Sequencing results indicated the mutant had two mutations G227C and V314Y. Despite that V314Y single mutation reduced the viridiflorol production by over 50%, V314Y and G227C together improved the viridiflorol titre by over 38% (FIG. 4B). Unlike V314 that is located in the substrate binding pocket, G227 is distant from the active sites (FIGS. 4D and 4E). On top of this double mutant, other mutations, L249F, E267S, M318V and G326A, which were the best 4 mutations in FIG. 4A, were further introduced. Among the four triple mutants, V314Y-G227C-E267S increased viridiflorol specific yield by 52% over wildtype, despite a diminished final cell density (~17% lower than the wildtype: FIGS. 4B and 4C). However, the mutant V314Y-G227C-M318V remarkably reduced viridiflorol yield over 90%.

Figure 5A:
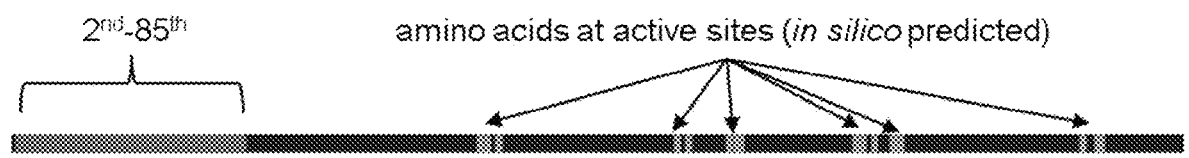
FIGS. 5A-5D show the combination of truncation and mutation of VS with auxotrophic design.
Figure 5B:
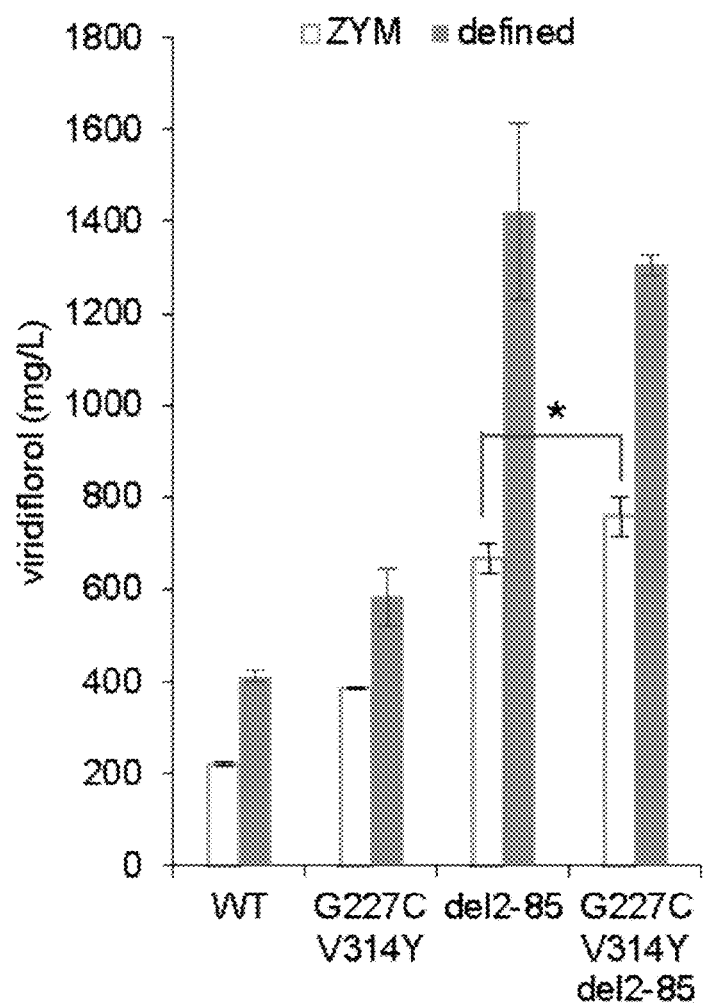
Figure 5C:
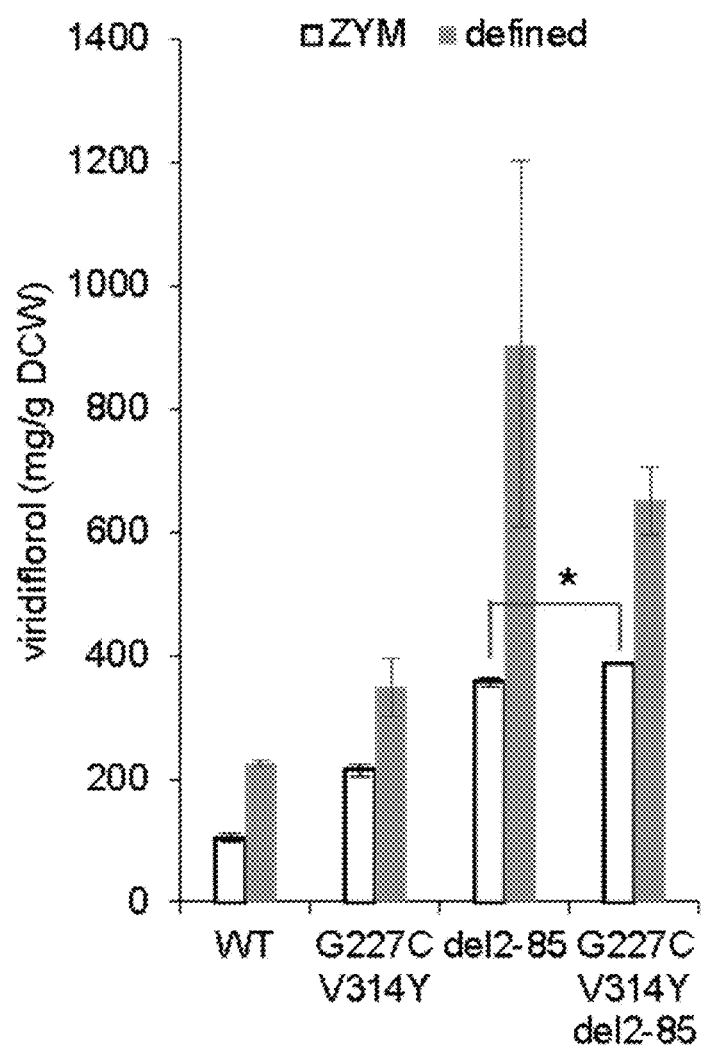
Figure 5D:
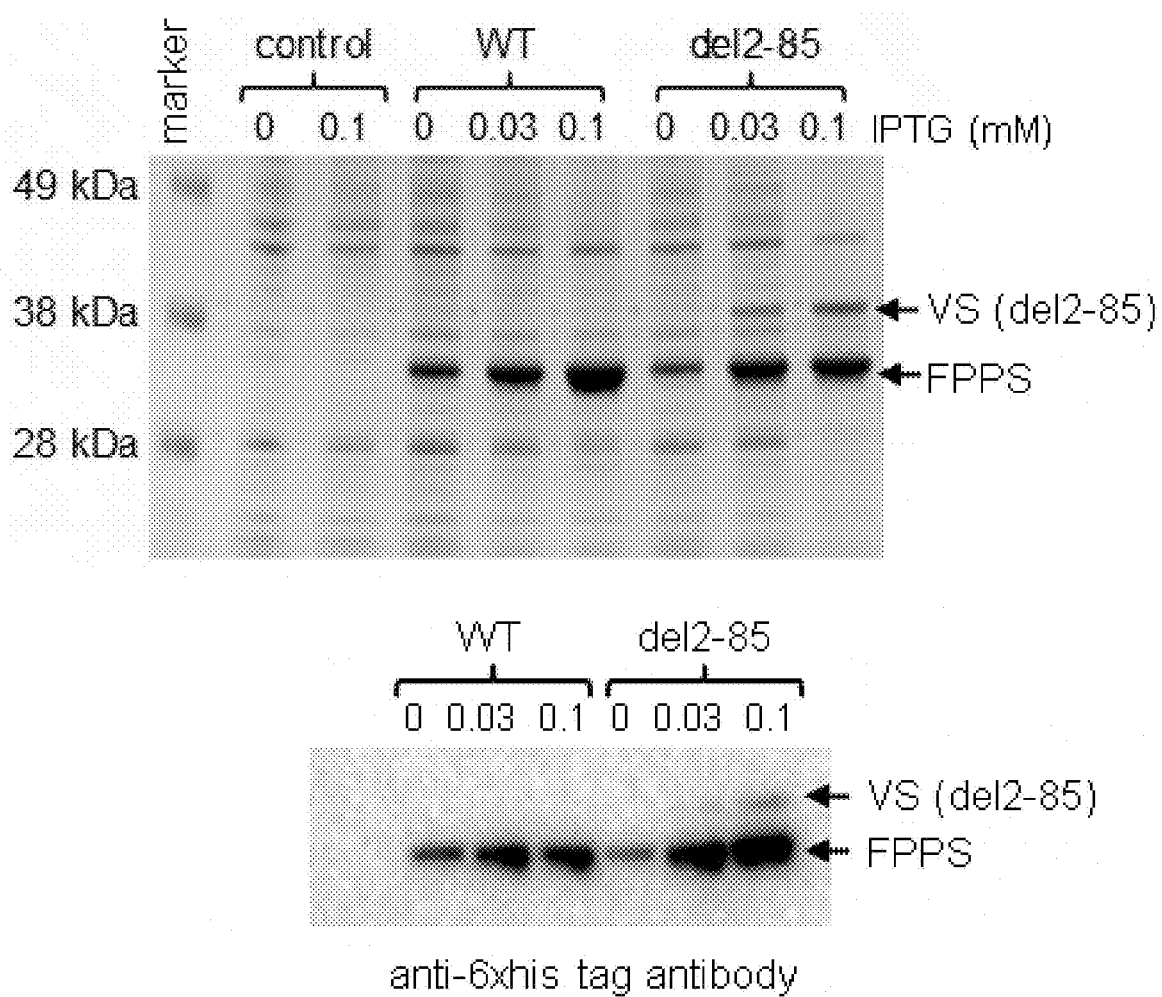
Figure 15A:
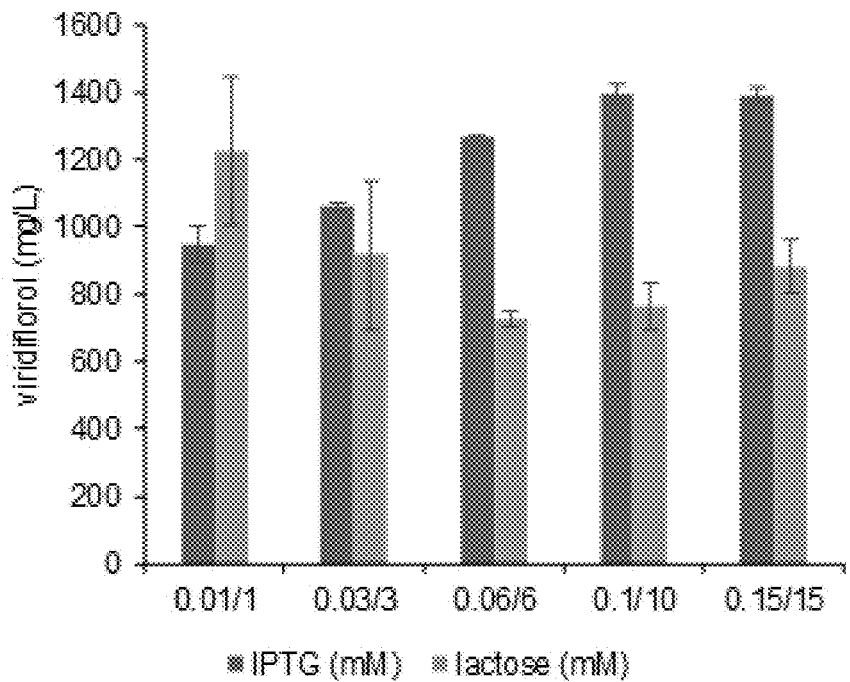
FIGS. 15A-15C show inducer titration for viridiflorol production of the strain del2-85 (truncated VS).
Figure 15B:
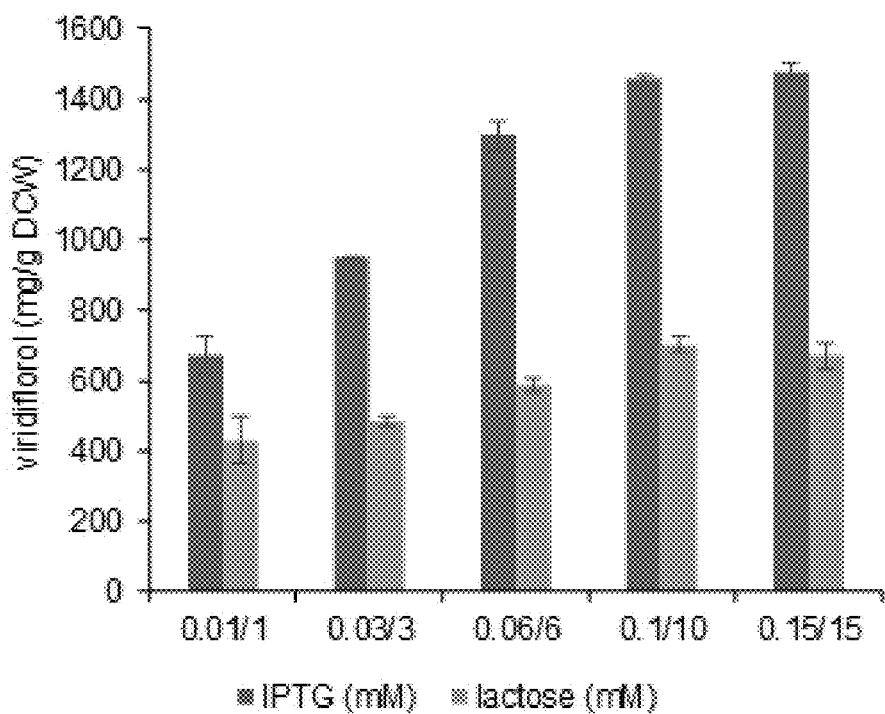
Figure 15C:
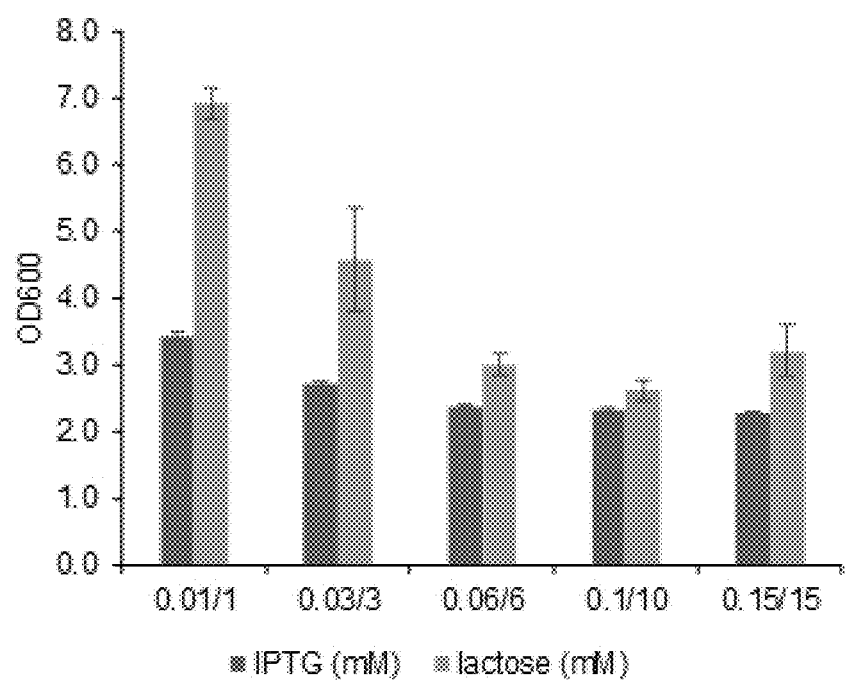

During the alignment with its closely-related fungal terpene synthases, it was observed that the VS had about additional 80 amino acids in N terminus over others (FIG. 14). Further study by signal peptide prediction programs SignalP (https-colon-forward-slash-forward-slash-www.cbs.dtu.dk/services/SiqnalP/) and Phobius (https-colon-forward-slash-forward-slash-phobius.binf.ku.dk/) confirmed the possibility of N-terminal signal peptide in the VS (FIGS. 15A-15C). The N-terminal signal peptide region may negatively affect the expression and would direct VS to E. coli membrane which could reduce the contact with its substrate in cytosol. The latter hypothesis could also explain why wildtype VS was invisible in protein gel as membrane proteins are known to be less accessible. Hence, it was hypothesized that the truncation of this region could be beneficial to viridiflorol production. The $2^{nd}$-$85^{th}$ amino acids were then removed from N terminus of the wildtype and the double mutant G227C-V314Y (FIG. 5A). As a result, the truncation markedly increased the viridiflorol titres and specific yields by about 200% and 100% for the wildtype and the mutant VS, respectively (FIGS. 5B and 5C). In addition, the combination of truncation and enzyme mutation had synergistic effects on viridiflorol production in ZYM rich media. Consistent with the hypothesis that the wildtype VS was invisible in SDG-PAGE gels due to the N-terminal signal peptide sequence, the truncated version del2-85 (39.2 kDa) was clearly detected and was further confirmed by western blot with anti-6× his tag antibody (FIG. 5D).

Example 4: Auxotrophic E. coli and Fed-Batch Fermentation of Viridiflorol

Complex medium is often subject to batch-to-batch variation and is expensive. Therefore, in large scale industrial fermentation, chemically defined media is favoured. More importantly, it was observed that biological replicates occasionally had very different results and it was likely to stem from plasmid instability, especially for the plasmid carrying the module MPPI based on the results of restriction enzyme mapping. To solve it, an auxotrophic E. coli strain was created by deleting three aromatic-amino-acid synthesis genes (aroA, aroB and aroC) from the genome. The genes were subsequently grafted into the three plasmids, respectively. Hence, this engineered strain was forced to maintain the plasmids as there was no amino acid in the defined media. Indeed, good stability was achieved for the auxotrophic strains even without antibiotics (FIGS. 17A-17D).

Figure 16:
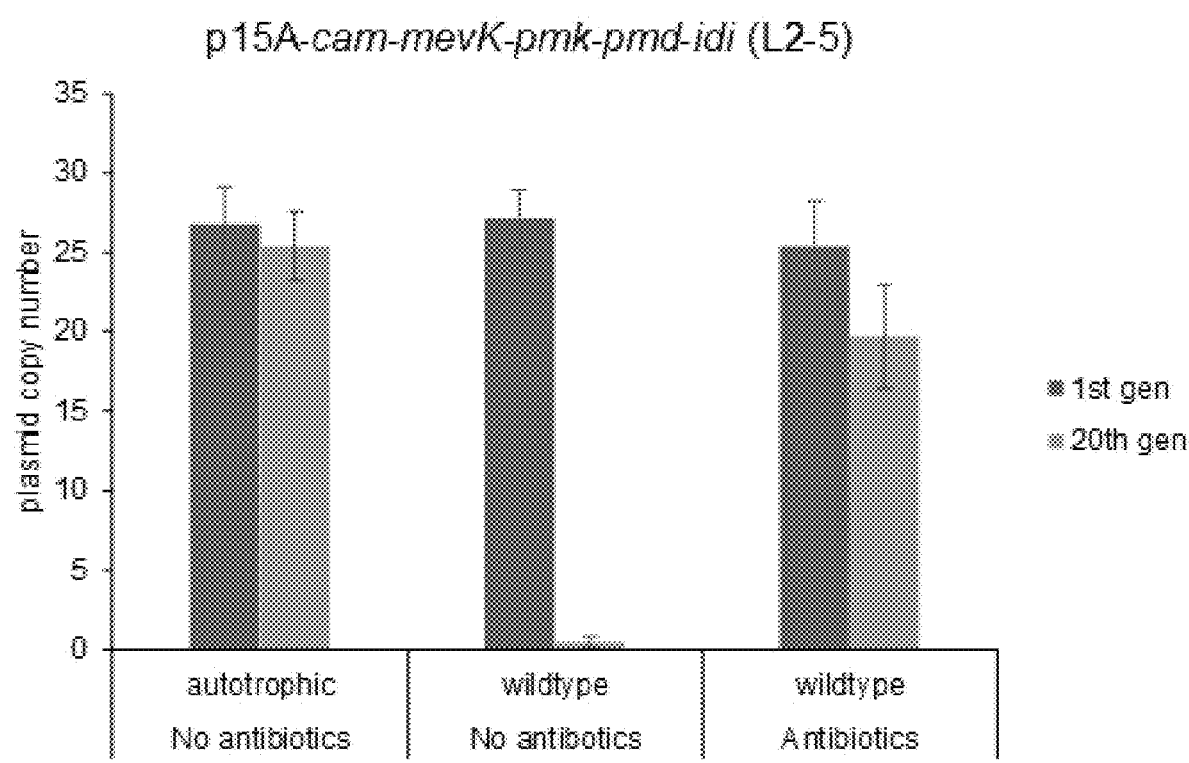
FIG. 16 shows the result of plasmid stability checking. The wildtype and auxotrophic strains were grown in chemically defined media with or without the use of antibiotics. After ~20 generation, the plasmid copy numbers were measured by qPCR and compared with those of the first generations. Here, the p15A-cam-mevK-pmk-pmd-idi(L2-5) was chosen as it was found to be the most unstable. The data here indicated the auxotrophic strain had better stability over the wildtype strain. The qPCR primers for the plasmids were rt-mk-890-f and rt-mk-985-r. The primers for genomic DNA were cysG-f/r (Table 1). The plasmid copy numbers were calculated as the ratio of the copy numbers of plasmid gene and the genomic gene.
Figure 17A:
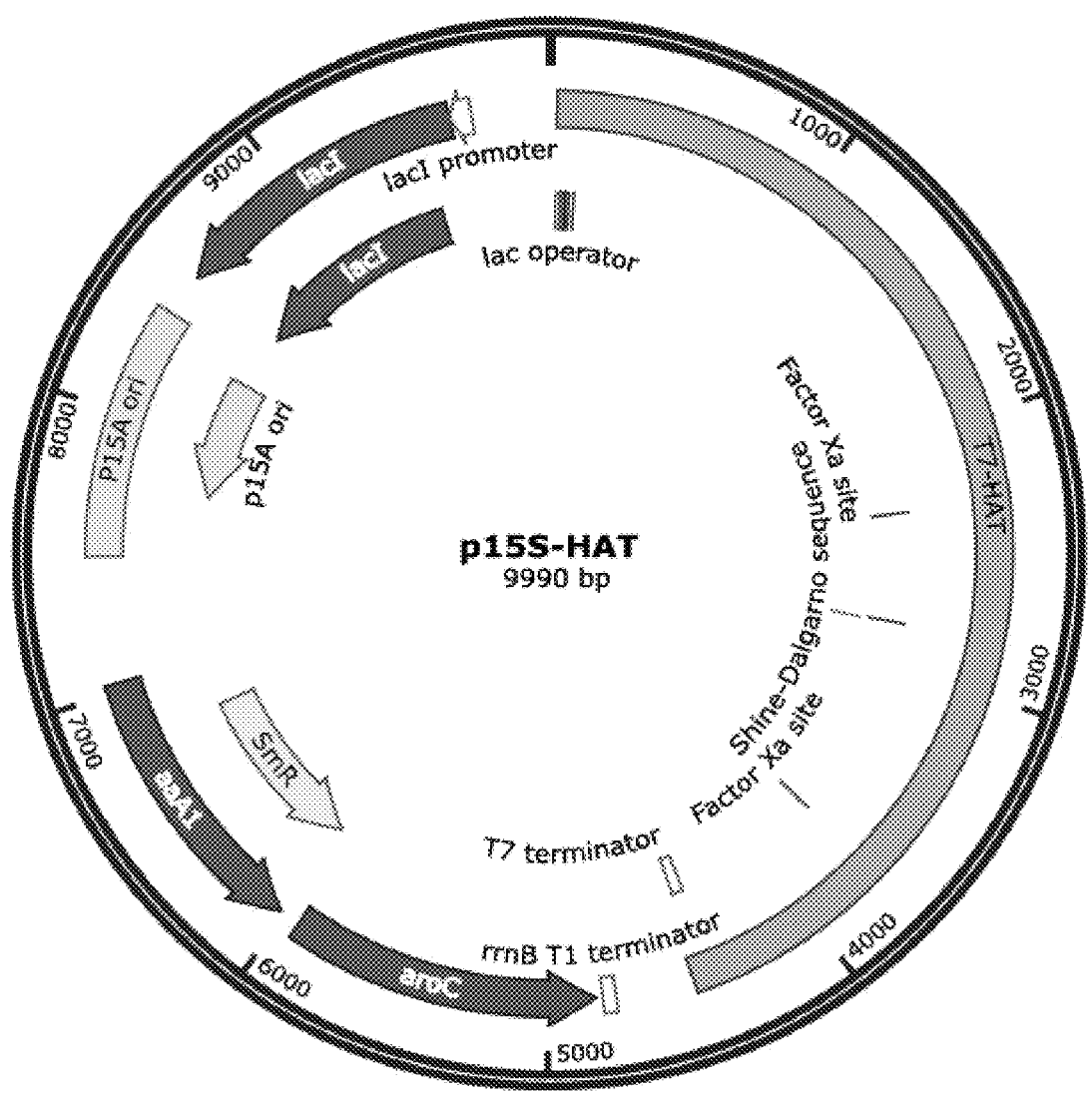
FIGS. 17A-17D show plasmid maps of vectors used.
Figure 17B:
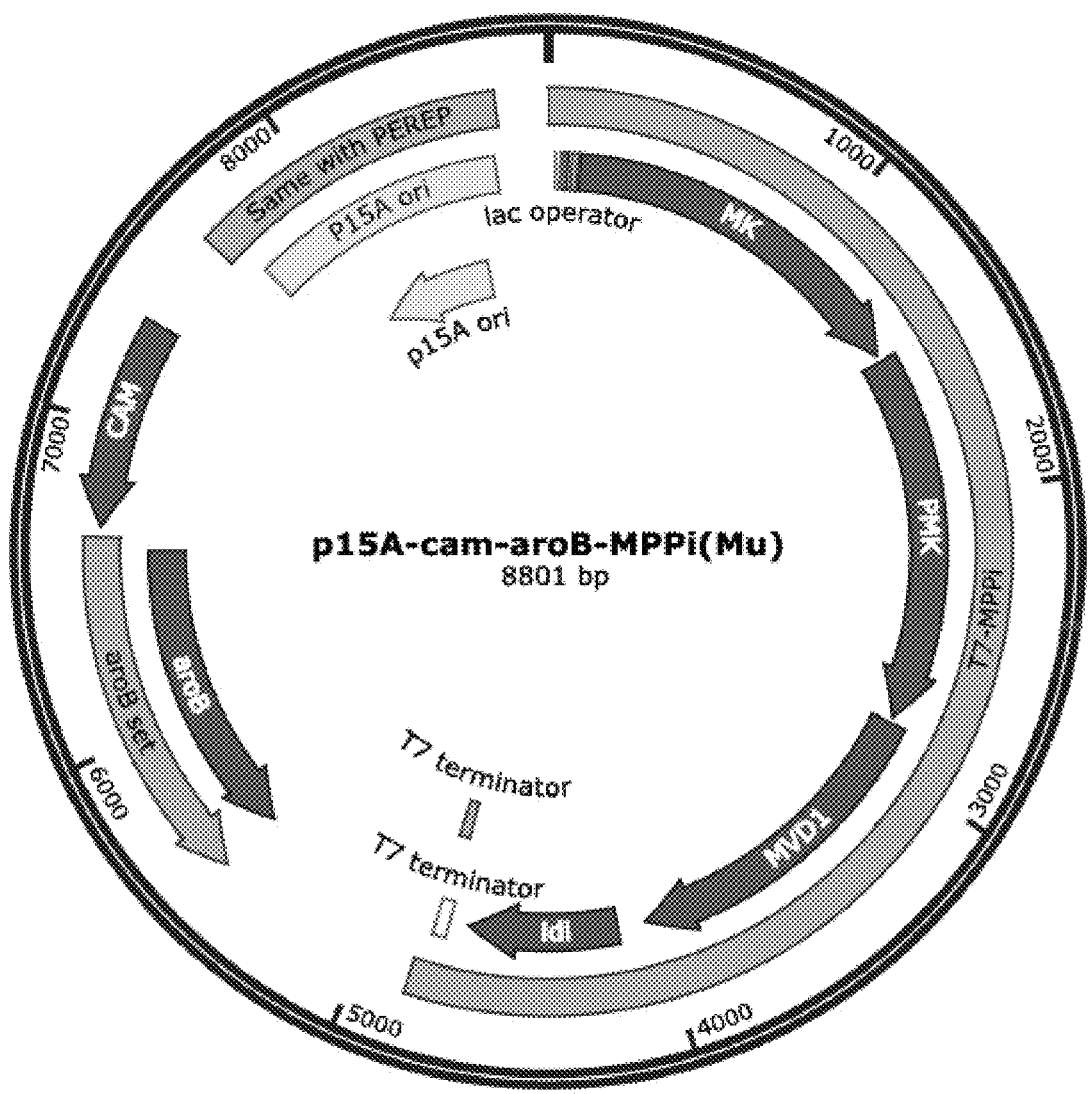
Figure 17C:
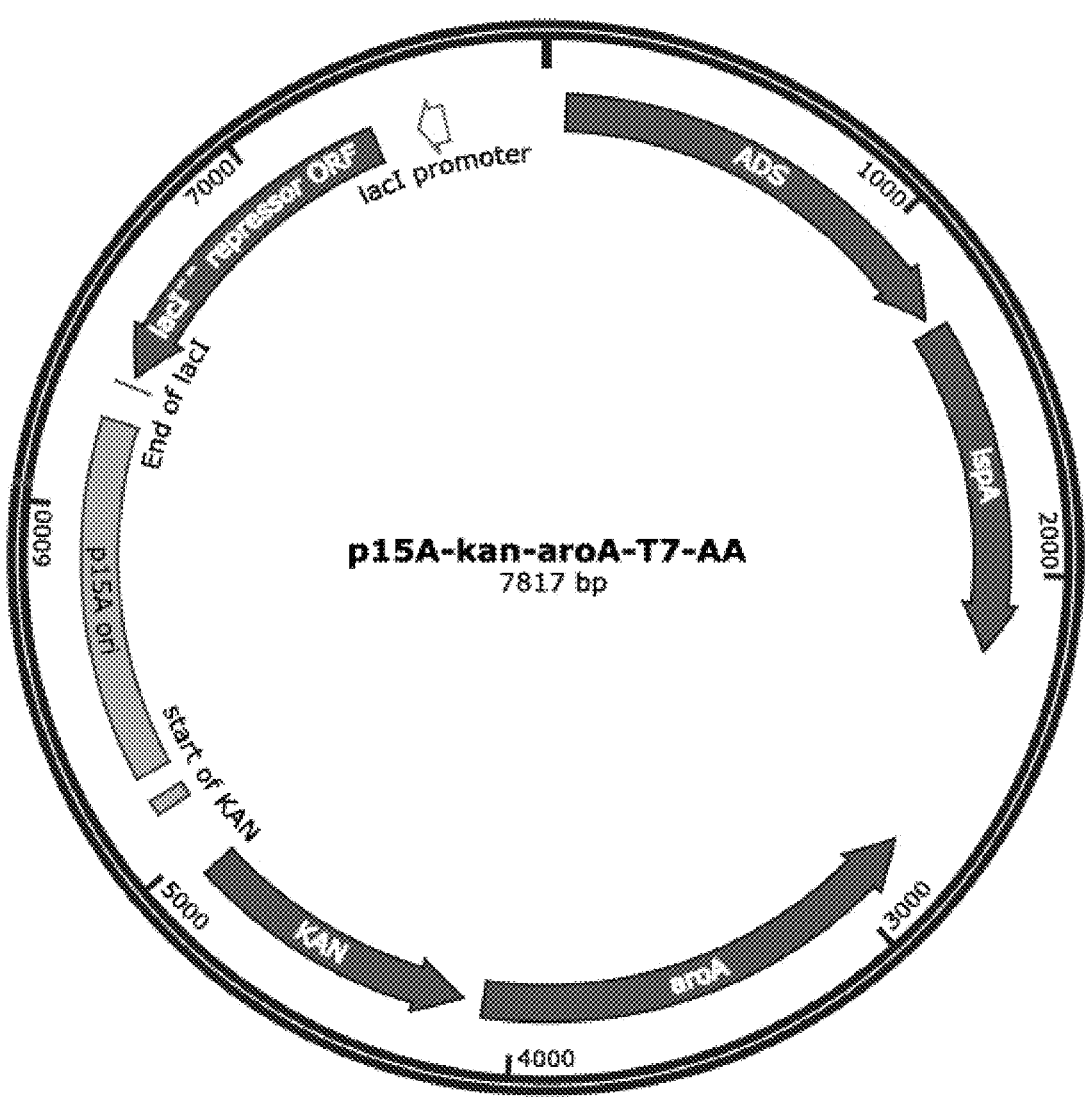
Figure 17D:

All the four strains (WT, G227C-V314Y, del2-85, and the combination of de2-85 with G228C-V314Y) had higher production in the defined media as compared with the rich media. However, the synergistic effect of the truncation and the targeted mutation was no longer observed. The underlying reason was unknown and worth further study. A possible reason was that the achieved yield was no longer limited by VS activity but by other factors (e.g. cofactor availability) so that the synergistic benefit could not be visualized. The strain del2-85 had a slightly higher viridiflorol yield than the strain of de2-85 with G227-V314Y (FIGS. 5B and 5C). The titration results indicated the specific yields gradually increased as the concentration of IPTG increased (FIG. 16). When induced by 0.1 mM IPTG, the cells produced 1.4 g/L viridiflorol and 1.4 g/L of dry cells from 10 g/L glucose.

Example 5: Fed-Batch Fermentation

Figure 6A:
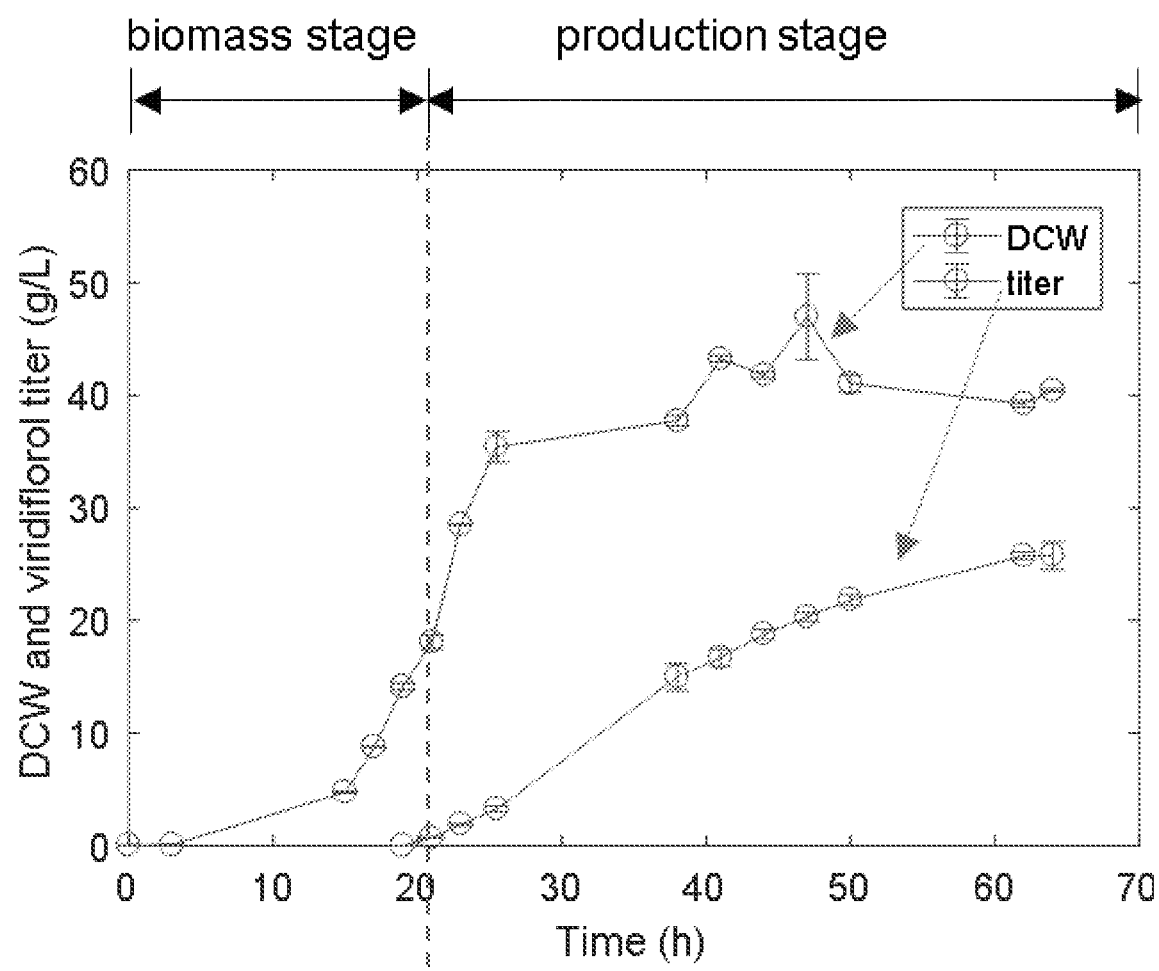
FIGS. 6A-6C show the fed-batch fermentation of viridiflorol and amorphadiene.
Figure 6B:
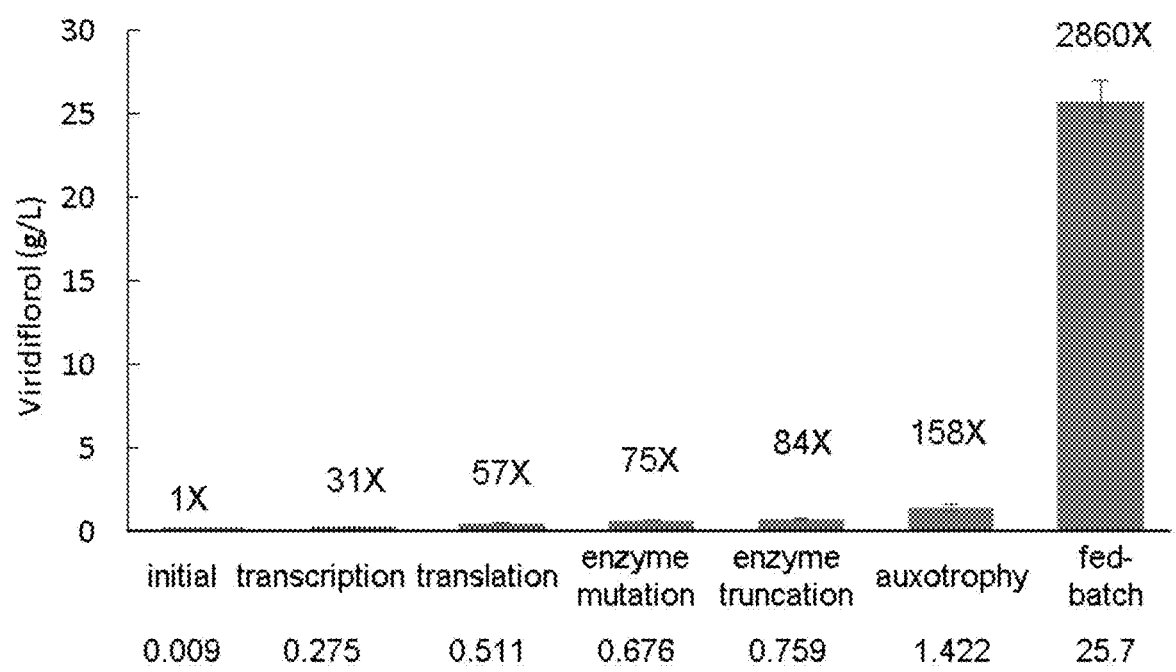

The performance of del2-85 strain in fed-batch fermentation was tested using the chemically defined media. The cells were induced at the mid stage ($OD_{600}$ of 35). Within 62 hours, the strain produced 25.7 g/L of viridiflorol and 41 g/L of DCW. Hence, the productivity was about 0.42 g/L/h. The total glucose used in the whole process was 151 g/L, where it consisted of two stages: biomass stage and production stage (FIG. 6A). Viridiflorol was only produced in production stage and at this stage the glucose consumed was 115 g/L, therefore the carbon yield was 0.22 g/g glucose, about 81% of its theoretical yield of the mevalonate pathway (27.4%, 4.5 mole of glucose to 1 mole of viridiflorol). It had to be highlighted that the theoretical yield, which was calculated based on zero-growth condition, cannot practically achieved in fed-batch fermentation where cells were still growing. Collectively with transcription, translation, enzyme, strain and process optimization, the viridiflorol titre was increased by 2860 fold, from 0.009 to 25.7 g/L (FIG. 6B).

Example 6: Expending the Knowledge Gained to Other Isoprenoids

Figure 6C:
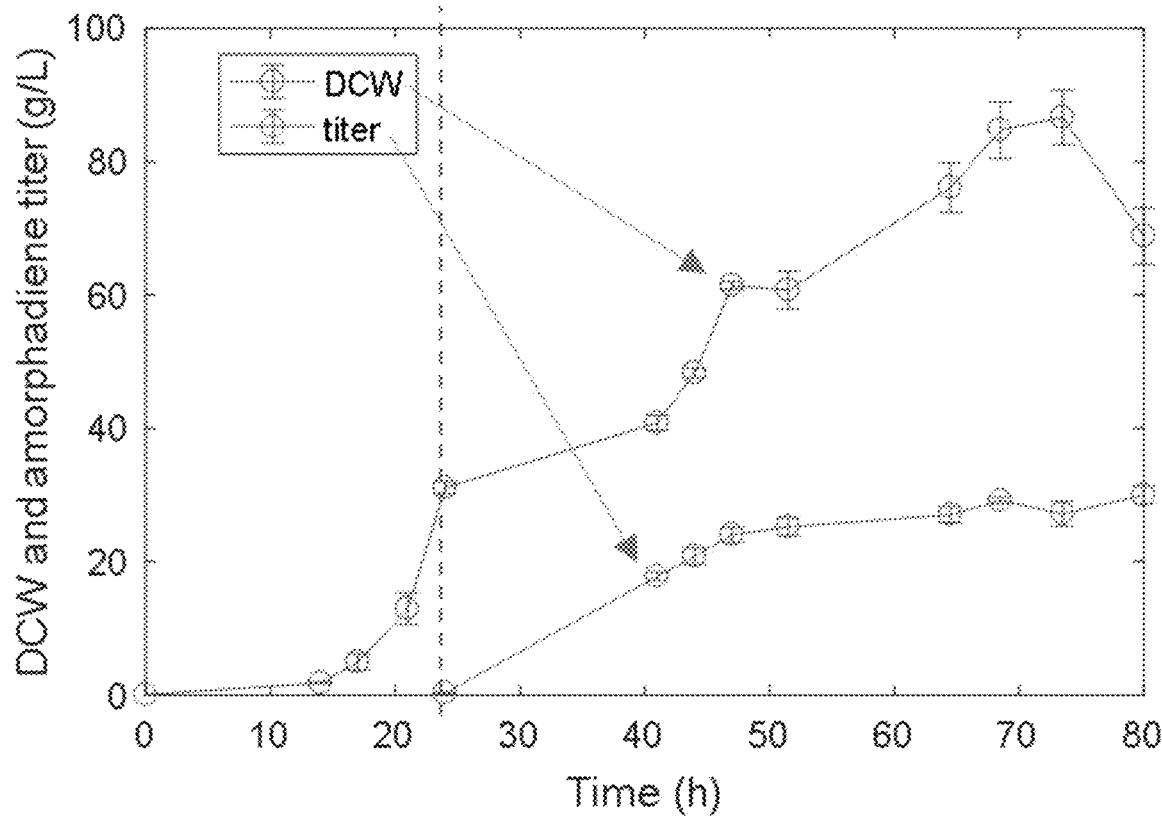

To test if the transcriptional model in FIGS. 2A-2E can be used to optimize other terpenoids, *amorpha*-4,11-diene, the precursor to the potent antimalarial drug artemisinin, was chosen. Until recently, malaria still causes ~440,000 deaths each year. Both *amorpha*-4,11-diene and viridiflorol are sesquiterpenes and they share the same metabolic pathway except for the terpene synthase (FIGS. 1A-1E). Thus, *amorpha*-4,11-diene is an ideal example to test the predictive feature of the model and the performance of the optimized strain. Without having to test many combinatorial pathway designs and inducer conditions, a strain was obtained that produced 1.2 g/L of *amorpha*-4,11-diene at batch fermentation. Using the same fermentation media and process as to viridiflorol, this strain produced 30 g/L of *amorpha*-4,11-diene in 80 hours with a carbon yield of 0.19 g/g glucose (FIG. 6C). The carbon yield achieved is ~75% of its theoretic yield (25.2%, 4.5 mole of glucose to 1 mole of *amorpha*-4,11-diene). Though the fermentation processes have not been fully optimized, the titres, production rates and yields ('TRY') for both viridiflorol and *amorpha*-4,11-diene here were comparable to the excellent results of Amyris Inc's artemisinic acid (25 g/L in 140 h) and higher than most of the previously reported 'TRY' data of terpenoid production in engineered microbes (1.5 g/L sclareol in 60 h, 323 mg/L nerolidol in 48 h) and plants.

TABLE 4

Summary of sequence listing.

| Description | SEQ ID NO |
| --- | --- |
| Nucleic acid sequence of RBS of Strain #12 | 1 |
| Nucleic acid sequence of RBS of Strain #31 | 2 |
| Nucleic acid sequence of RBS of Strain #32 | 3 |
| Nucleic acid sequence of RBS of Strain #33 | 4 |
| Nucleic acid sequence of RBS of Strain #34 | 5 |
| Nucleic acid sequence of RBS of Strain #35 | 6 |

TABLE 4-continued

Summary of sequence listing.

| Description | SEQ ID NO |
| --- | --- |
| Nucleic acid sequence of RBS of Strain #36 | 7 |
| Nucleic acid sequence of RBS of Strain #37 | 8 |
| Nucleic acid sequence of RBS of Strain #38 | 9 |
| Nucleic acid sequence of RBS of Strain #39 | 10 |
| Nucleic acid sequence of RBS of Strain #40 | 11 |
| Nucleic acid sequence of RBS of Strain #41 | 12 |
| Nucleic acid sequence of RBS of Strain #42 | 13 |
| Nucleic acid sequence of RBS of Strain #43 | 14 |
| Nucleic acid sequence of RBS of Strain #44 | 15 |
| Nucleic acid sequence of RBS of Strain #45 | 16 |
| Nucleic acid sequence of RBS of Strain #46 | 17 |
| Nucleic acid sequence of RBS of Strain #47 | 18 |
| Nucleic acid sequence of RBS of Strain #48 | 19 |
| Nucleic acid sequence of RBS of Strain #49 | 20 |
| Nucleic acid sequence of RBS of Strain #50 | 21 |
| Nucleic acid sequence of RBS of Strain #51 | 22 |
| Nucleic acid sequence of RBS of Strain #52 | 23 |
| Amino acid sequence of wildtype VS | 24 |
| Amino acid sequence of full-length hmgR | 25 |
| Amino acid sequence of truncated hmgR | 26 |
| Nucleic acid sequence of promoter T7 | 27 |
| Nucleic acid sequence of promoter TM1 | 28 |
| Nucleic acid sequence of promoter TM2 | 29 |
| Nucleic acid sequence of promoter TM3 | 30 |
| aroA-F | 31 |
| aroA-R | 32 |
| aroC-F | 33 |
| aroC-R | 34 |
| aroB-F | 35 |
| aroB-R | 36 |
| OL(24)-F | 37 |
| OL(24)-R | 38 |
| TS-20-OL(24)-F | 39 |
| TS-20-OL(24)-R | 40 |
| 4879_DEL_F | 41 |
| 4879_DEL_R | 42 |
| Amino acid sequence of Mq.VS | 43 |
| Amino acid sequence of AAE3_13291 | 44 |
| Amino acid sequence of Galma_229201 | 45 |
| Amino acid sequence of Moror_10831 (WG66_18985) | 46 |
| Amino acid sequence of Galma_245845 | 47 |
| Amino acid sequence of Galma_225678 | 48 |
| Amino acid sequence of Galma_63553 | 49 |
| Amino acid sequence of Galma_104215 | 50 |
| Amino acid sequence of Pilcr_81088 | 51 |
| Amino acid sequence of Pilcr_825684 | 52 |
| Amino acid sequence of Sphst_47084 | 53 |
| Amino acid sequence of Denbi1_816208 | 54 |
| Amino acid sequence of Moror_4213 | 55 |
| Amino acid sequence of Moror_10832 (WG66_18986) | 56 |
| Amino acid sequence of AAE3_12839 | 57 |
| Upstream nucleic acid sequences of strain #12 | 58 |
| Upstream nucleic acid sequence of strains #31-52 | 59 |
| Nucleic acid sequence of RBS of Design 1 | 60 |
| Nucleic acid sequence of RBS of Design 2 | 61 |
| Nucleic acid sequence of codon optimized VS sequence with N-terminal 6-histidine tag | 62 |
| Nucleic acid sequence of truncated VS (del2-85) sequence with N-terminal 6-histidine tag | 63 |

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method of increasing viridiflorol production in an isolated *Escherichia coli* host cell that produces one or more terpenoids, comprising:
   a) providing the isolated *Escherichia coli* host cell that produces one or more terpenoids, said host cell comprising a vector comprising a polynucleotide sequence encoding a terpene synthase enzyme, wherein the terpene synthase enzyme is viridiflorol synthase isolated from *Acrocybe aegerita*;
   b) modifying the vector by:
      i) introducing an inducible promoter operably linked to the polynucleotide sequence encoding the terpene synthase enzyme; and
      ii) introduce introducing a polynucleotide sequence encoding a ribosomal binding site (RBS) that optimizes translation initiation rate of the terpene synthase enzyme, wherein the polynucleotide sequence encoding the RBS is SEQ ID NO: 9, 10, 11 or 17;
   c) determining the dosage of an inducer capable of inducing the inducible promoter; and
   d) culturing the isolated *Escherichia coli* host cell in a culture medium in the presence of the inducer at the dosage determined from step c) to produce viridiflorol at an increased concentration and/or at an increased rate and/or at an increased carbon yield compared to an isolated *Escherichia coli* host cell that produces viridiflorol comprising a vector comprising a polynucleotide sequence encoding a terpene synthase enzyme that has not been modified.

2. The method of claim 1, wherein the isolated *Escherichia coli* host cell comprises one or more additional vectors, said one or more additional vectors comprising a polynucleotide sequence encoding one or more genes of the mevalonate pathway operably linked to an inducible promoter.

3. The method of claim 2, wherein the isolated *Escherichia coli* host cell further comprises two additional vectors, wherein the first additional vector comprises a polynucleotide sequence encoding the genes acetoacetyl-CoA thiolase (atoB), 3-hyoxy-3-methylglutaryl-CoA synthase (hmgS) and truncated 3-hyoxy-3- methylglutaryl-CoA reductase (hmgR) of the mevalonate pathway and the second additional vector comprises a polynucleotide sequence encoding the genes mevalonate kinase (mevK), phosphomevalonate kinase (pmK), phosphomevalonate decarboxylase (pmd) and isopentenyl pyrophosphate isomerase (idi) of the mevalonate pathway, wherein the genes of the mevalonate pathway are isolated from Saccharomyces cerevisiae and *Escherichia coli*.

4. The method of claim 1, wherein the inducible promoter is a T7 promoter variant selected from the group consisting of TM1, TM2 and TM3, wherein TM1, TM2 and TM3 have the polynucleotide sequence of SEQ ID NO: 28, SEQ ID NO: 29 and SEQ ID NO: 30, respectively.

5. The method of claim 4, wherein the inducible promoter in the vector comprising a polynucleotide sequence encoding a terpene synthase enzyme is TM1, the inducible promoter in the first additional vector comprising the acetoacetyl-CoA thiolase (atoB), 3-hyoxy-3-methylglutaryl-CoA synthase (hmgS) and truncated 3- hyoxy-3-methylglutaryl-CoA reductase (hmgR) genes is TM2, and the inducible promoter in the second additional vector comprising the genes mevalonate kinase (mevK), phosphomevalonate kinase (pmK), phosphomevalonate decarboxylase (pmd) and isopentenyl pyrophosphate isomerase (idi) genes is TM3.

6. The method of claim 1, wherein the polynucleotide sequence encoding the RBS is situated upstream of the polynucleotide sequence encoding the terpene synthase enzyme.

7. The method of claim 1, wherein the inducer is lactose or isopropyl β-D-1-thiogalactopyranoside (IPTG); optionally wherein the inducer dosage is determined using the product of the total promoter strength and the strength of the promoter operably linked to the mevalonate kinase (mevK), phosphomevalonate kinase (pmK), phosphomevalonate decarboxylase (pmd) and isopentenyl pyrophosphate isomerase (idi) genes; optionally wherein the inducer dosage is between about 0.001-0.5 mM IPTG or between about 0.1-50 mM lactose.

8. The method of claim 7, wherein the isolated *Escherichia coli* host cell is a DE3 strain encoding a T7 RNA polymerase integrated into its genome.

9. The method of claim 1, wherein the isolated *Escherichia coli* host cell is deficient in at least one gene involved in amino acid synthesis.

10. The method of claim 9, wherein the vector comprising a polynucleotide sequence encoding a terpene synthase enzyme and the one or more additional vectors further comprises a polynucleotide sequence encoding the one or more genes that the isolated *Escherichia coli* host cell is deficient in.

11. The method of claim 9, wherein the at least one gene is selected from the group consisting of 3-phosphoshikimate 1-carboxyvinyltransferase (aroA), 3-dehydroquinate synthase (aroB) and chorismate synthase (aroC), wherein the at least one gene is isolated from *Escherichia coli*.

12. The method of claim 1, wherein the vector comprising a polynucleotide sequence encoding a terpene synthase enzyme further comprises a polynucleotide sequence encoding the gene 3-phosphoshikimate 1-carboxyvinyltransferase (aroA).

13. The method of claim 3, wherein the first additional vector comprising a polynucleotide sequence encoding the genes atoB, hmgS and truncated hmgR further comprises a polynucleotide sequence encoding the gene aroC, and wherein the second additional vector comprises a polynucleotide sequence encoding the genes mevK, pmK, pmd and idi further comprises a polynucleotide sequence encoding the gene aroB.

14. The method of claim 1, wherein the viridiflorol synthase is mutated at one or more amino acid positions.

15. The method of claim 14, wherein the mutation is G227C, V314Y and deletion of amino acids at positions 2 to 85 of SEQ ID NO: 24.

16. The method of claim 1, wherein terpenoid production is increased by at least 2000 fold compared to an isolated *Escherichia coli* host cell that produces one or more terpenoids comprising a vector comprising a polynucleotide sequence encoding a terpene synthase enzyme that has not been modified.

* * * * *